US008548937B2

(12) United States Patent
Saigal et al.

(10) Patent No.: US 8,548,937 B2
(45) Date of Patent: Oct. 1, 2013

(54) MEDICAL CARE TREATMENT DECISION SUPPORT SYSTEM

(75) Inventors: Christopher Sharad Saigal, Beverly Hills, CA (US); Hollis Leech, Beverly Hills, CA (US)

(73) Assignee: WiserCare LLC, Beverly Hills, CA (US)

( * ) Notice: Subject to any disclaimer, the term of this patent is extended or adjusted under 35 U.S.C. 154(b) by 0 days.

(21) Appl. No.: 13/212,073

(22) Filed: Aug. 17, 2011

(65) Prior Publication Data
US 2012/0047105 A1 Feb. 23, 2012

Related U.S. Application Data

(60) Provisional application No. 61/500,517, filed on Jun. 23, 2011, provisional application No. 61/374,551, filed on Aug. 17, 2010, provisional application No. 61/480,282, filed on Apr. 28, 2011.

(51) Int. Cl.
*G06F 9/44* (2006.01)
*G06N 7/02* (2006.01)
*G06N 7/06* (2006.01)

(52) U.S. Cl.
USPC ............... 706/52; 705/2; 705/10; 703/11

(58) Field of Classification Search
None
See application file for complete search history.

(56) References Cited

U.S. PATENT DOCUMENTS

| | | | |
|---|---|---|---|
| 4,528,643 A | 7/1985 | Freeny, Jr. | |
| 4,733,354 A | 3/1988 | Potter et al. | |
| 4,839,822 A | 6/1989 | Dormond et al. | |
| 4,872,122 A | 10/1989 | Altschuler et al. | |
| 5,005,143 A | 4/1991 | Altschuler et al. | |
| 5,225,976 A | 7/1993 | Tawil | |
| 5,299,121 A | 3/1994 | Brill et al. | |
| 5,341,291 A | 8/1994 | Roizen et al. | |
| 5,471,382 A | 11/1995 | Tallman et al. | |

(Continued)

FOREIGN PATENT DOCUMENTS

| | | |
|---|---|---|
| WO | 9952025 A2 | 10/1999 |
| WO | 02054171 A2 | 7/2002 |

OTHER PUBLICATIONS

Lee, Chung Keun; International Search Report and Written Opinion of the International Searching Authority; dated Mar. 26, 2012; pp. 1-9; Korean Intellectual Property Office, Seo-gu, Daejeon, Republic of Korea.

(Continued)

*Primary Examiner* — Kakali Chaki
*Assistant Examiner* — Luis Sitiriche
(74) *Attorney, Agent, or Firm* — Khorsandi Patent Law Group, A Law Corporation; Marilyn R. Khorsandi

(57) ABSTRACT

Exemplary embodiments of the present invention will assist patients with their investigation of, and decision making about, the treatments that are available to them using conjoint analysis methods that measure individual preferences for risk-associated treatment options, while maintaining an acceptable interview length. In exemplary embodiments, such individual preferences, known as "utilities" in economics literature, will be combined with evidence-based outcomes data regarding the probabilities of treatment outcomes; exemplary embodiments will use "decision analysis" and modified "conjoint analysis" methods, to dynamically generate for patients real-time individualized, evidence-based feedback, rankings and recommendations regarding medical treatment alternatives that are available to the patient based on the patient's medical condition and prognostic indicators.

21 Claims, 38 Drawing Sheets

(56) References Cited

U.S. PATENT DOCUMENTS

| | | | |
|---|---|---|---|
| 5,517,405 | A | 5/1996 | McAndrew et al. |
| 5,583,758 | A | 12/1996 | McIlroy et al. |
| 5,586,024 | A | 12/1996 | Shaibani |
| 5,594,638 | A | 1/1997 | Iliff |
| 5,660,176 | A | 8/1997 | Iliff |
| 5,664,109 | A | 9/1997 | Johnson et al. |
| 5,711,297 | A | 1/1998 | Iliff |
| 5,716,382 | A | 2/1998 | Snell |
| 5,724,580 | A | 3/1998 | Levin et al. |
| 5,724,968 | A | 3/1998 | Iliff et al. |
| 5,757,917 | A | 5/1998 | Rose et al. |
| 5,764,923 | A | 6/1998 | Tallman et al. |
| 5,768,528 | A | 6/1998 | Stumm |
| 5,915,240 | A | 6/1999 | Karpf |
| 5,953,704 | A | 9/1999 | McIlroy et al. |
| 5,954,641 | A | 9/1999 | Kehr et al. |
| 5,964,700 | A | 10/1999 | Tallman et al. |
| 6,081,786 | A | 6/2000 | Barry et al. |
| 6,085,752 | A | 7/2000 | Kehr et al. |
| 6,102,855 | A | 8/2000 | Kehr et al. |
| 6,148,814 | A | 11/2000 | Clemmer et al. |
| 6,283,761 | B1 | 9/2001 | Joao |
| 6,304,773 | B1 | 10/2001 | Taylor |
| 6,581,038 | B1 | 6/2003 | Mahran |
| 6,584,445 | B2 | 6/2003 | Papageorge |
| 6,745,184 | B1 | 6/2004 | Choi et al. |
| 6,928,434 | B1 | 8/2005 | Choi et al. |
| 7,062,076 | B1 | 6/2006 | Osborne et al. |
| 7,398,270 | B1 | 7/2008 | Choi et al. |
| 7,877,346 | B2 | 1/2011 | Karty |
| 7,912,734 | B2 | 3/2011 | Kil |
| 2001/0023419 | A1 | 9/2001 | Lapointe et al. |
| 2001/0032099 | A1 | 10/2001 | Joao |
| 2001/0037215 | A1 | 11/2001 | Sparks |
| 2001/0047324 | A1 | 11/2001 | Hoffman |
| 2002/0165737 | A1 | 11/2002 | Mahran |
| 2002/0193667 | A1 | 12/2002 | McNair |
| 2003/0060688 | A1 | 3/2003 | Ciarniello et al. |
| 2003/0110059 | A1* | 6/2003 | Janas et al. ......... 705/2 |
| 2003/0163353 | A1* | 8/2003 | Luce et al. ......... 705/2 |
| 2003/0167265 | A1 | 9/2003 | Corynen |
| 2004/0103058 | A1 | 5/2004 | Hamilton |
| 2004/0107171 | A1 | 6/2004 | Basak et al. |
| 2004/0111291 | A1* | 6/2004 | Dust et al. ......... 705/2 |
| 2004/0260155 | A1 | 12/2004 | Ciarniello et al. |
| 2007/0156453 | A1 | 7/2007 | Frielinghaus et al. |
| 2007/0233730 | A1 | 10/2007 | Johnston |
| 2008/0147440 | A1 | 6/2008 | Kil |
| 2008/0172214 | A1* | 7/2008 | Col et al. ......... 703/11 |
| 2010/0010831 | A1 | 1/2010 | Fueyo et al. |
| 2010/0217650 | A1* | 8/2010 | Hartnell ......... 705/10 |
| 2011/0230360 | A1* | 9/2011 | Stephan et al. ......... 506/7 |

OTHER PUBLICATIONS

Johnson, Gary K., "Functional Requirements of a Computer-Based Patient Record System", Healthcare Financial Management, Jun. 1994, pp. 54-62, v48n6, 7 pages.

Chen, Pauline W., M.D."Finding the Patient in a Sea of Guidelines," The New York Times, May 19, 2011, http://well.blogs.nytimes.com/2011/05/19/finding-the-patient-in-a-sea-of-guidelines/?page..., pp. 1-3.

"Informatics Innovations", Aetna Integrated Informatics, undated—prior to Oct. 25, 2004, 11 pages.

Bowling, A., et al., "Measuring Patients' preferences for treatment and perceptions of risk", www.qualityhealthcare.com, Quality in Health Care 2001, 8 pages.

De Bekker-Grob, et al. "Preferences of GPs and Patients for Preventive Osteoporosis Drug Treatment: A Discrete-Choice Experiment", PharmacoEconomics, Issue 3, vol. 27, Publication Date Jun. 2010, 15 pages.

Essers, Brigitte AB, "Does the Inclusion of a Cost Attribute Result in Different Preferences for the Surgical Treatment of Primary Basal Cell Carcinoma?", PharmacoEconomics, Issue 6, vol. 28, Publication Date 2009, 17 pages.

Marshall, Deborah, Phd., "Using Preferences in Decision Making", University of Calgary, Oct. 25, 2009, 4 pages.

Mele, Nancy L. "Conjoint Analysis, Using a Market-Based Research Model for Healthcare Decision Making," Nursing Research, May/Jun. 2008, vol. 57, No. 3, pp. 220-224.

Leech, Hollis, "Delivering RAND Outcomes Data with Comprehensive Analytical Tool Set", iHealer, LLC, Nov. 2, 2001, 27 pages.

Christopher S. Saigal, et al., "Apparatus, Systems and Methods for Computer-Implemented, Evidence-Based Health Care Decision Analysis"; U.S. Appl. No. 10/061,449, filed Feb. 1, 2002, now Abandoned (including Specification pp. 1-32, Drawing pp. 33-72).

Office Action for U.S. Appl. No. 10/061,449, dated Apr. 26, 2006, pp. 1-11, USPTO, Art Unit 3626.

Leech, Hollis, "Getting to Informed Choice: HINT is not On-line Guidelines," iHealer, LLC, Aug. 4, 2003, 19 pages.

"Knowledge and Evaluation Research Unit—Victor M. Montori," Mayo Foundation for Medical Education and Research, http://mayoresearch.mayo.edu/mayo/research/ker_unit/decision-aids.cfm, undated, copyright 2012, 1 page.

* cited by examiner

FIG. 8

Your Treatment Options

| Your Diagnosis | Your Preferences | Your Treatment Options | Your Decision |

In order to determine which treatment options have the best chance of helping you, we need to ask you some questions about your prostate cancer diagnosis. We will use the results from several medical tests that your doctor should have ordered for you. If you run into a question that you don't know the answer to, or you simply haven't had the test in question, just select "I'm not sure". We'll keep track of which items you need to talk to your doctor about, and we'll give you a printable list at the end of this section if there are answers you still need to get.

804 — What is your PSA?  [7].[8] ng/dl — 805

806 — What is your Gleason score? (also know as 'grade')  [3]+[4] = 7 — 807

808 — What is the T-stage of your cancer?  [T2 ▽] — 809

810 — Are you African American?
  811 { ⦿ Yes, I am African American
       ○ No, I am not African American 812 — My doctor has confirmed with me that my prostate cancer is confined to my prostate (has not spread)
  ⦿ Yes   ○ No   ○ Not sure
  813

Help   Info

801 — [← Previous]   [Continue →] — 802

Clinical Assessment

| Your Diagnosis | Your Preferences | Your Treatment Options | Your Decision |

In order to determine which treatment options have the best chance of helping you, we need to ask you some questions about your prostate cancer diagnosis. We will use the results from several medical tests that your doctor should have ordered for you. If you run into a question that you don't know the answer to, or you simply haven't had the test in question, just select "I'm not sure". We'll keep track of which items you need to talk to your doctor about, and we'll give you a printable list at the end of this section if there are answers you still need to get.

For the conditions below, put a check in the box next to each illness that you have had (whether you are currently diagnosed with it or not). Why do we ask these questions?

- ☐ Myocardial infarction
- ☐ Connective tissue disease
- ☐ Moderate or severe renal failure
- ☐ Moderate or severe liver disease
- ☐ Chronic heart failure
- ☐ Peptic ulcer disease
- ☐ Diabetes mellitus with end organ damage
- ☐ AIDS
- ☐ Cerebrovascular accident
- ☐ Mild liver disease
- ☐ Any type of tumor
- ☐ Dementia
- ☑ Diabetes
- ☐ Lymphoma
- ☐ Chronic pulmonary disease
- ☐ Hemiplegia
- ☐ Leukemia

[← Previous]  [Continue →]

FIG. 9

Your Treatment Options

| Your Diagnosis | Your Preferences | Your Treatment Options | Your Decision |

Now we are going to ask you to compare and rate different outcomes and attributes related to prostate cancer treatment. We will ask you to make "trade-offs" among these outcomes and attributes in order to better understand what is most important to you. The outcomes and attributes we will be asking you to think about include:

- Effect of the treatment on urinary control - some treatments can cause leakage of urine, permanently or temporarily
- Effect of the treatment on sexual function - some treatments can diminish sexual function permanently or temporarily
- Effect of the treatment on bowel function - some treatments can cause overactive bowel symptoms, permanently or temporarily
- Invasiveness of the treatment - this can range from a major surgical procedure to completely non-invasive
- Recovery time - this can range from 4 weeks to none
- Potential for operative complications - some treatments risk complications such as blood clot in the leg, requiring long term medical therapy, while others have no risk for such complications
- Blood transfusion - some treatments have this risk, others do not
- Survival - some treatments may result in a longer survival period compared to others

[← Previous]  [Continue →]

FIG. 10

Your Treatment Options

| Your Diagnosis | Your Preferences | Your Treatment Options | Your Decision |

Now we are going to ask you to rank the importance of potential changes in one element of a treatment compared to other potential changes. Please move the change that matters the most to you to the top of the list, and the one that means the least to you to the bottom, and then continue to rank the changes until your list reflects how you feel.

Drag row and drop

| Rank 1120 | Attribute 1140 | From 1150 | Change | To 1160 | |
|---|---|---|---|---|---|
| 1 | Effect on Urinary control compared to before treatment | Leakage with cough or strain with no recovery | → | Temporary leakage with cough or strain - full recovery at 6 months 1190 | Most Valuable |
| 2 | Effect on Bowel function compared to before treatment | Rectal urgency / frequency with no recovery | → | No Change | |
| 3 | Effect on Sexual Function compared to before treatment | Much worse with no recovery | → | No Change 1190 | |
| 4 | Invasiveness of the medical treatment | General anesthesia - surgical incision into abdomen | → | Non-invasive 1190 | |
| 5 | Blood Transfusion | Needed | → | Not needed | |
| 6 | Operative complications | Blood clot in leg requiring long term medical therapy | → | None | |
| Rank | Recovery time | 4 weeks - urinary catheter for two weeks | → | Immediate 1190 | Least Valuable |

1110
1130

1101 ← Previous    Continue → 1102

FIG. 11

Your Treatment Options

| Your Diagnosis | Your Preferences | Your Treatment Options | Your Decision |

Now we are going to ask you to compare two specific possible improvements in how a treatment could affect you. Please use the slider below to show how many "importance points" you would give to each of the treatment improvements below. There are a fixed number of points you can use to score these improvements, so that as you move one bar to the right, the other would move to the left. If the bar on the top is twice as long as the bar on the bottom, you are saying that the improvement on the top is worth twice the improvement on the bottom.

Assume that all other attributes are equal

Drag color bar

1210 — Effect on Sexual function compared to before treatment

1212 Much worse with no recovery   1213 1214 No change   1218  50 1211
1216   1215   1219

1220 — Effect on Urinary control compared to before treatment

1222 Leakage with cough or strain with no recovery   Full recovery at 6 months   1224  70 1221
1226   1225  1229 1223  1228

The two improvements presented on this screen are in the relative order that you designated within the previous ranking section. However, please feel free to assign a greater value to whichever improvement that you now feel is more valuable.

1201 [← Previous]   1202 [Continue →]

Your Treatment Options

| Your Diagnosis | Your Preferences | Your Treatment Options | Your Decision |

Now we are going to ask you to rate how important the impact of recovery time from a treatment is to you. Assume that all the other possible outcomes of this treatment (e.g. effect on sexual function, survival) are the same, and only the issues below could vary.

Please rate how desirable to you are each of the following possibilities for Recovery time. Assume that all other attributes remain the same.

Drag color bar

1320 — 4 weeks - urinary catheter for two weeks

1330 — Immediate

1310 — Where would you place a recovery period of two days on this scale of possible treatment outcomes?

1   2   3   4   5   6   7   8   9   10
O   O   O   O   O   O   ⊙   O   O   O

1350

1301 [← Previous]    1302 [Continue →]

FIG. 14-2

Detailed Description Of Your Treatment Options

Read a detailed descripton of each of my treatment options.

[Learn More]

Community

Learn more about the treatment options other people with prostate cancer have chosen and their commentary on outcomes and side effects.

[Learn More]

Experimental Treatment Options

Learn more about possible experimental treatment options

[Learn More]

Your Treatment Options

WiserCare Decision Support Report:  Prostate Cancer

| Your Treatment Options | | Survival Rate (Efficacy) | Popularity | |
|---|---|---|---|---|
| Radiation Therapy (includes this, that and the other) | 64% | 86% | 38% | Learn More |
| Active Surveillance | 48% | 86% | 12% | Learn More |
| Brachytherapy | 25% | 86% | 8% | Learn More |
| Surgery (includes open and robotic) | 11% | 86% | 42% | Learn More |
| Bibliography Of Research See bibliography of research WiserCare used to calculate my results | | | | Learn More |

What are the WiserCare rankings based on?

- Your clinical data. Our system ensures that the treatment options presented are appropriate for your medical condition.
- Your preferences. View your preferences to see how they affected the ranking.
- Probabilities of possible side effects. We use industry standard data on the probability of the outcomes and side effects we asked you about. This has an important effect on how we rank treatment options for you. These probabilities may vary depending on your physician's experience and you should discuss these with your physician. See the probabilities we used to calculate your results.

FIG. 15-1

Your Treatment Options

Your Diagnosis > Your Preferences > Your Treatment Options > Your Decision

WiserCare Decision Support Report: Prostate Cancer

| Your Treatment Options | | | Survival Rate (Efficacy) | Popularity | |
|---|---|---|---|---|---|
| Radiation Therapy (includes this, that and the other) | | 64% | 86% | 38% | Learn More |
| Active Surveillance | | 48% | 86% | 12% | Learn More |
| Brachytherapy | | 25% | 86% | 8% | Learn More |
| Surgery (includes open and robotic) | | 11% | 86% | 42% | Learn More |
| Bibliography Of Research See bibliography of research WiserCare used to calculate my results | | | | | Learn More |

What are the WiserCare rankings based on?

- Your clinical data. Our system ensures that the treatment options presented are appropriate for <u>your medical condition.</u>
- Your preferences. <u>View your preferences</u> to see how they affected the ranking.
- Probabilities of possible side effects. We use industry standard data on the probability of the outcomes and side effects we asked you about. This has an important effect on how we rank treatment options for you. These probabilities may vary depending on your physician's experience and you should discuss these with your physician. <u>See the probabilities we used to calculate your results.</u>

Your Preferences (ordered according to important to you) — 1620

| | Relative effect on the ranking of treatment options — 1640 | Community comments |
|---|---|---|
| Sexual dysfunction | Low | ☐ 10 comments / 🗨 add comment |
| Urinary Incontinence | High | ☐ 3 comments / 🗨 add comment — 1660, 1670 |
| Bowel issues | Low | ☐ 9 comments / 🗨 add comment |
| Aversion to surgery | Low | ☐ 3 comments / 🗨 add comment |
| Hospital stay | | ☐ 1 comments / 🗨 add comment |
| Cost | Low | ☐ 10 comments / 🗨 add comment |

1630

1650 — "If you had rated this lower verses sexual dysfunction, it may have changed your ranking of treatment options"

[Revise Summary]

— 1610

Community Comments—Urinary incontinence (decreasing chronologically)

By-HealthyLiving, Denver, Co    December 23, 2010
_ _ _ _ _ _ _ _ _ _ _ _ _ _ _ _
_ _ _ _ _ _ Read More By-Daily_Runner, Miami, FL    August 5, 2010
_ _ _ _ _ _ _ _ _ _ _ _ _ _ _ _
_ _ _ _ _ _ Read More

— 1710, 1720

Your Treatment Options

| Your Diagnosis | > | Your Preferences | > | Your Treatment Options | > | Your Decision |

WiserCare Decision Support Report: Prostate Cancer

| Your Treatment Options | | Survival Rate (Efficacy) | Popularity | |
|---|---|---|---|---|
| Radiation Therapy (includes this, that and the other) | 64% | 86% | 38% | Learn More |
| Active Surveillance | 48% | 86% | 12% | Learn More |
| Brachytherapy | 25% | 86% | 8% | Learn More |
| Surgery (includes open and robotic) | 11% | 86% | 42% | Learn More |

Bibliography Of Research
See bibliography of research WiserCare used to calculate my results

[ Learn More ]

What are the WiserCare rankings based on?
- Your clinical data. Our system ensures that the treatment options presented are appropriate for your medical condition.
- Your preferences. View your preferences to see how they affected the ranking.
- Probabilities of possible side effects. We use industry standard data on the probability of the outcomes and side effects we asked you about. This has an important effect on how we rank treatment options for you. These probabilities may vary depending on your physician's experience and you should discuss these with your physician. See the probabilities we used to calculate your results.

| Survival | Sexual dysfunction | Urinary function | Bowel function | Other |
|---|---|---|---|---|
| | | Probability | | |

| Treatment | High | Medium | Low | Summary 2210 |
|---|---|---|---|---|
| Radiation therapy | 2% | 5% | 93% | Surgery has the highest risk of causing permanent or long lasting incontinence. Brachytherapy often causes temporary incontinence, but can also sometimes cause long lasting incontinence as well. Active Surveillance has no risk of changing your current state of urinary function. |
| Active surveillance | 0% | 0% | 100% | |
| Brachytherapy | 0% | 10% | 90% | |
| Surgery | 5% | 95% | 0% | |

| Survival | Sexual dysfunction | Urinary function | Bowel function | Other |
|---|---|---|---|---|
| | Probabilities for Northshore Medical Group — 2310 | | | 2320 |
| | (see how the physicians of Northshore Medical Group compare with the national average) | | | |

| Treatment | High | Medium | Low | Summary 2210 |
|---|---|---|---|---|
| Radiation therapy | 0% | 5% | 95% | Surgery has the highest risk of causing permanent or long lasting sexual dysfunction. Brachytherapy often causes temporary sexual dysfunction, but can also sometimes cause long lasting dysfunction. Active Surveillance has no risk of sexual dysfunction. |
| Active surveillance | 0% | 0% | 100% | |
| Brachytherapy | 25% | 0% | 75% | |
| Surgery | 25% | 75% | 0% | |

| Survival | Sexual dysfunction | Urinary function | Bowel function | Other |
|---|---|---|---|---|

| | | Probabilites 2310' | | | | |
|---|---|---|---|---|---|---|
| | | Northshore Medical Group | | | National Average | | |
| | Treatment | High | Medium | Low | High | Medium | Low |
| 1820a | Radiation therapy | 0% | 5% | 95% | 0% | 10% | 90% |
| 1820b | Active surveillance | 0% | 0% | 100% | 0% | 0% | 100% |
| 1820c | Brachytherapy | 25% | 0% | 75% | 25% | 0% | 75% |
| 1820d | Surgery | 25% | 75% | 0% | 35% | 65% | 0% |

| Survival | Sexual dysfunction | Urinary function | Bowel function | Other |
|---|---|---|---|---|

| | | Probabilites 2310' | | | Comparison with National Average |
|---|---|---|---|---|---|
| | | Northshore Medical Group | | | |
| | Treatment | High | Medium | Low | |
| 1820a | Radiation therapy | 0% | 5% | 95% | ● — 2610 |
| 1820b | Active surveillance | 0% | 0% | 100% | ◐ — 2620 |
| 1820c | Brachytherapy | 25% | 0% | 75% | ○ — 2630 |
| 1820d | Surgery | 25% | 75% | 0% | ● — 2640 |

| List of physicians | | | |
|---|---|---|---|
| | Outcomes | User Rating | |
| Jim Jones, MD | ○ | | |
| Phil Smith, MD | ● | | |
| Rob Ross, MD | ◐ | | |
| Bill Baker, MD | ○ | | |

FIG. 27

List of physicians (click on the physician's name to see probabilities in detail)

| | Outcomes | | | | |
|---|---|---|---|---|---|
| | Survival | Sexual Function | Bowel Function | Urinary Function | Other |
| Jim Jones, MD | ○ | ◐ | ● | ◐ | ○ |
| Phil Smith, MD | ● | ● | ○ | ● | ● |
| Rob Ross, MD | ◐ | ○ | ◐ | ◐ | ● |
| Bill Baker, MD | ○ | ◐ | ○ | ○ | ◐ |

FIG. 28

Probability Comparisons (click to see probabilities in detail)

| | Outcomes | | | | |
|---|---|---|---|---|---|
| | Survival | Sexual Function | Bowel Function | Urinary Function | Other |
| Northshore Medical Group | ● | ● | ○ | ● | ● |
| National Average | ○ | ◐ | ● | ◐ | ○ |

FIG. 30

Patient Identifier: 9999 1234 ABC —3010
Patient Name: XJX YSYSY —3020
Patient Condition: Prostate Cancer —3025
3030— Treatment Used: Surgery  | MM | DD | YY | —3035
Facility Used: AZDC Hospital —3040
Physician Name: Jim Jones —3006
Physician Identifier: 1111 5555YZWX —3008
Physician Group Name: Northshore —3004
Physician Group Identifier: 29341678 —3002
Treatment Outcomes and Patient Ratings: —3042

3050— Treatment Satisfaction: [High ▽]
　　　　　　　　　　　　　　　3052  3054
3056— Urinary Function Impact: [None ▽]
　　　　　　　　　　　　　　　3058  3059
3060— Patient Rating: [High ▽]
　　　　　　　　　　　3062  3064
3066— Sexual Dysfunction Impact: [None ▽]
　　　　　　　　　　　　　　　　3067  3068
3070— Patient Rating: [High ▽]
　　　　　　　　　　　3072  3074
3076— Bowel Function Impact: [None ▽]
　　　　　　　　　　　　　　　3078  3079
3080— Patient Rating: [High ▽]
　　　　　　　　　　　3082  3084
3086— Patient Rating of Physician: [High ▽]
　　　　　　　　　　　　　　　　　3088  3089
3090— Patient Rating of Facility: [High ▽]
　　　　　　　　　　　　　　　　3092  3093
3095— Patient Comments: [very pleased... ▽]
　　　　　　　　　　3097                    } 3098

FIG. 32

Patient Identifier: _____ ⟵~3201
Patient Name: _____ ⟵~3203
Patient Condition: _____ ⟵~3205
Treatment Selected: _____ ⟵~3207
Insurance Company: _____ ⟵~3210
Insurance Plan: _____ ⟵~3215
Zip Code: _____ ⟵~3220

Physician/Physician Group Search:

3230 ⟶ ☐ Physician

3240 ⟶ ☐ Physician Group

3250 ⟶ ☐ Within [▽] miles from your zip code
         3252⌐ 3254⌐

3255 ⟶ ☐ that accepts your insurance plan

3260 ⟶ ☐ that is approved by/within the network for your insurance company/plan

MEDICAL CARE TREATMENT DECISION SUPPORT SYSTEM

CROSS-REFERENCE TO RELATED APPLICATIONS

This application claims priority to: U.S. Provisional Application Ser. No. 61/500,517, filed Jun. 23, 2011, entitled "Medical Care Treatment Decision Support System;" U.S. Provisional Application Ser. No. 61/374,551, filed Aug. 17, 2010, entitled "Medical Care Treatment Decision Support System;" and U.S. Provisional Application Ser. No. 61/480,282, filed Apr. 28, 2011; entitled "Medical Care Treatment Decision Support System;" the disclosures of all of which are incorporated for all purposes by reference herein as is fully stated herein.

FIELD OF THE INVENTION

The field of the present invention is decision support systems, and more specifically, a decision support system for use by individuals to analyze medical care treatment alternatives that are available to them and to select a treatment option that suits their individual preferences.

BACKGROUND OF THE INVENTION

Various medical care treatment alternatives may be available to a patient with a particular medical condition. The treatment alternatives that may be available to a particular patient for a particular medical condition may be dependent on a number of medical factors, sometimes referred to herein as prognostic indicators. Further, a number of side-effects and/or treatment results or effects may be associated with each different alternative.

For example, a woman diagnosed with breast cancer may have numerous treatment alternatives to consider, such as, radiation therapy, chemotherapy, breast-conserving surgery, breast-conserving surgery combined with radiation therapy, modified radical mastectomy followed by breast reconstruction surgery. Each treatment alternative for a particular medical condition may have various negative side effects and/or risk/success factors. For example, radiation or chemotherapy alone might have negative side effects such as hair loss and/or fatigue; depending on the particular patient's prognostic indicators, radiation or chemotherapy alone may have a relatively high risk of failure. Breast-conserving surgery, depending on a particular patient's prognostic indicators, may have a relatively low risk of failure and may have the positive effects of little or no effect on breast appearance. For yet other women, depending on a particular patient's prognostic indicators, breast-conserving surgery alone may have a medium risk of failure; whereas breast-conserving surgery combined with post-surgery radiation treatment may have a relatively low risk of failure. Modified radical mastectomy may have a relatively low risk of failure but would involve more pain, longer recovery time, and depending on a particular patient's preferences, subsequent breast-reconstruction surgery.

Further, because of the time that may be involved in educating a patient about the patient's medical condition and the various available treatment alternatives, medical care professionals may present only a partial picture of alternatives for a particular patient's consideration.

A patient, especially one confronting a serious, complex and/or dangerous medical condition, may be overwhelmed with the variations of available treatment alternatives and associated success/failure statistics and positive and/or negative effects. Further, it may be beyond a particular patient's capabilities to match his/her own preferences regarding possible positive and negative effects of treatment with the probabilities of these effects associated with the various available treatment alternatives. Thus, a patient may be confronted with not only the seriousness of the patient's medical condition but with the complexities of selecting a path for medical treatment.

Some way is needed to assist patients with their education regarding, and with their investigation and selection of, available medical treatment alternatives.

Decision analysis methodologies have been used in the past to model complex choices at the level of populations. Such population-level models manage competing probabilities, but require that an analyst assign a subjective value to model outcomes, such as, for example, "survival with a colostomy bag." In such population-level models, methods of assigning these values have been taken from the field of health economics and include rating scale, time trade off, and standard gamble methods. These methods have been found to have significant limitations. A new method of assessing patient preferences for use in decision analysis models is required to improve their accuracy and effectiveness.

Conjoint analysis has been used in marketing applications. In marketing applications of conjoint analysis, a number of participants (such as, for example, a statistical sampling of a market population) may be provided with various products from which to choose and asked to express their respective product preferences by making product choices. From the product choices made by the various participants of the surveyed population, consumer preferences for product features can be measured quantitatively using conjoint analysis. From the derived consumer preferences, new or existing products may be tailored to meet the market population preferences.

Conjoint analysis has been used to measure consumer preferences in a market by testing a small number of product attributes with a relatively small number of combinations using a sample population of individuals to model overall market preferences. In the context of a patient who is trying to make a decision about which of various treatment options to select, treatment options (sometimes referred to herein as treatment alternatives) may be thought of as somewhat analogous to "products." However, unlike "products" in a marketing context, treatment options in a medical context are associated with certain risks, or probabilities. For example, a particular patient with a certain type of cancer and with certain prognostic indicators may have the medical treatment options of chemotherapy without surgery, a conservative surgery followed by chemotherapy, or a radical surgery followed by chemotherapy. The particular patient might consider the option of chemotherapy without surgery to be attractive because there is no surgery. However, that option may be associated with a high risk of recurrence of the cancer and/or death for the particular patient's medical condition, and/or when considered in combination with the particular patient's prognostic indicators.

Further, unlike "products" in a marketing context for which consumer preferences are constructed by getting partial preference information from a large number of individuals in a survey population, which is then merged using conjoint analysis in a back-end application, an individual with medical treatment options requires an individualized (i.e. "patient-specific") analysis of the patient's preferences with respect to the various available treatment options in view of the patient's medical condition and in view of the patient's own prognostic indicators. Thus, all preference data on a treatment "product" must be gathered from one individual.

Additionally, a patient making a medical decision would value "real time" analytics to help in making what could be an urgent choice for the patient; whereas analyzing data at a time point remote from the interview would not be useful for a patient making such an urgent medical decision.

Yet further, unlike most "products" in a marketing context for which there may only be a small number of attributes, medical treatment options may be associated with a relatively high number of risk-based attributes, such as possible "outcomes" and/or side effects. For example, treatment options for a particular type of prostate cancer could involve various levels of various outcomes, including various levels of changes in sexual function, urinary function, and bowel function, could have various levels of invasiveness, recovery time and survival rates, could involve complications, and could require blood transfusion.

In order to evaluate preferences regarding the relatively high number of attributes and attribute levels that may be associated with medical treatment options, existing conjoint analysis methods would involve a high number of preference assessment exercises. However, the higher the number of preference assessment exercises (which may sometimes be referred to herein as "preference exercises"), the less user-friendly the method; the less user=friendly the method, the less likely a patient would be to complete the exercises. Additionally, increasing the number of preference assessment exercises increases the possibility of cognitive failure and error in the respondent, which may limit the usefulness of the resulting preference data.

Existing conjoint analysis methods would not work to measure a single person's preferences for various risk-associated treatment options in real time and to use the results to model that person's preferences for a number of risk-associated treatment options in combination with the risks associated with those treatment options. Rather, in order to assist patients with their investigation of, and decision making about, the treatments that are available to them, some way is needed to use conjoint analysis methods to provide a measurement of individual preferences for risk-associated treatment options in real time, while maintaining an acceptable interview length; a way is needed to minimize the number of preference-assessment exercises while still providing a high level of fit to a patient's preferences.

Further, once a patient or other user has selected, or tentatively selects, a treatment, a way is needed for the patient/user to search for physicians and/or physician groups that have demonstrated success in providing the selected treatment.

SUMMARY OF THE INVENTION

Exemplary embodiments of the present invention will assist patients with their investigation of, and decision making about, the treatments (sometimes referred to herein as "treatment options" or "treatment alternatives") that are available to them using conjoint analysis methods that measure individual preferences for risk-associated treatment options, while maintaining an acceptable interview length. In exemplary embodiments, such individual preferences, known as "utilities" in economics literature, will be combined with evidence-based outcomes data regarding the probabilities of treatment outcomes; exemplary embodiments will use "decision analysis" and modified "conjoint analysis" methods, to provide patients with tailored, evidence-based feedback on appropriate treatment.

Exemplary embodiments of the present invention would provide patient-specific, medical-condition-specific medical care treatment education, analysis and selection recommendations. One exemplary embodiment would provide dynamically generate real-time individualized, patient-specific, medical-condition-specific, conjoint-analysis-based medical care treatment alternative decision analysis and recommendations. Exemplary embodiments would apply conjoint analysis of a single patient's choices and preferences regarding medical treatment alternatives available for the particular patient, to risk-based outcomes based on probabilistic information associated with such outcomes, and in view of a particular patient's medical condition and the patient's own prognostic indicators.

One exemplary embodiment would adapt an Adaptive Self-Explication of Multi-Attribute Preferences ("ASEMAP") approach for conjoint analysis; by way of a non-limiting example, exemplary ASEMAP Software, available through V. Srinivasan Business Consulting, Stanford, Calif., could be adapted to implement a system adapting the ASEMAP conjoint analysis methodology. Another exemplary embodiment would adapt Choice-Based conjoint analysis methodology; by way of non-limiting example, exemplary CBC SYSTEM software, available through SAWTOOTH SOFTWARE of Sequim, Wash. could be adapted to implement a system adapting the Choice-Based conjoint analysis methodology. Yet another exemplary embodiment would adapt a Fast Polyhedral Method ("FPM") for conjoint analysis; by way of non-limiting example, exemplary "FAST-PACE" software, available through the Massachusetts Institute of Technology ("MIT"), could be adapted to implement a system adapting the FPM conjoint analysis methodology. It will be understood by someone with ordinary skill in the art that adaptation of a particular methodology for conjoint analysis is not a limitation of the present invention. Rather, other conjoint analysis methodologies, whether now known or in the future discovered, could be adapted without departing from the spirit of the present invention. Further, it will be understood by someone with ordinary skill in the art that description herein of adaptation of exemplary existing software, such as SAWTOOTH, ASEMAP and FASTPACE, is not a limitation of the present invention. Rather, other software implementing conjoint analysis may be adapted without departing from the spirit of the present invention. It will be understood by someone with ordinary skill in the art that adaptation of existing conjoint analysis software would involve adapting and/or modifying such existing software in order for it to work with embodiments of the present invention. Alternatively, exemplary custom conjoint analysis software, an exemplary embodiment of which is described below, may be used for conjoint analysis of an individual patient's preferences.

From the exemplary aforementioned conjoint analysis, each medical treatment option available to the patient would be ranked according to the patient's preferences and the aforementioned risk-based outcomes and related prognostic indicators, and patient-specific recommendations would be provided.

Some exemplary embodiments would provide a computer system for providing medical treatment decision support regarding a patient's medical condition, said computer system comprising at least one computer device programmed to: in response to an input by a user of a patient medical condition and associated prognostic indicators, and according to the patient medical condition and said associated prognostic indicators, use statistically-structured, risk-based decision analysis models and related mapping trees comprising an indication of medical treatment options available for the patient and associated treatment attributes to generate a series of interactive medical treatment option selection exercises for the user, each medical treatment option selection exercise comprising at least two selectable medical treatment options available for the patient, each selectable medical treatment option comprising a display of a set of associated treatment attributes; and present the series of interactive medical treatment option selection exercises to the user. In one exemplary embodiment, the at least one computer device would be further programmed to present a recommendation of a medical treatment option according to a respective ranking of each medical treatment option available to the patient, said respective ranking comprising a calculation based on a conjoint analysis of a series of selections by the user of treatment options with associated treatment attributes selected from the series of interactive medical treatment option selection exercises. In another exemplary embodiment, in response to a series of selections by the user of treatment options selected from the series of interactive medical treatment option selection exercises, the at least one computer device would be further programmed to: determine a respective treatment utility value of each medical treatment option available for the patient, rank each medical treatment option available for the patient according to the respective treatment utility value, and present a recommendation of a medical treatment option available for the patient according to said rank.

In some exemplary embodiments, in addition to determining and presenting a medical treatment option recommendation, an analysis of sensitivity by the user to certain aspects of treatment would be performed and presented to the user. The user would be provided with a choice to retake the series of interactive medical treatment option selection exercises in view of the user's sensitivities. If the user chose to retake the exercises, such an exemplary embodiment would record the user's selections that resulted from retaking the exercises, and would determine a further recommendation of a further medical treatment option for the patient that would reflect the user's changes in preferences in view of the user's sensitivities.

Some exemplary embodiments would provide a computer-implemented method for providing medical treatment decision support regarding a patient's medical condition. An exemplary computer-implemented embodiment method would comprise: collecting, using a computer, an identification of a particular patient's medical condition; collecting, using a computer, information regarding the particular patient's prognostic indicators; generating, using a computer, a series of patient preference-assessment exercises according to the particular patient's medical condition and the particular patient's prognostic indicators, each patient preference-assessment exercise comprising information selected from the group consisting of: at least one medical treatment alternative available for the particular patient according to the particular patient's medical condition and the particular patient's prognostic indicators, at least one medical treatment effect associated with said at least one medical treatment alternative, and at least one medical treatment factor associated with said at least one medical treatment alternative; collecting, using a computer, a user's preferences regarding patient preference-assessment exercises in the series; determining, using a computer, utility values for medical treatment information, such as, for example, treatment attributes, side effects and outcomes selected from the group consisting of: said at least one medical treatment alternative, said at least one medical treatment effect, and said at least one medical treatment factor; determining, using a computer, a ranking of each medical treatment alternative available for the particular patient according to the particular patient's medical condition and according to the particular patient's prognostic indicators, said ranking determined according to said utility values and according to respective probabilistic data regarding said medical treatment effects and said medical treatment factors; and displaying a recommendation of a particular medical treatment alternative according to said ranking.

Some exemplary embodiments would provide a computer system for providing medical treatment decision support regarding a patient's medical condition, said computer system comprising at least one computer device programmed to: receive a user input of a patient medical condition and prognostic indicators regarding the patient, said patient medical condition and prognostic indicators corresponding to a particular patient; and in response to the user input of the patient medical condition and prognostic indicators regarding the patient: analyze the patient medical condition and prognostic indicators, determine a set of medical treatment alternatives associated with the patient medical condition according to said prognostic indicators, select a first subset of the set of medical treatment alternatives, and present a first interactive selection exercise of each medical treatment alternative in the first subset, said first selection exercise comprising an indication of each medical treatment alternative in the first subset and further comprising an indication of each attribute, effect and/or factor associated with each medical treatment alternative in the first subset.

Some exemplary embodiments would provide a computer system, such as an Internet-based computer system, for providing medical treatment decision support regarding a patient's medical condition. In an exemplary Internet-based embodiment, the exemplary computer system would comprise at least one computer device, such as an exemplary server computer, that would be programmed to: collect user input from a user, such as from a client computer. Exemplary user input would comprise a patient medical condition regarding a particular patient, and prognostic indicators associated with the particular patient. One exemplary Internet-based embodiment would use conjoint analysis to analyze a user's/patient's choices and related preferences regarding medical treatment attributes and treatment outcomes for the medical treatments that would be available for a particular patient, based on probabilistic information associated with such outcomes, and in view of a particular patient's medical condition and prognostic indicators.

One exemplary Internet-based embodiment would adapt one or more of an ASEMAP, FPM, or Choice-Based (or other conjoint analysis methodologies, whether now known or in the future discovered) approach for conjoint analysis and related existing software (e.g., ASEMAP, FASTPACE, CBC SYSTEM or other software, whether now known or in the future discovered). Alternatively, an exemplary embodiment of exemplary custom Internet-based conjoint analysis software is described below for conjoint analysis of an individual patient's preferences.

In one exemplary Internet-based embodiment, such as, by way of non-limiting example, an adapted ASEMAP-conjoint-analysis-based embodiment or a custom conjoint analysis software embodiment, in response to the user input of the patient medical condition and prognostic indicators regarding the patient, the exemplary server computer (whether alone or in conjunction with one or more other computer devices) would be further programmed to display to a display device in communication with the client computer, an interactive set of medical treatment attributes and corresponding treatment outcomes that would be associated with various treatment alternatives that would be available to the particular patient according to the patient medical condition and according to the prognostic indicators associated with the particular patient.

In such an exemplary Internet-based embodiment, the exemplary server computer (whether alone or in conjunction with one or more other computer devices) would be further programmed to prompt the user to rank possible improvements in outcomes related to each relevant treatment attribute, with respect to each other medical treatment attributes and corresponding treatment outcomes in the interactive set of medical treatment attributes and corresponding treatment outcomes.

In response to a user input of a ranking of each medical treatment attribute and corresponding treatment outcome, the exemplary server computer (whether alone or in conjunction with one or more other computer devices) would be further programmed to display to the display device in communication with the client computer, an interactive series of user-preference rating exercises and user rating comparison exercises, each exercise prompting the user to input a rating and/or a comparison rating for various medical treatment attributes and corresponding treatment outcomes.

In such an exemplary Internet-based embodiment, the exemplary server computer (whether alone or in conjunction with one or more other computer devices) would be further programmed to rank each medical treatment alternative available for the particular patient according to: the patient medical condition, the prognostic indicators associated with the particular patient, the user input of the ranking of each medical treatment attribute and corresponding treatment outcome and the rating and/or the comparison rating for various medical treatment attributes and corresponding treatment outcomes. In such an exemplary Internet-based embodiment, the exemplary server computer (whether alone or in conjunction with one or more other computer devices) would be further programmed to display to the display device in communication with the client computer, a ranking of various medical treatments available to the particular patient.

In one such exemplary Internet-based embodiment, the exemplary server computer (whether alone or in conjunction with one or more other computer devices) would be further programmed to display the ranking of each medical treatment to the display device in communication with the client computer with a graphic depiction of the ranking of said medical treatment.

In one such exemplary Internet-based embodiment, the exemplary server computer (whether alone or in conjunction with one or more other computer devices) would be further programmed to display a Survival Rate corresponding to each ranking of each medical treatment, in cases where survival was an outcome of interest.

In one such exemplary Internet-based embodiment, the exemplary server computer (whether alone or in conjunction with one or more other computer devices) would be further programmed to display a popularity ranking associated with each medical treatment. In one such exemplary Internet-based embodiment, the popularity ranking would be based on treatment alternatives selected by other users of the exemplary Internet-based embodiment with similar medical conditions and/or prognostic indicators. In another exemplary Internet-based embodiment, the popularity ranking would be based on national statistics of treatment alternatives selected by other patients with similar medical conditions and/or prognostic indicators.

An alternative exemplary embodiment would provide side-by-side comparison displays of provider/provider group outcome and side effect treatment probabilities as compared to national averages. Exemplary displays would display detailed probabilities, or alternatively, graphic representations of comparisons.

A further alternative exemplary embodiment of the present invention would provide user interfaces for input of provider/provider group treatment outcome data and/or for input of patient treatment outcome data and comments and/or ratings of physicians, physician groups and/or facilities.

An exemplary embodiment of the present invention would further facilitate patient identification and/or selection of a physician and/or a physician group and/or a facility according to treatment training, treatment experience, treatment outcome results and/or treatment patient ratings.

In one exemplary Internet-based embodiment, such as an ASEMAP-adapted conjoint-analysis-based embodiment or a custom conjoint analysis software embodiment, in response to a user input through a client computer of a patient medical condition and prognostic indicators regarding the patient, the exemplary server computer (whether alone or in conjunction with one or more other computer devices) would be programmed to identify and analyze one or more mapping trees of treatment alternatives associated with a patient's medical condition and identify treatment alternatives that would be available to the particular patient according to the patient medical condition and according to the prognostic indicators associated with the patient; the exemplary server computer (whether alone or in conjunction with one or more other computer devices) would be further programmed to analyze statistically-structured, risk-based decision analysis models comprising risk-based treatment attributes and outcomes statistically associated with said treatment alternatives; the exemplary server computer (whether alone or in conjunction with one or more other computer devices) would be further programmed to generate for display to a display device in communication with the client computer, an interactive set of preference-assessment exercises, each preference-assessment exercise comprising a set of alternative medical treatments, corresponding medical treatment attributes and corresponding possible risk-based treatment outcomes and further comprising an interactive prompt for user input of an expression of patient preference regarding the set of alternative medical treatments and their outcomes.

In such an exemplary Internet-based embodiment, the exemplary server computer (whether alone or in conjunction with one or more other computer devices) would be further programmed to receive user input of an expression of patient preference regarding the set of alternative medical treatments, to perform conjoint analysis to analyze said user input with respect to said risk-based treatment attributes and outcomes, to rank said treatment alternatives according to results of said conjoint analysis and to present, such as through a display to a display device, said rank of said treatment alternatives to the user.

BRIEF DESCRIPTION OF THE DRAWINGS

These and other features of the present invention are more fully set forth in the following description of exemplary embodiments of the invention. The description is presented with reference to the accompanying drawings in which:

FIG. 8 is a graphic depiction of an exemplary interactive user interface prognostic indicator data collection screen in an exemplary embodiment of the present invention;

FIG. 9 is a graphic depiction of an exemplary interactive user interface prognostic indicator clinical assessment data collection screen in an exemplary embodiment of the present invention;

FIG. 10 is a graphic depiction of an exemplary user interface treatment attribute and outcome description screen in an exemplary embodiment of the present invention;

FIG. 11 is a graphic depiction of an exemplary interactive user interface treatment option changes rating screen in an exemplary embodiment of the present invention;

FIG. 12 is a graphic depiction of an exemplary interactive user interface treatment option comparison rating screen in an exemplary embodiment of the present invention;

FIG. 13 is a graphic depiction of an exemplary interactive user interface in which the treatment attribute, recovery time, is being rated in an exemplary embodiment of the present invention;

FIG. 22 is a graphic depiction of an exemplary National Average Treatment Outcomes and Probabilities screen in an alternative exemplary Probabilities of Outcomes and Side Effects user interface in an exemplary alternative embodiment of the present invention;

FIG. 23 is a graphic depiction of an exemplary Provider Group Treatment Outcomes and Probabilities screen in an alternative exemplary Probabilities of Outcomes and Side Effects user interface in a further alternative exemplary embodiment of the present invention;

FIG. 24 is a graphic depiction of an exemplary Provider Group Treatment Outcomes and Probabilities Comparison screen comparing provider group treatment outcomes and probabilities to national averages in an alternative exemplary Probabilities of Outcomes and Side Effects user interface in a further alternative exemplary embodiment of the present invention;

FIG. 25 is a graphic depiction of an exemplary Provider Group Treatment Outcomes and Probabilities Graphical Comparison screen that graphically represents comparisons between provider group treatment outcomes and probabilities and national averages in an alternative exemplary Probabilities of Outcomes and Side Effects user interface in a further alternative exemplary embodiment of the present invention;

FIG. 26 is a graphic depiction of an exemplary Physician Treatment Summary Graphical Comparisons screen graphically showing physician treatment summary comparisons for an exemplary treatment with national averages for the same exemplary treatment in an alternative exemplary embodiment of the present invention;

FIG. 27 is a graphic depiction of an exemplary Physician Treatment Outcomes Graphical Comparisons screen graphically showing physician treatment outcomes for an exemplary treatment as compared to national averages for the same exemplary treatment in an alternative exemplary embodiment of the present invention;

FIG. 28 is a graphic depiction of an exemplary Physician Group Outcome Comparisons With National Averages screen for an exemplary treatment in an exemplary embodiment of the present invention;

FIG. 30 is a graphic depiction of an exemplary Patient User Treatment Outcomes and Ratings Interface for input and collection of a particular patient's treatment outcome data and rating information in an exemplary embodiment of the present invention;

FIG. 32 is a graphic depiction of an exemplary Patient Physician/Physician Group Search Request Interface for searching for a physician and/or a physician group to provide a selected treatment;

DETAILED DESCRIPTION OF THE INVENTION

The exemplary embodiment will assist patients with their investigation of, and decision making about, medical treatments that are available to them using conjoint analysis to measure the patient's preferences for risk-associated treatment options. In the exemplary embodiment, the process of patient preference measurement may be viewed in two parts: first, the measurement of the patient's utility for various treatments and associated attributes, effects, features and/or factors, and in particular, the approach to data collection; and second, the specification and estimation of a statistical model to determine utility values based on the patient's/user's responses to the measurement task. Various ways of collecting a patient's/user's input and then modeling the utility values according to that input may be used as will be described further below.

Figure 1A:
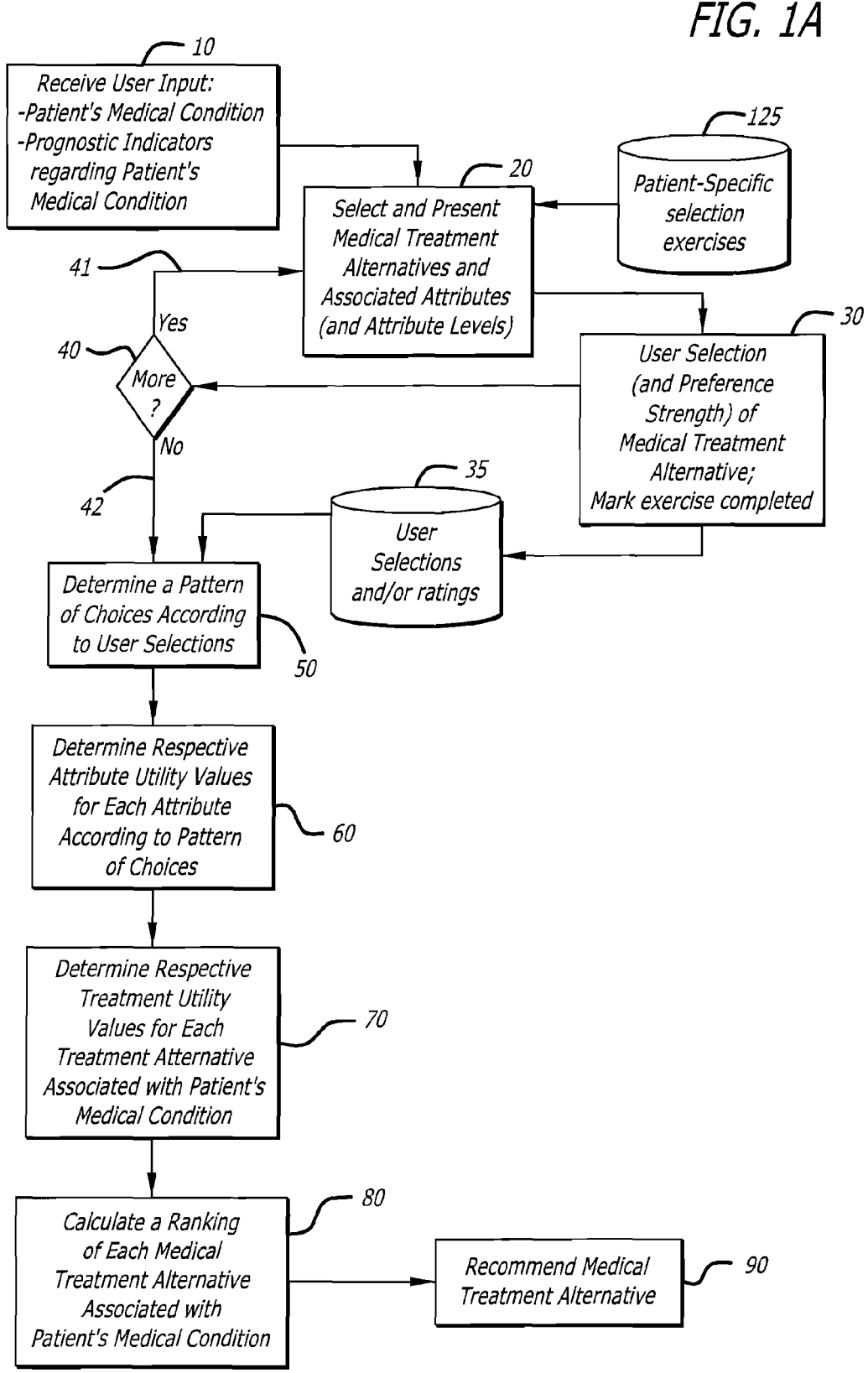
FIG. 1A is a high-level flow diagram depicting exemplary high-level logic functions of exemplary computer-implemented methods and exemplary computer system functions for providing medical treatment decision support regarding a patient's medical condition in an exemplary embodiment of the present invention.

FIG. 1A is a high-level flow diagram depicting exemplary high-level logic functions of exemplary computer-implemented methods and exemplary computer system functions for providing medical treatment decision support regarding a patient's medical condition. Exemplary embodiments would provide a computer system comprising at least one computer device that would be programmed to, as depicted in FIG. 1A, receive 10 a user input of a patient medical condition and prognostic indicators regarding the patient medical condition. In the exemplary embodiment depicted in FIG. 1A, the patient medical condition and prognostic indicators would correspond to a particular patient.

A user of the system may comprise a patient, a patient's representative, a health care provider, an insurer or other payor, an EMR (Electronic Medical Records) system, or any combination. For example, in the exemplary embodiment, a patient may enter the patient's basic identification information and establish a password for the patient, and in some embodiments, a second password for the patient's health care provider. In the exemplary embodiment, once the patient provides the patient's health care provider with the appropriate password, the patient's health care provider, or possibly multiple health care providers, could input the patient's medical condition and prognostic indicators. For example, for a patient who had received different types of diagnostic laboratory and imaging tests, the test results could be input by the respective testing providers.

Alternatively, all of the test results could be given to the patient's primary care physician and input by the primary care physician. Alternatively, the patient could input the patient's medical condition and prognostic indicators. In view of the above-described illustrative examples, it will therefore be understood by someone with ordinary skill in the art that reference to user input herein may involve a single user's input, or input from multiple users, and that the users may comprise patients, health care providers, insurers, payors, EMR (Electronic Medical Records) systems, and others.

The correspondence of a medical condition and/or prognostic indicators, or information determined or calculated in correspondence, to a particular patient may sometimes be referred to herein as "patient-specific." For example, a medical condition of a particular patient may sometimes be referred to herein as a patient-specific medical condition. Prognostic indicators for a particular patient may sometimes be referred to herein as patient-specific prognostic indicators. Information related to a particular medical condition may sometimes be referred to herein as "medical-condition-specific." Information related to a particular medical treatment alternative may sometimes be referred to herein as "treatment-specific." Information related to a particular attribute, effect or feature/factor of a particular medical treatment may sometimes be referred to as "attribute-specific." In the exemplary embodiment depicted in FIG. 1A, in response to the user input of the patient medical condition and prognostic indicators regarding the patient medical condition, a series (20, 30 and 40) of medical treatment alternative selection exercises would be presented to a user as depicted in exemplary function 20. Each medical treatment alternative selection exercise may sometimes be referred to herein as a "selection exercise," a "vignette," a "selection display," a "choice-based exercise," or in the case of Max-diff analysis, "best-worst choice exercises," or by similar terms. The series of selection exercises may sometimes be referred to herein as a patient interview, a user interview, or as an interview.

The exemplary embodiment of the present invention will use conjoint-analysis-based, interactive computer-administered interviews. It will be understood by someone with ordinary skill in the art that there are various ways to present user/patient interviews to obtain the user's/patient's preferences. One way would be to present a series of effects or conditions of medical treatment and ask the user/patient to rate each effect or condition according to the user's/patient's value/preference. For example, a condition of losing a person's hair (such as after chemotherapy) could be presented to a user/patient and the patient could be given an interactive sliding scale to rate the user's/patient's value of that condition. Another way might be to present a medical treatment with a variety of conditions/effects of the treatment described and ask the user/patient to rate the treatment based on the described conditions/effects. Yet another way would be to use a conjoint-analysis-based interview that would present a series of conjoint-analysis-based exercises with which the user/patient expresses the user's/patient's preferences.

It will be understood by someone with ordinary skill in the art that conjoint analysis, and conjoint-analysis-based interviews, may be conducted in different ways using various methodologies and modeling approaches. One type of conjoint analysis involves interviews that ask users to express their preferences by rating different choices in a series of interview exercises. That type of conjoint analysis is sometimes referred to as rating-based conjoint analysis. Another type of conjoint analysis involves interviews that ask users to express their preferences by choosing between different alternatives. That type of conjoint analysis is sometimes referred to as choice-based conjoint analysis. As will be understood by someone with ordinary skill in the art, choice-based conjoint analysis may also present a user with several alternatives, and ask the user to select the "least favorite" alternative. This is sometimes referred to as a "Max-Diff" modification of choice-based conjoint analysis.

Figure 2A:
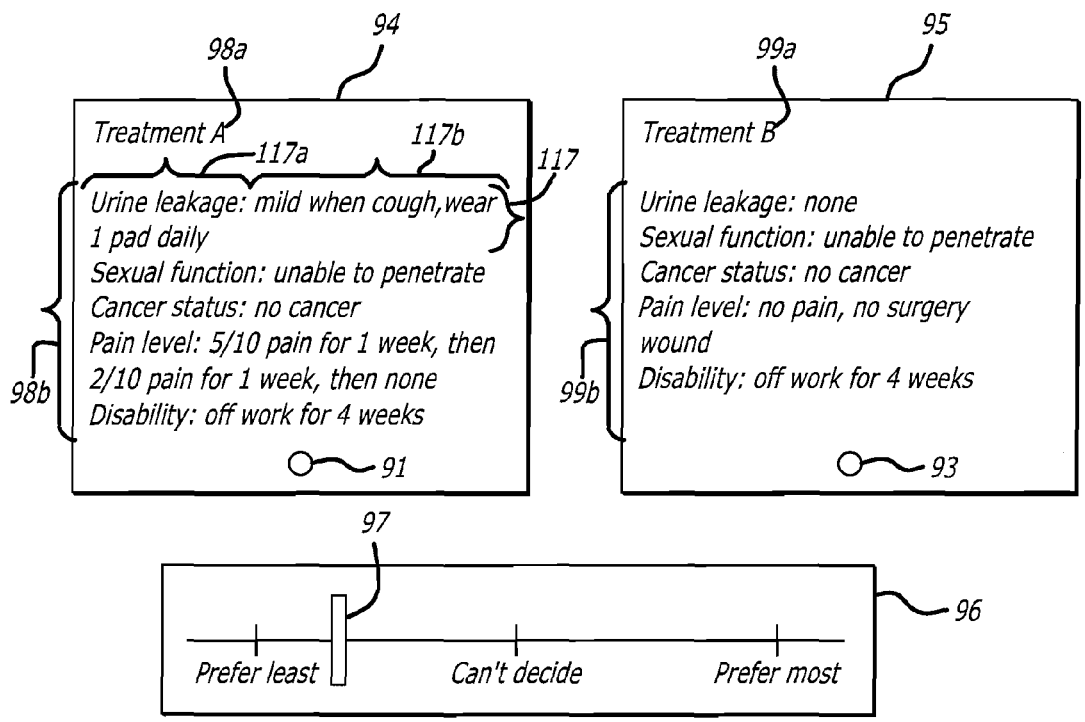
FIG. 2A depicts an exemplary rating-based medical treatment alternative selection exercise that corresponds to an exemplary patient's exemplary medical conditions and exemplary prognostic indicators in an exemplary embodiment of the present invention.

An exemplary rating-based conjoint analysis interview would present a series of medical treatment alternative selection exercises that would each present two alternative treatments. FIG. 2A depicts an exemplary rating-based medical treatment alternative selection exercise that corresponds to an exemplary patient's exemplary medical conditions and exemplary prognostic indicators. The exemplary rating-based medical treatment alternative selection exercise depicted in FIG. 2A comprises exemplary explanatory text 92a that instructs the user to select one of the two treatments displayed by clicking on the treatment to be selected (e.g., by clicking on the treatment-specific selector 91 (for Treatment A) or 93 (for Treatment B)). The exemplary explanatory text 92a further instructs the user to rate the selected treatment by using the user's cursor to drag the rating scale indicator to a position on the scale that best corresponds to the user's strength of preference for the selected treatment.

The exemplary medical treatment alternative selection exercise depicted in FIG. 2A further comprises two alternative treatment sections, depicted as boxes, for two alternative treatments A (element 94) and B (element 95). In each treatment box 94 and 95, an exemplary brief name or description of the treatment 98a and 99a is provided; and exemplary descriptions of features and attributes of the treatment and side effects 98b and 99b are also provided.

In addition to possible side effects of a treatment option, and/or possible results of a treatment option, exemplary treatment features, factors, and/or attributes may comprise, for example, costs, insurance coverage (e.g., whether or not the particular treatment option is covered by the particular patient's insurance policy), the availability of and/or quality of available medical providers (such as physicians, hospitals, and the like that may be in a certain radius of treatment for the patient).

Further, in addition to standard available treatments for a particular condition, some exemplary embodiments would present as treatment options, experimental treatments and/or clinical trial treatments and/or hypothetical treatments that would be available for the particular patient, according to the patient's medical condition and prognostic indicators. Hypothetical treatments may comprise treatments that are anticipated to be available within a particular time frame (for example, after anticipated FDA (Federal Drug Administration) approval).

Each feature, effect or attribute 117 may comprise an effect/feature/attribute name or title 117a and an effect/feature/attribute description 117b. In an exemplary rating-based embodiment such as depicted in FIG. 2A, an exemplary sliding rating scale 96 would be provided and would comprise an exemplary sliding indicator 97 that would be accessible and controllable by a user's cursor.

It will be understood by someone with ordinary skill in the art that the exemplary medical treatment alternative selection exercise depicted in FIG. 2A is exemplary and illustrative, and is not a limitation of the present invention. Other ways of collecting a user's selections between alternative medical treatments could be used without departing from the spirit of the present invention. For example, a vignette or selection exercise could present more than two alternatives.

Figure 2B:
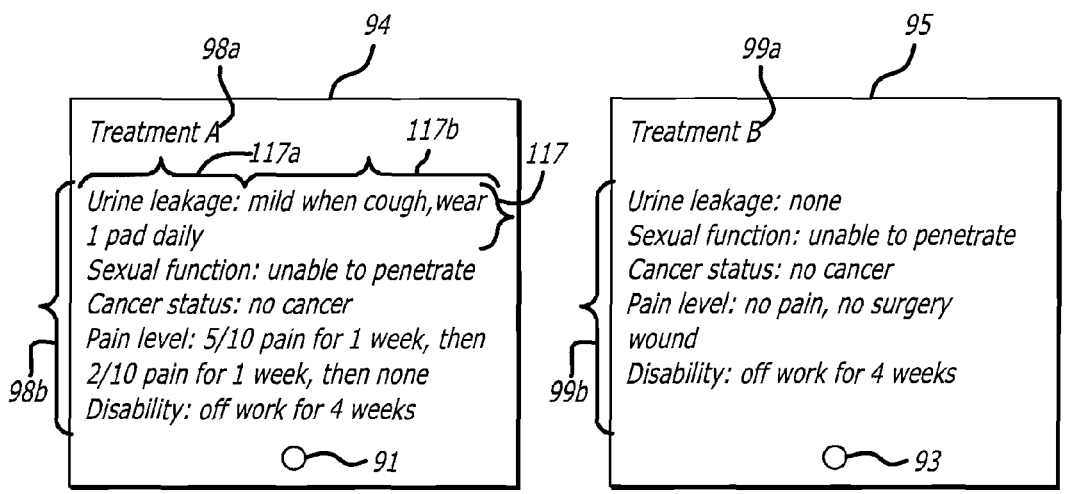
FIG. 2B depicts an exemplary choice-based medical treatment alternative selection exercise that corresponds to an exemplary patient's exemplary medical conditions and exemplary prognostic indicators in an exemplary embodiment of the present invention.

Further, as previously mentioned above, rather than presenting a sliding scale, an alternative choice-based conjoint-analysis-based embodiment could present treatment alternatives and simply ask the user to pick the most preferred treatment, such as, for example, by clicking on the preferred treatment such as depicted in FIG. 2B. FIG. 2B depicts an exemplary choice-based medical treatment alternative selection exercise that corresponds to an exemplary patient's exemplary medical conditions and exemplary prognostic indicators. The exemplary choice-based medical treatment alternative selection exercise depicted in FIG. 2B comprises exemplary explanatory text 92b that instructs the user to select one of the two treatments displayed by clicking on the treatment to be selected (e.g., by clicking on the treatment-specific selector 91 (for Treatment A) or 93 (for Treatment B)). In the exemplary embodiment, as illustratively depicted in FIG. 2B, an exemplary interactive selection exercise would present a plurality, e.g., two, medical treatment alternatives or options 98a and 99a. Each option 98a and 99a presented would comprise an indication of one or more attributes, such as, for example, effects, attributes or features associated the respective treatment option, 98b and 99b respectively. Each feature, effect or attribute 117 may comprise an effect/feature/attribute name or title 117a and an effect/feature/attribute description 117b. Each treatment option 98a and 99a and the associated effects, attributes or features, 98b and 99b respectively, would be presented in an association with a corresponding interactive selection indicator, e.g., treatment-specific selector 91 (for Treatment A) or 93 (for Treatment B). The interactive selection indicator, e.g., treatment-specific selector 91 (for Treatment A) or 93 (for Treatment B), would be configured for "clicking" or other selection by a user/patient to indicate a choice of the corresponding treatment.

One alternative embodiment will implement what is known to those with ordinary skill in the art as the Conjoint Adaptive Ranking Data System (CARDS). Such an exemplary CARDS embodiment will first examine the possible treatment attribute level combinations that derive from the possible treatment options available to the user (which are derived from the user-entered identification of the patient's medical condition and the patient's prognostic factors). For example, for a particular patient, for a particular treatment, there may be eight (8) treatment attributes, each of which have two or three levels (e.g., "incontinence" may be such an attribute with levels "none," "temporary for 3 months," and "permanent"). Such an exemplary CARDS embodiment will select combinations of attribute levels for presentation to the user.

In such an exemplary CARDS embodiment, the number of combinations that will be used will be approximately one-and-a-half (1.5) times the number of treatment attributes. Such an exemplary CARDS embodiment will generate choice-based conjoint analysis exercises using a fractional factorial design method to provide a maximally balanced and orthogonal set of possible combinations of treatment attribute levels for the patient/user to rate. The patient/user will then be presented with a choice exercise in which he/she will sequentially be presented with these possible outcomes (each displayed on a 'card' on a screen); he/she will be asked to select his/her "best choice" outcome, along with his/her second and third best. Such an exemplary CARDS embodiment will store the factorial combinations of the presented cards in a CARDS database. Each combination will represent a possible utility function. As the patient/user specifies his/her first, second and third choice, the CARDS embodiment will eliminate from the CARDS database the combinations in which those outcome "cards" are not present in the first, second and third choice order indicated by the patient/user.

At that point, such an exemplary CARDS embodiment will be able to use one of two estimation methods to describe the patient's/user's utility function: either standard logistical regression, or the more generalized multinomial logit regression. As will be understood by someone with ordinary skill in the art, multinomial logit regression is considered by some to be is more capable of handling random user error or error in response due to user fatigue as compared to standard logistical regression. In such an exemplary CARDS embodiment, multinomial logit regression will be utilized in longer preference assessment exercises. However, both estimation methods may be implemented in such an exemplary CARDS embodiment.

In an alternative exemplary embodiment, a variant of choice-based conjoint, called "Max-diff," may be implemented. The determination of preference in a Max-diff embodiment would involve a balanced, orthogonal design of treatment attribute levels similar to the above-described CARDS embodiment. However, in an exemplary Max-diff embodiment, the data collection task would comprise presenting the user with four "outcome cards" at a time. In each "task", the patient/user would be asked to select his/her "best" and "worst" card. The patient/user would then be presented with several more such tasks, depending on the number of treatment attribute levels possible for the user. The statistical modeling in such a Max-diff embodiment would use logistical regression and/or multinomial logit regression as previously described above to analyze the patient's/user's input.

Figure 3:
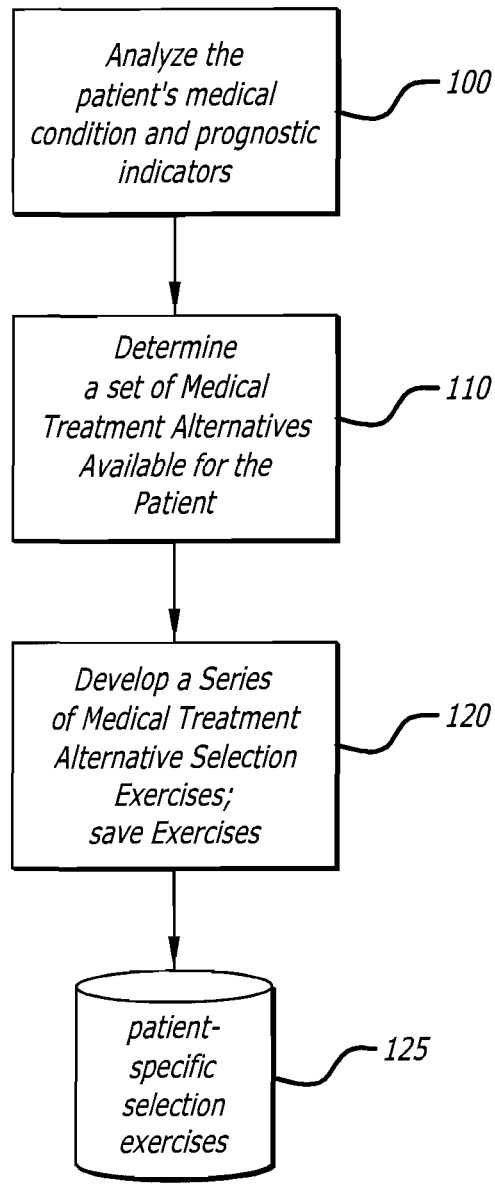
FIG. 3 is a high-level flow diagram depicting exemplary high-level logic functions of exemplary computer-implemented methods and exemplary computer system functions for developing a patient-specific interview comprising a series of medical treatment alternative selection exercises that correspond to a patient's medical condition and prognostic indicators for presentation to a user in an exemplary embodiment of the present invention.

As depicted in FIG. 1A, in the exemplary embodiment, in order to develop a pattern of a user's preferences, a series (see function elements 20, 30 and 40 in FIG. 1A) of medical treatment alternative selection (choice) exercises would be presented to a user as an interview as depicted in element 20. As depicted in FIG. 1A, in the exemplary embodiment, patient-specific medical treatment alternative selection exercises would be retrieved from a database or computer-accessible memory 125. FIG. 3 is a high-level flow diagram depicting exemplary high-level logic functions of exemplary computer-implemented methods and exemplary computer system functions for developing a patient-specific interview comprising a series of medical treatment alternative selection exercises that correspond to a patient's medical condition and prognostic indicators for presentation to a user (as depicted in element 20 of FIG. 1A).

With reference to FIG. 3, in order to develop a patient-specific interview comprising a series of patient-specific medical treatment alternative choice-based selection exercises, an exemplary embodiment would analyze the patient's medical condition and prognostic indicators as depicted in exemplary high-level function element 100. Such an exemplary embodiment would then determine a set of medical treatment alternatives that are associated with the patient's medical condition according to the patient's prognostic indicators as depicted in exemplary high-level function element 110. Such an exemplary embodiment would then develop a patient-specific interview comprising a series of medical treatment alternative selection exercises as depicted in exemplary high-level function element 120 and would save the patient-specific series of medical treatment alternative selection exercises in a computer-accessible memory or database 125.

It will be understood by someone with ordinary skill in the art that the depiction of saving a patient-specific interview series of patient-specific medical treatment alternative selection exercises is illustrative and non-limiting; in other embodiments, rather than saving an entire patient-specific interview series of exercises for retrieval, each exercise would be dynamically presented to the user as it is generated.

In yet another exemplary embodiment, rather than developing a series of medical treatment alternative selection exercises as depicted in exemplary high-level function element 120, the set of medical treatment alternatives determined in function 110 would be saved in the patient-specific medical treatment alternative database 125 for subsequent selection and presentation to the user; selections (e.g., in exemplary function element 20 in FIG. 1A) would be made of subsets of the patient-specific set of medical treatment alternatives for presentation to the user.

An exemplary way for analyzing a patient's medical condition and prognostic indicators and for determining a set of medical treatment alternatives that would be available for a particular patient would be to use decision analysis models. In the exemplary embodiment, decision analysis models would be stored as program instructions, such as, for example, as program procedures or subroutines, or would be stored as data, or as a combination of data and program instructions.

In the exemplary embodiment, a database, or other computer-accessible memory, would be provided that would comprise medical-condition-specific decision analysis model data and/or program instructions for each of a plurality of medical conditions. Each medical-condition-specific decision analysis model (comprising data and/or program instructions) would be input by an administrator and/or by a programmer. In one embodiment, a decision analysis model "wizard" would prompt an administrator to input information for a medical-condition-specific decision analysis model and would be programmed to generate and store a corresponding medical-condition-specific decision analysis model procedure and/or data.

The exemplary embodiment would provide and support three exemplary types of decision analysis models: mapping trees, decision analysis models, and combination mapping trees and decision analysis models. Exemplary decision analysis models would comprise nodes and paths; each path connects two nodes.

Figure 4:
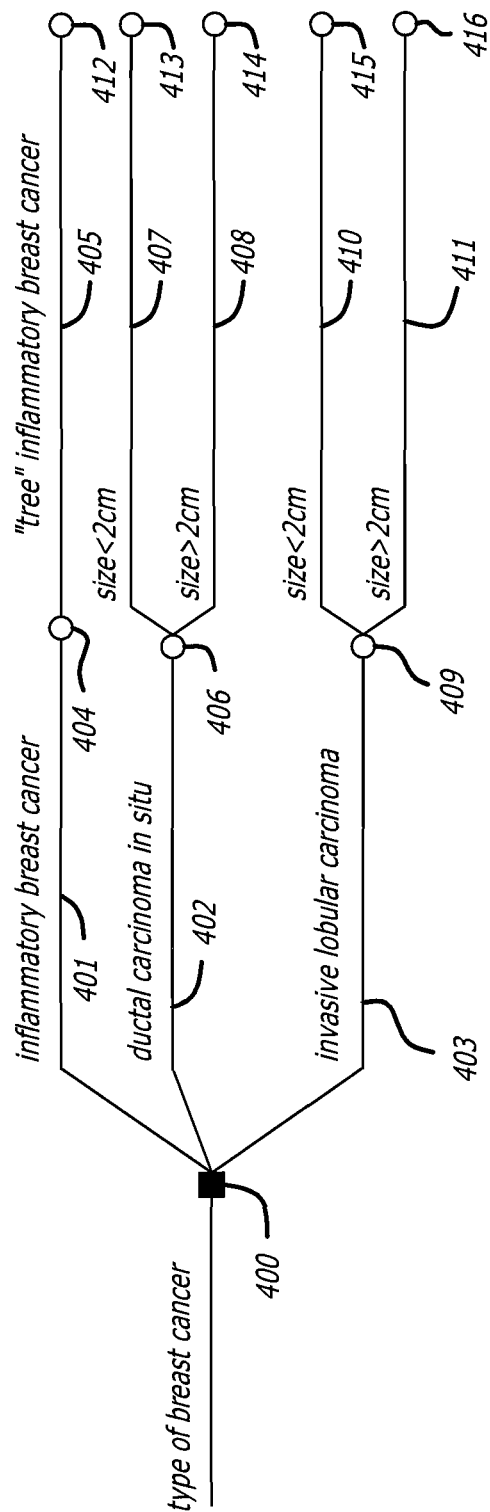
FIG. 4 depicts an exemplary mapping tree for the medical condition, breast cancer in an exemplary embodiment of the present invention.

An exemplary mapping tree maps a particular medical condition and its associated subcategories. For example, FIG. 4 depicts an exemplary mapping tree for the medical condition, breast cancer. As depicted in FIG. 4, exemplary subcategories of breast cancer include inflammatory breast cancer (exemplary path 401 from exemplary prognostic indicator node 400), ductal carcinoma in situ (exemplary path 402 from exemplary prognostic indicator node 400), and invasive lobular carcinoma (exemplary path 403 from exemplary prognostic indicator node 400). Further subcategories of breast cancer include tree inflammatory breast cancer (exemplary path 405 from exemplary prognostic indicator node 404, ending at node 412), ductal carcinoma in situ tumor size less than 2 centimeters (exemplary path 407 from exemplary prognostic indicator node 406, ending at node 413), ductal carcinoma in situ tumor size greater than 2 centimeters (exemplary path 408 from exemplary prognostic indicator node 406, ending at node 414), invasive lobular carcinoma tumor size less than 2 centimeters (exemplary path 410 from exemplary prognostic indicator node 409, ending at node 415), and invasive lobular carcinoma tumor size greater than 2 centimeters (exemplary path 411 from exemplary prognostic indicator node 409, ending at node 416).

Figure 5:
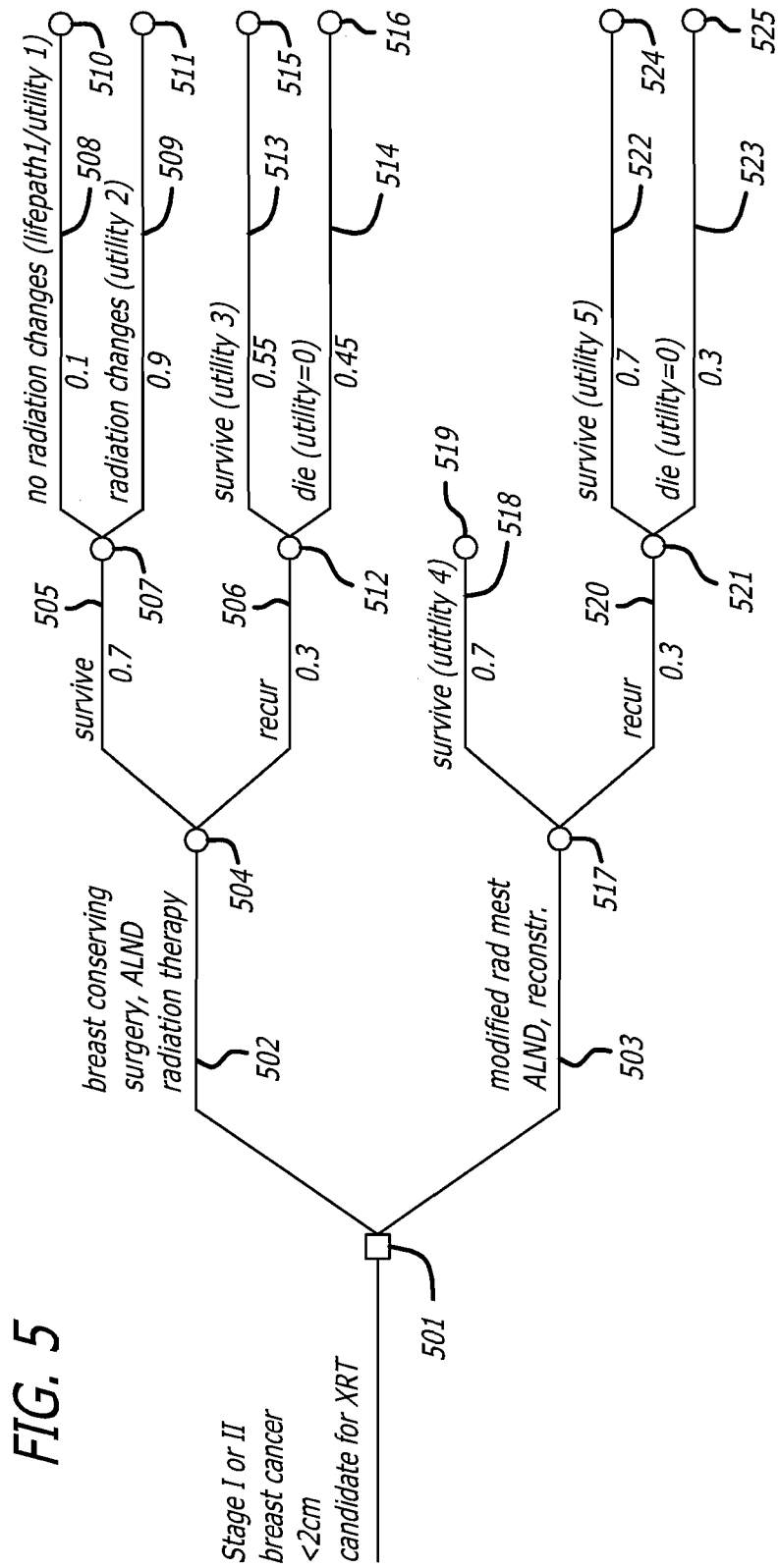
FIG. 5 depicts an exemplary decision model and further depicts exemplary decision nodes, probabilistic paths and probabilistic partial end states for each exemplary treatment alternative for Stage I or II breast cancer with a tumor size less than 2 centimeters in an exemplary embodiment of the present invention.

An exemplary decision analysis model provides decision nodes from which treatment alternatives are available. For example, FIG. 5 depicts an exemplary decision analysis model for Stage I or II breast cancer with a tumor size less than 2 centimeters. In FIG. 5, two exemplary treatment alternatives are depicted, namely, breast conserving surgery, and radiation therapy (exemplary path 502 from exemplary decision node 501), and modified radical mastectomy and reconstructive surgery (exemplary path 503 from exemplary decision node 501).

FIG. 5 further depicts exemplary decision nodes, probabilistic paths and probabilistic partial end states for each exemplary treatment alternative for Stage I or II breast cancer with a tumor size less than 2 centimeters. For example, for the exemplary breast conserving surgery and radiation therapy treatment alternative, exemplary path 505 depicts an exemplary seventy percent (70%) chance of survival from exemplary treatment option node 504 and exemplary path 506 depicts an exemplary thirty percent (30) chance of a recurrence from exemplary breast conserving surgery treatment option node 504. From exemplary survival node 507, exemplary path 508 depicts an exemplary ten percent (10%) chance of no radiation changes while exemplary path 509 depicts an exemplary ninety percent (90%) chance of radiation changes. From exemplary recurrence node 512, exemplary path 514 depicts an exemplary forty-five percent (45%) chance of dying and exemplary path 513 depicts an exemplary fifty-five percent (55%) chance of surviving.

For the exemplary modified radical mastectomy treatment alternative, exemplary path 518 depicts an exemplary seventy percent (70%) chance of survival from exemplary modified radical mastectomy treatment option node 517 and exemplary path 520 depicts an exemplary thirty percent (30) chance of a recurrence from exemplary treatment option node 517. From exemplary recurrence node 521, exemplary path 523 depicts an exemplary thirty percent (30%) chance of dying and exemplary path 522 depicts an exemplary seventy percent (70%) chance of surviving.

FIG. 5 depicts exemplary partial end state nodes 510, 511, 515, 516, 519, 524 and 525. In particular, FIG. 5 depicts the exemplary partial end states of survival after breast conserving surgery with no radiation changes (exemplary partial end state node 510), survival after breast conserving surgery with radiation changes (exemplary partial end state node 511), survival after recurrence after breast conserving surgery (exemplary partial end state node 515), death after recurrence after breast conserving surgery (exemplary partial end state node 516), survival after modified radical mastectomy (exemplary partial end state node 519), survival after recurrence after modified radical mastectomy (exemplary partial end state node 524), and death after recurrence after modified radical mastectomy (exemplary partial end state node 525).

In the exemplary embodiment, the statistical percentages that correspond to a particular path will be expressed in relation to the parent node for that path. Therefore, the sum of all of the percentages for all of the paths originating from a particular node would be 100%. It will be understood by someone with ordinary skill in the art that a user-specific chance of a particular partial end state would be calculated as a function of the percentage for each particular path that lead to that partial end state. For example, a percentage chance of the partial end state 510 (survival after breast conserving surgery with no radiation changes) could be calculated by multiplying the seventy percent (70%) chance of survival by the ten percent (10%) chance of no radiation changes, yielding a seven percent (7%) chance of that partial end state 510.

Further, it will be understood by someone with ordinary skill in the art that the sum of the percentage chances of each partial end state originating from a single node will be 100%. For example, the chance of survival after breast conserving surgery with radiation changes (for exemplary partial end state node 511) is calculated by multiplying 70% for exemplary path 505 by 90% for exemplary path 509, yielding 63%. The chances of exemplary partial end states 515 and 516 similarly calculated yield 16.5% and 13.5% respectively. The sum of the occurrence chances for all of the exemplary partial end states 510, 511, 515 and 516, all originating from the single exemplary treatment option node 504, is 100% (7%+63%+16.5%+13.5%).

In the exemplary embodiment, utility values will be calculated for each of the partial end states based on the user's/patient's selections for the various choice exercises that will be presented, and based on the exemplary analysis of those selections as described further below. The above-described occurrence chances of the partial end states for treatment effects/features/attributes will be used in calculating an "expected utility value" for a treatment as will also be described further below.

The exemplary embodiment would provide an interactive interface for input by an administrator, or alternatively, would provide for input by a systems programmer, of the aforementioned exemplary probabilistic data associated with various treatment alternatives. The aforementioned exemplary probabilistic data would be evidence-based outcome data based on treatment efficacy data and medical statistics. The exemplary embodiment would provide an exemplary administrative input interface for an administrator to input the mapping trees and decision analysis models and the evidence-based outcome data. The interactive administrative interface would facilitate the administrator input of an association of specific evidence-based outcome data with a particular outcome of a particular treatment alternative.

To provide such an administrative input interface, one exemplary embodiment of the present invention would adapt and integrate existing software, such as, by way of non-limiting example, the CBC SYSTEM by SAWTOOTH SOFTWARE of Sequim, Wash. SAWTOOTH SOFTWARE provides an interface for an administrator to input information with which to construct computer-based, choice-based conjoint interviews and further provides computer-based, interactive, choice-based conjoint interviews with a user. Another exemplary embodiment would provide custom software for providing an interface for an administrator to input information with which to construct computer-based, choice-based conjoint interviews and for further providing computer-based, interactive, choice-based conjoint interviews with a user.

It will be understood by someone with ordinary skill in the art that description herein of the use of choice-based conjoint analysis is illustrative and not a limitation of the present invention. Other methods of conjoint analysis could be used in alternative embodiments without departing from the spirit of the present invention. For example, an alternative embodiment could use a variant of choice-based conjoint analysis sometimes referred to as "Max-diff" as described further herein.

Returning with reference to FIG. 3, exemplary high-level function element 120 for generating or otherwise developing a patient-specific interview comprising a series of interactive patient-specific medical treatment alternative selection exercises would comprise examining a mapping tree/decision analysis model associated with the patient's particular medical condition, and more particularly, matching the exemplary probabilistic paths and decision nodes with each treatment alternative associated with the patient's medical condition and the patient's prognostic indicators.

Exemplary high-level function element 120 will comprise generating conjoint-analysis-based choice exercises based on exemplary treatment alternatives available to the patient, which are identified using stored information about the patient's medical condition and the patient's prognostic indicators. As described elsewhere herein, the stored patient medical condition and prognostic indicator information may have been input by the patient, one or more medical providers, through an EMR (Electronic Medical Record) system or from other users and would be stored by the exemplary embodiment.

In the exemplary embodiment, the conjoint analysis exercises will comprise a presentation of multiple, e.g., two, treatment alternatives, sometimes referred to herein as treatment options, each with a fixed number of treatment effects, factors and/or attributes. The exemplary embodiment would determine one or more decision analysis models and/or mapping trees associated with the stored information about the patient's medical condition and the patient's prognostic indicators. The exemplary embodiment would determine treatment effects, factors and/or attributes to be presented with each conjoint analysis exercise based on the decision analysis model(s) and/or mapping tree associated with the stored information about the patient's medical condition and the patient's prognostic indicators.

In one exemplary embodiment, some indication of a probability of the occurrence of a presented effect (e.g., expressed as a percentage chance) would be presented with the corresponding effect/attribute/feature. For example, a chance of occurrence of a partial end state corresponding to a particular effect/attribute/feature could be calculated such as was previously described above for presentation in correspondence with the particular effect/attribute/feature.

Figure 2C:
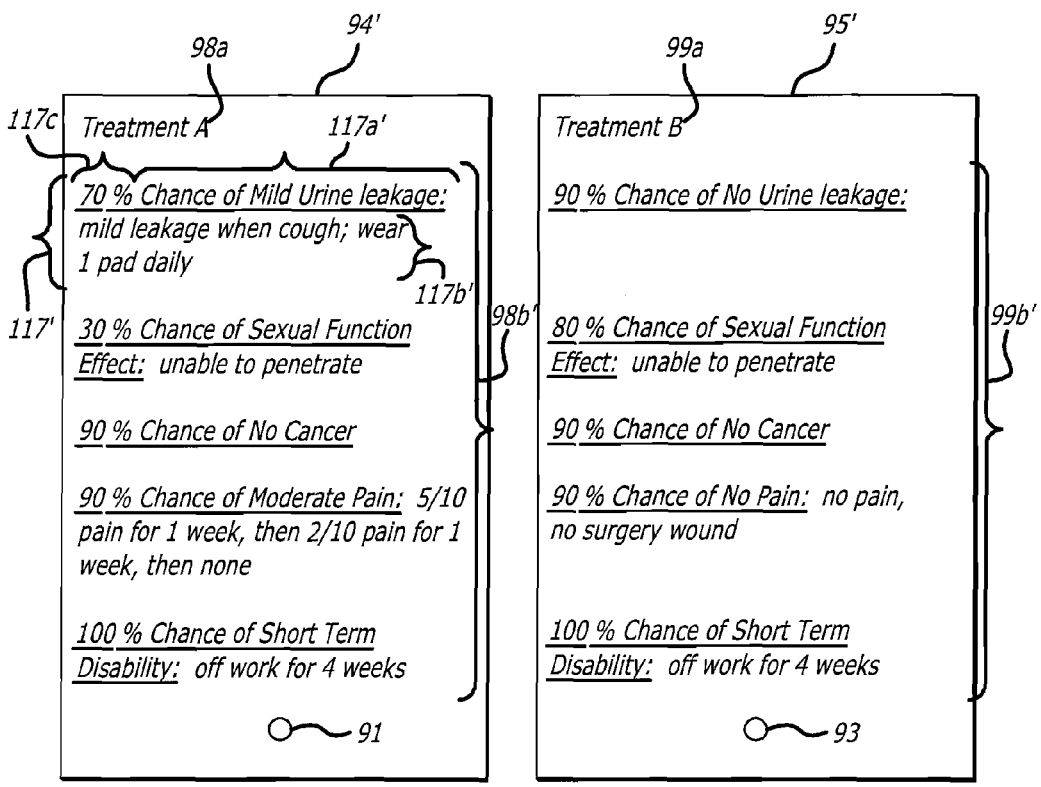
FIG. 2C depicts an exemplary choice-based medical treatment alternative selection exercise depicting probabilities associated with treatment effects, attributes and/or features/factors in an exemplary embodiment of the present invention.

FIG. 2C depicts an exemplary choice-based medical treatment alternative selection exercise depicting probabilities associated with treatment effects, attributes and/or features in an exemplary embodiment of the present invention. The exemplary choice-based medical treatment alternative selection exercise depicted in FIG. 2C comprises exemplary explanatory text 92*b* that instructs the user to select one of the two treatments displayed by clicking on the treatment to be selected (e.g., by clicking on the treatment-specific selector 91 (for Treatment A) or 93 (for Treatment B)). In the exemplary embodiment illustratively depicted in FIG. 2C, an exemplary interactive selection exercise would present a plurality, e.g., two, medical treatment alternatives or options 98*a*' and 99*a*'. Each option 98*a*' and 99*a*' presented would comprise an indication of one or more attributes, such as, for example, effects, attributes or features associated the respective treatment option, 98*b*' and 99*b*' respectively. Each treatment option 98*a*' and 99*a*' and the associated effects, attributes or features 98*b*' and 99*b*' respectively, would be presented in an association with a corresponding interactive selection indicator, e.g., treatment-specific selector 91 (for Treatment A) or 93 (for Treatment B). The interactive selection indicator, e.g., treatment-specific selector 91 (for Treatment A) or 93 (for Treatment. B), would be configured for "clicking" or other selection by a user/patient to indicate a choice of the corresponding treatment. Similar to the treatment selection exercises depicted in FIGS. 2A and 2B, in the embodiment depicted in FIG. 2C, each feature, effect or attribute 117' may comprise an effect/feature/attribute name or title 117*a*' and an effect/feature/attribute description 117*b*. As distinguished from the treatment selection exercises depicted in FIGS. 2A and 2B, in the embodiment depicted in FIG. 2C, each feature, effect or attribute 117' may further comprise a probability, illustratively depicted in FIG. 2C as a percentage 117*c*.

In other exemplary embodiments, as were previously discussed above with respect to FIGS. 2A and 2B, each effect/attribute/feature would be presented without any indication of a percentage chance of occurrence. In yet other embodiments, some effects/attributes/features for a particular treatment may be presented with chances of occurrence, while other effects/attributes/features for the treatment may be presented without any corresponding chances of occurrence.

As will be understood by someone with ordinary skill in the art, conjoint analysis interviews may present a series of exercises that are fixed, randomly generated, or a combination of fixed and randomly generated exercises. As will be understood by someone with ordinary skill in the art, for a medical condition for which there are treatment alternatives and for treatment alternatives for which there are multiple alternative effects, attributes and/or features, there may be a large number of possible combinations of the various effects, attributes and/or features of each treatment alternative that could be presented to a user.

As was discussed previously above, an exemplary decision analysis model will comprise an indication of a probabilistic percentage that is statistically associated with each particular effect/attribute/feature path. In one exemplary embodiment that presents an indication of a probabilistic percentage associated with each effect/attribute/feature, such an exemplary embodiment may present the probabilistic percentage that is statistically associated (such as may be associated in medical literature) with the particular effect/attribute/feature path.

In other exemplary embodiments that present an indication of a probabilistic percentage associated with each effect/attribute/feature, the probabilistic percentage that is presented in a treatment selection exercise may be varied as compared to the probabilistic percentage that is associated in the medical literature with the particular effect/attribute/feature path. In such an embodiment that varies the probabilistic percentage presented with each effect/attribute/feature, it will be understood by someone with ordinary skill in the art that a virtually infinite number of treatment comparisons could be constructed.

For example, in the exemplary case of the exemplary probabilistic paths and decision nodes depicted in FIG. 5 for each treatment alternative for Stage I or II breast cancer with a tumor size less than 2 centimeters, there would be a large number of possible combinations of the various effects, features and/or attributes (e.g., the various decision nodes and paths depicted as stemming from) associated with each treatment alternative for that condition. For example, the treatment alternative of breast conserving surgery could be presented with its effects of:

Survival (and depending on the embodiment, with some percentage chance of survival);

Recurrence (and depending on the embodiment, with some percentage chance of recurrence);

No radiation changes (and depending on the embodiment, with some percentage chance of no radiation changes);

Radiation changes (and depending on the embodiment, with some percentage chance of radiation changes);

death (and depending on the embodiment, with some percentage chance of subsequent death);

Survival (and depending on the embodiment, with some percentage chance of survival) and no radiation changes (and depending on the embodiment, with some percentage chance of no radiation changes);

Survival (and depending on the embodiment, with some percentage chance of survival) but with radiation changes (and depending on the embodiment, with some percentage chance of radiation changes);

Recurrence (and depending on the embodiment, with some percentage chance of recurrence), and subsequent death (and depending on the embodiment, with some percentage chance of subsequent death); or Recurrence (and depending on the embodiment, with some percentage chance of recurrence), and subsequent survival (and depending on the embodiment, with some percentage chance of subsequent survival).

The alternative treatment of modified radical mastectomy could be presented with the effects of:

Survival (and depending on the embodiment, with some percentage chance of survival);

Recurrence (and depending on the embodiment, with some percentage chance of recurrence);

Death (and depending on the embodiment, with some percentage chance of the occurrence of death);

Recurrence (and depending on the embodiment, with some percentage chance of recurrence), and subsequent death (and depending on the embodiment, with some percentage chance of subsequent death); or Recurrence (and depending on the embodiment, with some percentage chance of recurrence), and subsequent survival (and depending on the embodiment, with some percentage chance of subsequent survival).

In some exemplary embodiments, all effects, features/factors and/or attributes associated with a particular partial end state associated with a treatment would be presented with the treatment option in a selection exercise. For example, some exemplary embodiments would present, for the breast conserving surgery option depicted in FIG. 5, a conjoint analysis-based selection exercise option for breast conserving surgery that would list all effects, features and attributes associated with the partial end state node 510 (e.g., survival (and depending on the embodiment, with some percentage chance of survival) and no radiation changes (and depending on the embodiment, with some percentage chance of no radiation changes)).

In other exemplary embodiments, a subset of the effects, features/factors and attributes associated with a partial end state may be presented with the treatment option in a conjoint analysis exercise. For example, some exemplary embodiments would present, for the breast conserving surgery option depicted in FIG. 5, at least in some selection exercises, the effect/feature/attribute of survival (and depending on the embodiment, with some percentage chance of survival); in the same exercise, such an exemplary embodiment may present only the single effect/feature/attribute of death (and depending on the embodiment, with some percentage chance of the occurrence of death) with the modified radical mastectomy option. Other selection exercises presented by the same exemplary embodiment may include all of the effects, features and/or attributes associated with a treatment. It will be understood by someone with ordinary skill in the art that varying the number of effects, features and/or attributes depicted in association with a particular treatment alternative may be done to focus a user's preferences on the effects, features and/or attributes presented, resulting in additional data for analysis.

In some exemplary embodiments, in some conjoint analysis exercises, two opposing or competing treatment alternatives may be presented, such as, for example, the two alternatives of breast conserving surgery and modified radical mastectomy; in other conjoint analysis exercises, the same treatment option may be presented side by side, each presentation of the single treatment option showing different treatment effects, factors and/or attributes. For example, in such an embodiment, a single conjoint analysis exercise might present a first option of breast conserving surgery with the effects of survival and no radiation changes, and a second option of breast conserving surgery with the effects of survival with radiation changes.

As mentioned above, in some exemplary embodiments, although the percentages statistically associated with each possible effect, feature/factor or attribute will be fixed, the percentages that may be presented to users/patients with each effect, feature or attribute may be varied from the percentage obtained from medical literature in order for a user's/patient's choice of one treatment or the other to reflect the user's/patient's preference of the treatment in view of the presented associated risk factor(s).

Further, it will be understood by someone with ordinary skill in the art that the mapping trees and decision analysis models depicted in the Figures of the present application are exemplary and illustrative and are not a limitation of the invention. Rather, a decision analysis model for a particular medical condition, such as Stage I or II breast cancer with a tumor size less than 2 centimeters, for example, could include a number of additional effects, attributes and/or features as compared to those depicted in FIG. 5, and corresponding probabilistic percentages. For example, a more detailed decision analysis model for Stage I or II breast cancer with a tumor size less than 2 centimeters could include, but not be limited to including, for example, additional nodes and paths corresponding to pain levels, disability factors (e.g., time off work), complications (e.g., infection), and the like.

In view of the above-outlined possible combinations of effects, attributes or features, and in some embodiments, the above-mentioned varying of percentages for presentation to the user/patient, it will be understood by someone with ordinary skill in the art that a virtually infinite number of choice exercises could be constructed. However, in the exemplary embodiment, a limited number of choice exercises will be generated for each user/patient.

As mentioned above, the exemplary embodiment will generate a fixed number of choice exercises for a particular exemplary medical condition, but will present the user with a random selection of these exercises, except if the system administrator mandates certain choice exercises or if the user is re-entering the exemplary system to perform post-sensitivity exercises as will be described further below, or if the user is re-entering the exemplary system after an interruption.

In the exemplary embodiment, once a selection of exercises is made by the exemplary system, the exemplary embodiment would save in a computer-accessible memory storage, the selection of exercises to be presented to the user (as depicted in FIG. 3, function 120 would save the exercises on exemplary computer-accessible memory storage 125). Also, as a user completes a particular exercise, the exemplary embodiment would mark the exercise as complete in the computer-accessible memory storage. Then, in the event that a user's session is interrupted, e.g., the user is disconnected, or signs-out or logs off of the system, when the user re-enters (such as re-connecting, or otherwise signing in to the exemplary system), the exemplary embodiment would retrieve the selection of exercises for the particular user and would start the session at the next as-yet-uncompleted exercise.

It will be understood by someone with ordinary skill in the art that generating a fixed number of choice exercises for a particular medical condition is not a limitation of the present invention. Rather, in some exemplary embodiments, the number of choice exercises presented to a particular user/patient may depend on the corresponding prognostic indicators.

In an exemplary embodiment that varies and presents probabilistic occurrence percentages with each effect, a fixed number of choice exercises for a particular exemplary medical condition will be generated, and the percentages presented with each effect may be randomly generated as well.

Depending on the number of treatments and associated effects, attributes and/or features/factors, the total number of exercises that may be developed to compare each possible combination of the effects of the various available treatments might be overwhelming to a user. It will be further understood by someone with ordinary skill in the art that conjoint-analysis-based interviews may be more effective when the number of exercises presented to a user does not overwhelm the user. Therefore, in the exemplary embodiment, depending on the number of treatments and associated effects, attributes and/or features/factors, only a subset of the total possible choice exercises that may be generated may be actually presented in a user interview. In the exemplary embodiment, an exemplary interview will comprise a plurality of choice exercises such that each effect associated with each treatment is presented at least one time to the user/patient. In the exemplary embodiment, choice exercises will be randomly generated and a fixed number of choice exercises will be selected from those generated and presented to each user/patient. In other embodiments, a fixed number of exercises would be randomly generated and presented to a user.

In one exemplary embodiment, each choice exercise would comprise a fixed number of medical treatment alternatives and a fixed number of effects and/or conditions associated with each medical treatment alternative.

It will be understood by someone with ordinary skill in the art that the above-outlined manner of presenting choice exercises is exemplary and illustrative and not a limitation of the present invention. For example, in other exemplary embodiments, the number of effects/conditions associated with each treatment in a single choice exercise will be equal, however, the number of effects/conditions presented from one choice exercise to another may vary.

Returning with reference to FIG. 1A, from the exemplary computer-accessible memory/database 125 of patient-specific medical treatment alternative selection exercises, the exemplary embodiment would then select a medical treatment alternative selection exercise and would present the selected exercise to the user as depicted in exemplary high-level function element 20.

In the exemplary embodiment, patient-specific medical treatment alternative selection exercises may be presented as an online textual and graphical display, as an audio/video presentation, and/or as a combination. In the exemplary embodiment, each selection exercise would be presented as an exemplary interactive selection exercise of medical treatment alternatives, such as, for example, as illustratively depicted in FIGS. 2B and 2C as previously discussed above.

Continuing with reference to FIG. 1A, as depicted in exemplary function 30, the exemplary embodiment would receive a user's selection of a treatment alternative (and in some embodiments, a user expression of preference strength, such as a rating) and would save the user selections and/or ratings in a computer accessible memory, such as a user preference/rating database 35.

Then, as depicted in exemplary test function 40, the exemplary embodiment would determine if there were more exercises remaining in the user interview, or that should be presented in the user interview. If there were more exercises remaining in the user interview or that should be presented in the user interview, e.g., the exemplary "Y" (yes) path 41, then the exemplary embodiment would again perform the exemplary function 20 to select and present a further medical treatment alternative selection/rating exercise comprising medical treatment alternatives and associated attributes, effects and/or features (and in some embodiments, an attribute/effect/feature level, such as a percentage of occurrence).

Once all treatment selection exercises for a particular interview have been presented to a user and the user has made corresponding selections, i.e., the exemplary "N" (no) path 42 depicted in FIG. 1A, then as depicted in exemplary function 50, the exemplary embodiment will be programmed to determine a pattern of the user's choices according to the user's selections as were recorded in the computer accessible memory such as the user preference/rating database 35.

In determining a pattern of the user's choices, the exemplary embodiment will use conjoint analysis. The mathematics of conjoint analysis are known to someone with ordinary skill in the art. However, conjoint analysis is often used to determine patterns of choices by a population of users; whereas the exemplary embodiment will use conjoint analysis to determine a pattern of a single user's choices. Because the mathematics of conjoint analysis are known to someone with ordinary skill in the art, only an overview is described below.

In particular, in the exemplary embodiment, data regarding the selections made by a particular user will be analyzed using multinomial logit regression techniques to define the user's preferences. The exemplary embodiment would provide an administrative user interface for identifying main effects/features/attributes and also, in some embodiments, for identifying interactions to be included in each logit analysis.

As depicted in exemplary function 60 in FIG. 1A, for main effects/features/attributes, the exemplary embodiment would calculate a "utility" value for each effect/feature/attribute using multinomial logit regression techniques. For interactions, in some exemplary embodiments, "utility" values would also be calculated for combinations of effects/features/attributes.

As will be understood by someone with ordinary skill in the art, logit analysis is an iterative process for finding a maximum likelihood solution for fitting a multinomial logit model to the corresponding data. In the exemplary embodiment, for each iteration, a log-likelihood and a root-likelihood would be determined. As will be understood by someone with ordinary skill in the art, a root-likelihood is a measure of fit of the model to the corresponding data.

The exemplary embodiment would perform a plurality of iterations of the logit analysis until determining that the iterations had converged.

The exemplary embodiment would evaluate the logit analysis results according to "Chi Square" statistics. In particular, the exemplary embodiment would determine a log-likelihood that would be obtained, given the treatment selection exercises that were presented to the user, if the estimated effects were all zero (referred to hereinbelow as the "zero-based log-likelihood") as compared to the aforementioned log-likelihood that was calculated from the final iteration of logit analysis (referred to hereinbelow as the "iteratively-calculated log-likelihood"). Then, the exemplary embodiment would calculate a difference between the zero-based log-likelihood and the iteratively-calculated log-likelihood. The exemplary embodiment would calculate the Chi Square for the particular case by multiplying the difference by two. In the exemplary embodiment, the calculated Chi Square would be associated with degrees of freedom equal to the number of parameters estimated. In the exemplary embodiment, the number of parameters would comprise the total number of levels (Treatment Alternatives/Options) that had been presented in the selection exercises to the user, minus the number of effects/features/attributes. For example, a particular patient with a particular medical condition may have two (2) Treatment Options available; each Treatment Option may have a total of six (6) associated effects/features/attributes. In an exemplary patient interview in an exemplary embodiment, the two Treatment Options may be presented in ten (10) selection exercises to the patient, each exercise showing with varying levels of the associated effects/features/attributes with each of the two Treatment Options. In total, the ten (10) selection exercises would then present an exemplary total number of twenty (20) Treatment Options. The exemplary number of parameters for such an exemplary patient interview would therefore comprise twenty (20) Treatment Options minus six (6) associated effects/features/attributes, totaling fourteen (14) parameters.

As depicted in exemplary function 70 in FIG. 1A, the exemplary embodiment would use the utility value for each effect/feature/attribute of a particular treatment to calculate a utility value for the particular treatment. In particular, for a case where there are no interactions identified, the exemplary embodiment would calculate an expected utility value for a particular treatment by calculating the probability of occurrence of each particular effect/attribute/feature (i.e., by calculating the chance of occurrence of the particular partial end state as was previously described above) and by then multiplying that calculated probability of occurrence by the utility value for the particular effect/attribute/feature; the exemplary embodiment would then sum all of the results for all of the effects/attributes/features for the particular treatment, resulting in an expected utility value for the particular treatment according to the particular user's selections.

As depicted in exemplary function 80 in FIG. 1A, the exemplary embodiment will then calculate a respective ranking of each medical treatment alternative available for the user, according to the specified medical condition and prognostic indicators. In particular, the exemplary embodiment would sort the respective treatment alternatives available for the user according to their respective expected utility values. Once sorted, the exemplary embodiment would assign a relative ranking to each respective treatment alternative available for the user.

Then, as depicted in exemplary function 90, the exemplary embodiment would present one or more recommendations of a medical treatment approach according to the respective ranking of each medical treatment alternative available for the user.

Sensitivity Analysis.

In presenting recommendations, one exemplary embodiment will present the user with a rank-ordered list of treatment options. For each treatment option, such an exemplary embodiment will systematically vary the utilities assigned to each potential partial end state, from 0.0 to 1.0, holding all other probabilities and utilities stable. Using each new utility value for the partial end state, such an exemplary embodiment will calculate the expected utility for each of the treatment options being evaluated as described previously above. Such an exemplary embodiment will determine if the rank order of the treatment option in question would change if the utility in question was raised or lowered by any amount, and report that to the user as described further below. Such an exemplary embodiment will do this sensitivity analysis for each utility for each partial end state. Depending on the particular circumstances, some rankings may not be sensitive to the utility for particular end states, while others will. Such an exemplary embodiment will thus make the user aware of treatment attributes, effects and features/factors where patient preferences play a key role in determining best care, so that the patient may have a more focused discussion with their physician.

In particular, after a patient or other user completes the series of choice-based conjoint analysis selection exercises that would be presented by such an exemplary embodiment, such an exemplary embodiment would present with the aforementioned rank-ordered list of treatment option recommendations, an indication of how the patient's/user's choices effected each recommendation and/or an indication of how, if the patient's/user's choices had been different, an alternative treatment recommendation might be more appropriate, or more highly ranked. For example, the exemplary embodiment might indicate to a patient/user, that the patient's/user's choices indicated a sensitivity to a particular side effect, such as, for example, changes with radiation treatment. The system's analysis of how a patient's/user's choices effected a medical treatment recommendation may sometimes be referred to herein as "sensitivity analysis."

After presenting a patient/user with such rank-ordered medical treatment recommendations and with the above-described sensitivity analysis of the patient's/user's choices, the exemplary embodiment would provide the patient/user with an opportunity to re-take the series of choice-based conjoint analysis selection exercises. Such an opportunity to re-take the exercises would allow the patient/user to rethink his/her sensitivity to certain aspects (effects, attributes, and/or features/factors) of the available treatment options.

As was mentioned above, in some exemplary embodiments, selection exercises may be randomly selected for initial presentation to a particular patient/user. However, in the event that the patient/user chooses to retake the exercises in view of the above-described sensitivity analysis, the exemplary embodiment will replicate (most or all of) the series of exercises for the retake that were initially presented to the patient/user. In particular, the exemplary embodiment would retrieve from a computer-accessible memory storage (e.g., element 125 as depicted in FIG. 1A), the selection exercises that had previously been presented to the user and would re-present them to the user. As the user re-takes each exercise in the series, the exemplary embodiment would indicate in the computer-accessible memory storage that the user had again completed the exercise (as depicted, e.g., in element 30 of FIG. 1A).

In other embodiments, however, different selection exercises may be presented during the re-take session than were initially presented to the user in order to focus the user's analysis of the user's sensitivity to certain aspects of available treatment options.

Once the user has completed retaking the series of selection exercises, the exemplary embodiment would repeat steps substantially similar to the exemplary functions 50-90 depicted in FIG. 1A to determine and present to the user a further rank-ordered list of treatment option recommendations considering the results of the user's retaking the exercises.

Exemplary Embodiment System Implementation.

The exemplary embodiment would be implemented according to an Internet-based client-server model. Someone with ordinary skill in the art will understand that the exemplary Internet-based, client-server implementation is exemplary and illustrative and is not a limitation of the present invention. Rather, other exemplary embodiments could be implemented using a closed environment, such as, for example, a Local Area Network, without departing from the spirit of the present invention. Further, some embodiments may generate paper-based interviews; user selections could later be input into a computer-based system embodiment of the present invention.

Figure 6:
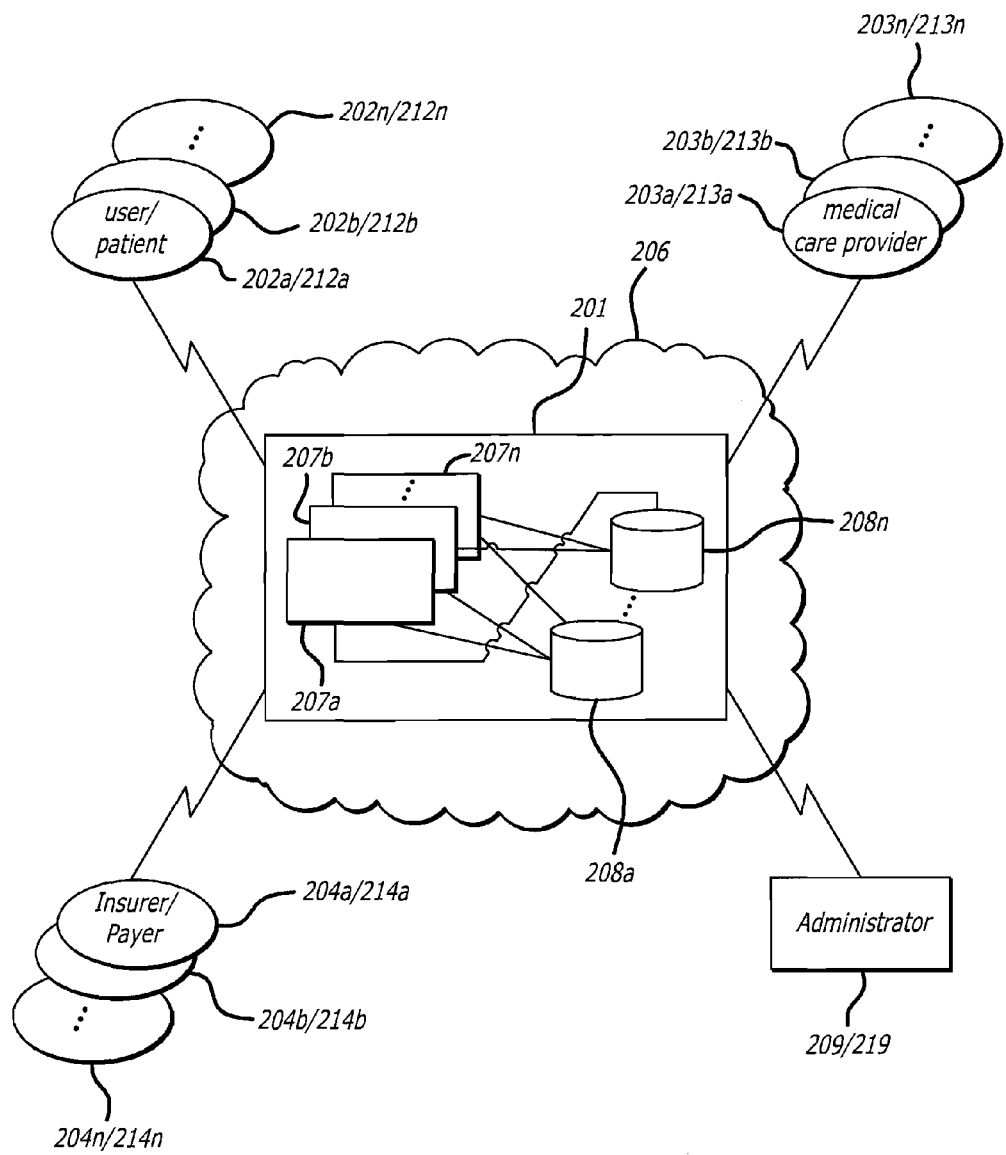
FIG. 6 is a high level exemplary entity relationship diagram depicting exemplary interface relationships that would be provided by an exemplary Internet-based embodiment system in an exemplary embodiment of the present invention.

FIG. 6 is a high level exemplary entity relationship diagram depicting exemplary interface relationships that would be provided by an exemplary Internet-based embodiment system 201 between a plurality of exemplary users/patients 202a-202n, a plurality of exemplary medical care providers 203a-203n, a plurality of exemplary insurers/payers 204a-204n, and an exemplary Administrator 209 over the Internet 206.

Suffixes such as "a" through "n" in connection with numbered elements of the FIGURES herein are exemplary and are not limitations; such suffixes may be used to denote an unknown, unlimited number of similar elements.

In the exemplary embodiment, as depicted in FIG. 6, one or more exemplary server computers 207a-207n (sometimes referred to herein simply as the "server," or "servers,") would be programmed to provide the features described herein. Exemplary server computers 207a-207n would have access to exemplary computer-accessible memory 208a-208n.

It will be understood by someone with ordinary skill in the art that the present invention is not limited to implementation on server computers, but rather, may be implemented using computer devices of various types, whether now known or in the future discovered.

In the exemplary embodiment, exemplary client computers 212a-212n will be used by respective users/patients 202a-202n; exemplary client computers 213a-213n will be used by exemplary medical care providers 203a-203n, exemplary client computers 214a-214n will be used by exemplary insurers/payers 204a-204n, and exemplary client computer 219 will be used by exemplary Administrator 209, to access the exemplary embodiment servers 207a-207n. Exemplary client computers 212a-212n, 213a-213n, 214a-214n, and 219 would comprise, for example, web browser software, or other software, whether now known or in the future discovered, that is configured to render hypermedia content over a closed network or a global communications network to the respective client computer executing the web browser or other software, such global communications networks including but not limited to the Internet.

The above-provided description of an exemplary Internet-based, or global communications network-based embodiment, is illustrative and not a limitation of the present invention. Rather, various exemplary embodiments could be implemented, for example, using Local Area Networks, Wide Area Networks, or other networking configurations, or could be implemented on a personal computer or other computer device for use by one or more users.

Returning with reference to FIG. 6, using such web browser or other software, exemplary users/patients 202a-202n, exemplary medical care providers 203a-203n, exemplary insurers/payers 204a-204n, and exemplary Administrator 209 would use exemplary client computers 212a-212n, 213a-213n, 214a-214n, and 219 respectively to access the exemplary embodiment system 201 and the corresponding exemplary embodiment servers 207a-207n.

Figure 7:
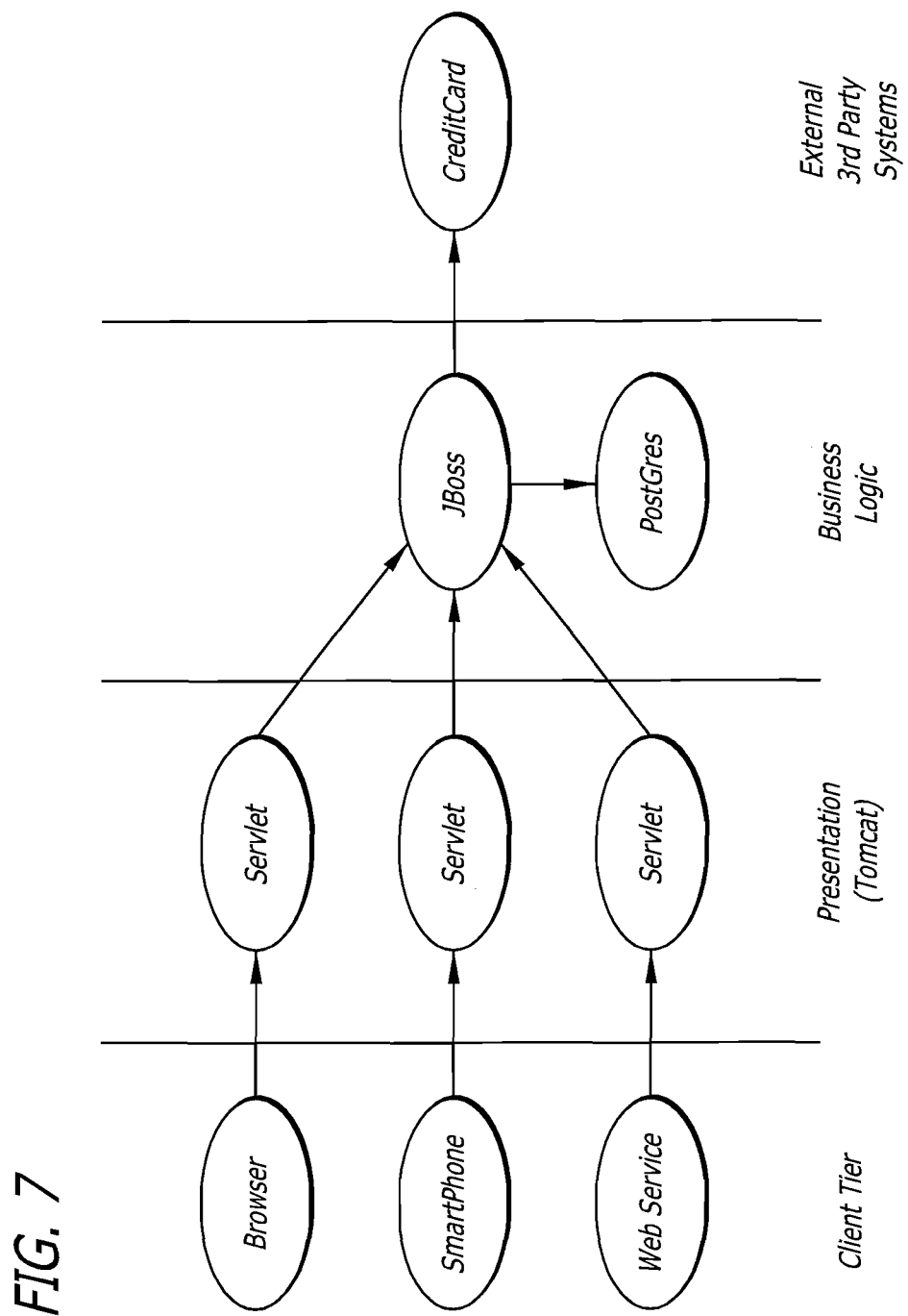
FIG. 7 is a high level diagram depicting exemplary system components in an exemplary embodiment of the present invention.

The exemplary embodiment of the present invention would comprise an exemplary three-tier architecture, using various software, programming, hardware, database and data access technologies, such as described further below. FIG. 7 is a high level diagram depicting exemplary system components.

An exemplary back-end tier may comprise, for example:
1) apache httpd;
2) ssh server (access via apache);
3) tiki wiki (access via apache);
4) JBoss/Tomcat;
5) PostGreSQL-Database;
6) Perl scripts for conjoint-related calls to the database An exemplary front-end tier may comprise, for example:
1) HTMUCSS/JS, aka
2) AJAX
3) Spring MVC (or Struts)

An exemplary Server-tier may comprise, for example:
1) Xeon 5100 Dual-Core "Woodcrest" (2 cores)
2) 2 GB RAM
3) Cent OS Linux (64 bit)
4) Hardware RAID 1
5) 2×250 GB SATA Hard-Drive
6) 60 GB Backup service
7) Shared Fire Wall As will be understood by someone with ordinary skill in the art, exemplary use of the above-mentioned software, programming, hardware, database and/or data access technologies is illustrative and non-limiting. Other software and/or programming and/or hardware and/or database and/or data access technologies, whether now known or in the future discovered, could be used without departing from the spirit of the present invention. For example, another exemplary embodiment could be developed as a JAVA web-based application using open source software and using, among others, the following technologies:

LINUX-UBUNTU (e.g., 11.04)
JAVA (e.g., 6)
APACHE STRUTS (e.g., 2.1.2)
MYBATIS Data Access Framework (e.g., 3.0)
MYSQL Relational Database (e.g., 5.5)
APACHE TOMCAT (e.g., 7)
SPARE INTELLIGENCE ENGINE (e.g., 3.1)
HTML
ADOBE FLASH/ADOBE FLASH PLAYER Exemplary Internet-Based Embodiment.

Some exemplary embodiments would provide a computer system, such as an Internet-based computer system, for dynamically generating real-time online medical treatment decision support regarding a patient's medical condition. In an exemplary Internet-based embodiment, the exemplary computer system would comprise at least one computer device, such as an exemplary server computer, that would be programmed to collect user input from a user, such as could be input by a user through a client computer accessing the exemplary server computer over an Internet connection.

One exemplary Internet-based embodiment would use conjoint analysis to analyze a user's/patient's choices and preferences regarding medical treatment attributes and treatment outcomes for medical treatments that would be available for a particular patient, according to risk-based outcomes based on probabilistic information associated with such outcomes, and in view of a particular patient's medical condition and prognostic indicators. One exemplary Internet-based embodiment would adapt one or more of an ASEMAP, FPM, or Choice-Based (or other conjoint analysis methodologies, whether now known or in the future discovered) approach for conjoint analysis and related existing software (e.g., ASEMAP, FASTPACE, CBC SYSTEM or other software, whether now known or in the future discovered). Alternatively, or in combination, an exemplary Internet-based embodiment would use exemplary custom Internet-based conjoint analysis software as described further below for conjoint analysis of an individual patient's preferences.

It will be understood by someone with ordinary skill in the art that the description herein of an exemplary Internet-based embodiment is illustrative and exemplary and is not a limitation of the present invention. Rather, the below-described embodiment could be implemented in other processing environments without departing from the spirit of the invention. By way of non-limiting example, the below-described embodiment could be implemented on a wide-area network, a local area network, on a single computer, or in other processing environments, whether now known or in the future discovered.

Figure 1B:
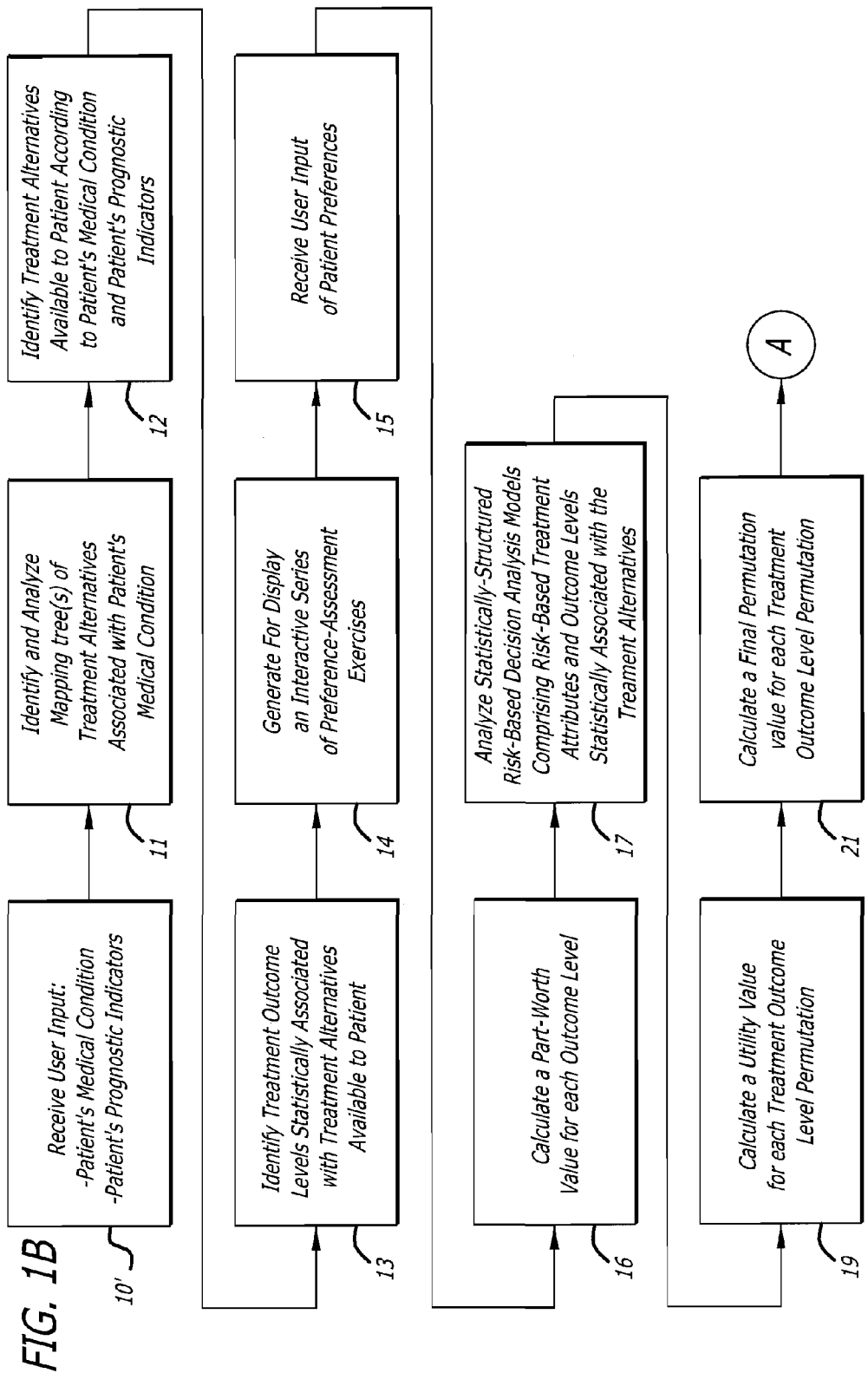
FIGS. 1B and 1C are a high-level flow diagram depicting exemplary high-level logic functions of exemplary computer-implemented methods and exemplary computer system functions for dynamically generating and presenting patient preference-assessment exercises and performing real-time conjoint analysis of patient preferences to rank medical treatment alternatives in an exemplary real-time, Internet-based, conjoint-analysis-based embodiment of the present invention.
Figure 1C:
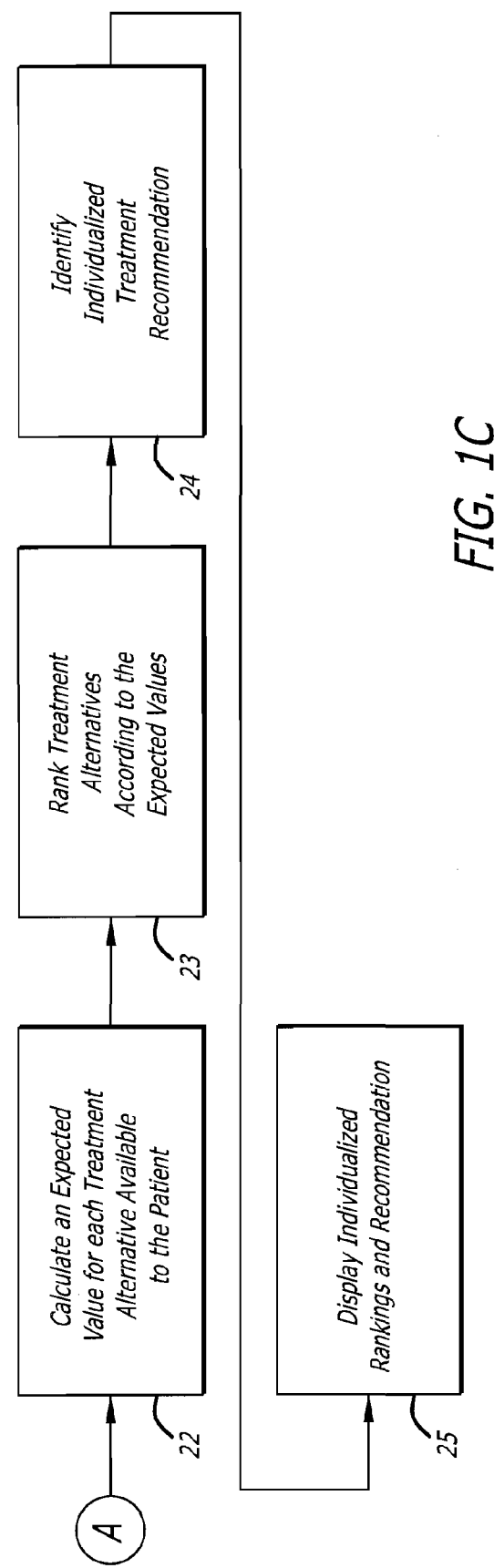

FIGS. 1B and 1C are a high-level flow diagram depicting exemplary high-level logic functions of exemplary computer-implemented methods and exemplary computer system functions for dynamically generating and presenting patient preference-assessment exercises and performing real-time conjoint analysis of patient preferences to rank medical treatment alternatives in an exemplary real-time, Internet-based, conjoint-analysis-based embodiment of the present invention.

As depicted in FIGS. 1B and 1C, one exemplary Internet-based embodiment would comprise an exemplary server computer (not shown) that would be programmed (whether alone or in conjunction with one or more other computer devices) to receive 10' user input, such as through a user's client computer, of a patient medical condition and prognostic indicators regarding the patient. As further depicted in FIGS. 1B and 1C, in response to receiving said user input of the patient medical condition and prognostic indicators regarding the patient, the exemplary server computer (whether alone or in conjunction with one or more other computer devices) would be programmed to identify and analyze 11 one or more mapping trees of treatment alternatives associated with a patient's medical condition and identify 12 treatment alternatives that would be available to the particular patient according to the patient's medical condition and according to the prognostic indicators associated with the patient; the exemplary server computer (whether alone or in conjunction with one or more other computer devices) would be further programmed to identify 13 treatment attributes and outcome levels that are statistically associated with said treatment alternatives; the exemplary server computer (whether alone or in conjunction with one or more other computer devices) would be further programmed to generate 14 for display, such as to a display device in communication with the user's client computer, an interactive series (e.g., a set) of preference-assessment exercises; in one exemplary Internet-based embodiment, each preference-assessment exercise would comprise a set of alternative medical treatments, and corresponding risk-based treatment outcome levels and would further comprise an interactive prompt for user input of an expression of patient preference regarding the set of alternative medical treatments.

In such an exemplary Internet-based embodiment, the exemplary server computer (whether alone or in conjunction with one or more other computer devices) would be further programmed to receive 15 user input of an expression of patient preference regarding the set of alternative medical treatments, and to perform conjoint analysis (involving high-level function identified by element number 16, and additionally involving the above-mentioned functions of generating preference-assessment exercises 14 and receiving user input 15 as those functions are described in more detail below) to analyze said user input with respect to said risk-based treatment outcome levels. In particular, as depicted in FIGS. 1B and 1C, the exemplary server computer (whether alone or in conjunction with one or more other computer devices) would be further programmed to calculate 16 a part-worth value for each outcome level as described further below. The exemplary server computer (whether alone or in conjunction with one or more other computer devices) would be further programmed to, and as described further below, to use the results of the above-mentioned conjoint analysis to analyze 17 statistically-structured, risk-based decision analysis models comprising risk-based treatment attributes and outcome levels statistically associated with the treatment alternatives; calculate 19 a utility value for each treatment outcome level permutation; calculate 21a final permutation value for each treatment outcome level permutation; and calculate 22 an expected value for each treatment alternative available to the patient. The exemplary server computer (whether alone or in conjunction with one or more other computer devices) would be further programmed to use the aforementioned calculated expected value for each of the treatment alternatives available for the patient, to rank 23 said treatment alternatives, to identify 24 a treatment recommendation, and to display 25 said rank and said recommendation of said treatment alternatives to the user. The above-described high-level functions are described in more detail below in connection with an illustrative prostate-cancer module.

In one exemplary Internet-based embodiment, a condition-specific module would be provided for each condition (disease, illness, etc.); each condition-specific module would comprise condition-specific criteria and calculations. Each condition-specific module would provide a set of stratifying questions to gather participant (whether a patient or other user) data regarding the patient's prognostic indicators. Then, based on a participant's responses to the set of stratifying questions, the condition-specific module would construct and generate for display (such as, for example, in an exemplary Internet-based embodiment, to a display device in communication with a user's client computer device) a participant preference-assessment "interview" comprising a series of interactive participant preference-assessment exercises.

In one such exemplary Internet-based embodiment, "partial profiles" will be used as compared to "full profiles." A "full profile" would comprise a treatment alternative showing all of the attributes for the treatment alternative. A "partial profile" would present a selection of possible attributes, such as a pre-determined number of possible attributes, for each treatment alternative. In one such exemplary Internet-based embodiment, instead of including all attributes for each treatment alternative in a "full profile" paired comparison of two treatment alternatives, a participant preference-assessment "interview" would comprise a series of a predetermined number of paired two-outcome-level and three-outcome-level "partial profiles." An exemplary generation (see, e.g., element 14 in FIGS. 1B and 1C) of partial profile conjoint-analysis-based preference-assessment exercises and other corresponding conjoint analysis functions (see, e.g., elements 15 and 16 in FIGS. 1B and 1C) are illustratively described below with respect to an exemplary prostate-cancer module.

For one exemplary prostate-cancer module, four (4) exemplary treatment options, or alternatives, would be provided, comprising, for example, Active Surveillance, Brachytherapy, Radiation Therapy and Surgery.

One such exemplary Internet-based embodiment would provide for each condition-specific module, a user-manageable set of treatment outcomes (i.e., attributes that may be associated with each treatment option) with a variable number of outcome levels (i.e., attribute levels) for potential presentation to a user in association with various treatment alternatives. For example, an exemplary prostate-cancer module would provide exemplary prostate-cancer-treatment outcomes (i.e., attributes) regarding Sexual Function, Urinary Function, Bowel Function, a first aspect of Invasiveness, a second aspect of Invasiveness, Recovery Time, possible Complications, the possibility of a Transfusion, and Survivability.

For such an exemplary prostate-cancer module, the exemplary prostate-cancer-treatment outcome regarding sexual function could provide exemplary levels ranging from no change, to temporarily much worse with full recovery at 12 months, to a slow decline over two years to much worse with no recovery, to much worse with no recovery. For such an exemplary prostate-cancer module, the exemplary prostate-cancer-treatment outcome regarding urinary function could provide exemplary levels ranging from no change, to temporary leakage with cough or strain with full recovery at 6 months, to leakage with cough or strain with no recovery. For such an exemplary prostate-cancer module, the exemplary prostate-cancer-treatment outcome regarding bowel function could provide exemplary levels ranging from no change, to temporary rectal urgency/frequency with full recovery at 6 months, to rectal urgency/frequency with no recovery. For such an exemplary prostate-cancer module, the exemplary prostate-cancer-treatment outcome regarding a first aspect of invasiveness could provide exemplary levels ranging from non-invasive to general anesthesia with a surgical incision into the abdomen. For such an exemplary prostate-cancer module, the exemplary prostate-cancer-treatment outcome regarding a second aspect of invasiveness could provide exemplary levels ranging from non-invasive to general anesthesia, using long needles to place radioactive seeds into the prostate. For such an exemplary prostate-cancer module, the exemplary prostate-cancer-treatment outcome regarding recovery time could provide exemplary levels ranging from immediate to two days to 4 weeks with a urinary catheter for two weeks. For such an exemplary prostate-cancer module, the exemplary prostate-cancer-treatment outcome regarding possible complications could provide exemplary levels ranging from none to a blood clot in the leg requiring long term medical therapy. For such an exemplary prostate-cancer module, the exemplary prostate-cancer-treatment outcome regarding the possibility of transfusion could provide exemplary levels ranging from not needed to needed. And for such an exemplary prostate-cancer module, the exemplary prostate-cancer-treatment outcome regarding survivability could provide exemplary levels ranging from no change to six months shorter lifespan to twelve months shorter expected lifespan.

One such exemplary Internet-based embodiment would provide an exemplary statistically-structured, risk-based decision analysis "model" for each treatment option; an exemplary statistically-structured, risk-based decision analysis "model" for a treatment option would comprise a probability value associated with each outcome level associated with the treatment option; each outcome level probability value associated with the treatment option could be either a constant, a probability value derived from a lookup table, or a probability value that is calculated using a predefined algorithm according to the user's answers to one or more stratifying questions.

In one such exemplary Internet-based embodiment, as part of setting the stage for conjoint analysis and for generating conjoint-analysis-based preference-assessment exercises (see, e.g., element 14 in FIGS. 1B and 1C), the number of possible permutations of all treatment outcomes would be determined. In particular, the number of possible permutations of the treatment outcomes would be defined as the number of possible states (levels) for each outcome multiplied together. For the above-mentioned exemplary prostate-cancer-treatment outcomes, there would be provided four exemplary levels for Sexual Function; three levels for each of Urinary Function, Bowel Function, the second aspect of Invasiveness, Recovery Time, and Survivability; and two levels for each of the first aspect of Invasiveness, possible Complications and the possibility of Transfusion. The exemplary number of possible permutations of treatment option outcomes would be 7,776 (calculated by multiplying 4×3×3×3×3×3×2×2×2).

One such exemplary Internet-based embodiment would not include the "no change" (best-case) levels in an initial stage of determining patient preference-assessment exercises for constructing and generating an interview. In constructing an exemplary interview, one such exemplary prostate-cancer module would randomly select a predetermined number (for example, nineteen (19)) of two-outcome-level combinations for a user to compare. An exemplary random selection would have two criteria: 1.) each outcome-level would only appear a predetermined maximum number of times ("n"), where "n" would be predetermined for each condition (e.g., three (3) for the exemplary prostate-cancer module); and 2.) each outcome-level should appear at least once.

For three-outcome-level combinations, the exemplary prostate-cancer. module would calculate a "Representation Value" for each possible three-outcome-level combination using a Euclidean distance measure represented by the formula: Representation Value=$a^2+b^2+c^2$, where a, b and c correspond to the number of times the three levels of a possible combination have already been included in selected two-level pairs. The exemplary prostate-cancer module would then select two three-outcome-level combinations that have the lowest two Representation Values.

Based on the above exemplary selection criteria, the exemplary prostate-cancer module would therefore select a predetermined number (for example, nineteen (19)) of two-outcome-level combinations and a predetermined number (for example, two (2)) of three-outcome-level combinations for a user to compare. Two-outcome-level and three-outcome-level combinations may sometimes be generally referred to herein as "paired comparisons."

It will be understood in the art that for purposes of presenting paired comparisons, or other numbers of comparisons, that the actual type of treatment may not be identified in a preference-assessment exercise. That is, an exemplary preference-assessment exercise "treatment" may be a "hypothetical composite" treatment described only by its attributes (e.g., outcomes such as Sexual Function effect) and attribute levels (e.g., no change, much worse with no recovery, etc.)

It will be understood by someone with ordinary skill in the art that the visual presentation of preference-assessment exercises may be varied without departing from the spirit of the present invention. It will be understood by someone with ordinary skill in the art that the number of outcome-level combinations (e.g., of two-outcome-level and three-outcome-level combinations) in a "paired comparison" described herein is exemplary and not a limitation of the present invention. Other embodiments could use any number of outcomes and attribute levels in a paired comparison without departing from the spirit of the present invention. Further, it will be understood by someone with ordinary skill in the art that without departing from the spirit of the present invention, it would be possible to present preference-assessment exercises that displayed more than two treatment alternatives, where each treatment alternative was displayed with one or more treatment outcomes/attribute levels. In such an alternative embodiment, such as for example, where triple comparisons would be presented, the "radio buttons" would span the range from the left-most treatment option to the right-most treatment option; additional "radio buttons" and corresponding value increments could be provided (e.g., with increments of 0.05 as compared to the exemplary increment of 0.1 described elsewhere herein).

The exemplary prostate-cancer module would use each of the selected two-outcome-level and three-outcome-level combinations to construct paired treatment option alternative profiles for prompting a participant to provide preference ratings. That is, for a two-outcome-level combination, the exemplary prostate-cancer module would construct a first treatment option with two different outcomes and corresponding levels, and a second treatment option with two further outcomes and corresponding levels; for a three-outcome-level combination, the exemplary prostate-cancer module would construct a first treatment option with three different outcomes and corresponding levels, and a second treatment option with three further outcomes and corresponding levels.

One exemplary approach for constructing interactive paired two-outcome-level profiles (i.e., for constructing interactive paired profile exercises where each treatment option comprises two outcomes and corresponding outcome levels), the exemplary prostate-cancer module would construct a first (left-view) treatment option profile for placing in a user's left-view of an interactive exercise display (such as exemplary element number 3310 depicted in FIG. 33) that would comprise the first level of a two-level combination and a best-case (no change) level corresponding to the opposite (user's right-view) treatment option profile; the exemplary prostate-cancer module would construct a second (right-view) treatment option profile for placing in a user's right-view of an interactive exercise display (such as exemplary element number 3320 depicted in FIG. 33) that would comprise the second level of the two-level combination and a best-case (no change) level corresponding to the opposite (user's left-view) treatment option profile.

For example, if an exemplary randomly selected two-outcome-level combination comprised: 1.) Sexual Function/Much Worse With No Recovery; and 2.) Bowel Function/Temporary Rectal Urgency/Frequency With Full Recovery at 6 Months; then using the above-described exemplary approach for constructing an interactive paired two-outcome-level profile exercise, the exemplary prostate-cancer module would construct an interactive paired profile exercise comprising a user's left-view treatment option that would show the outcomes of: a.) Sexual Function/Much Worse With No Recovery; and b.) Bowel Function/No Change; and would construct an interactive paired profile exercise comprising a user's right-view treatment option that would show the outcomes of: a.) Bowel Function/Temporary Rectal Urgency/Frequency With Full Recovery at 6 Months; and b.) Sexual Function/No Change.

One exemplary approach for constructing interactive paired three-outcome-level profiles (i.e., for constructing interactive paired profile exercises where each treatment option comprises three outcomes and corresponding outcome levels), the exemplary prostate-cancer module would treat the first two levels similarly to the way described above regarding paired two-outcome profiles and would randomly assign the third outcome-level to either the user's left-view or the user's right-view; the opposing side (right-view or left-view, depending on the random assignment of the third outcome-level) would be assigned to have the best-case (no change) level corresponding to the third outcome.

For example, if an exemplary randomly selected three-outcome-level combination comprised: 1.) Sexual Function/Much Worse With No Recovery; 2.) Urinary Function/Leakage With Cough or Strain With No Recovery; and 3.) Bowel Function/Rectal Urgency/Frequency With No Recovery; and if the third level were randomly assigned user's left-view for the third outcome, then using the above-described exemplary approach for constructing an interactive paired three-outcome-level profile exercise, the exemplary prostate-cancer module would construct an interactive paired profile exercise comprising a user's left-view treatment option that would show the outcomes of: a.) Sexual Function/Much Worse With No Recovery; b.) Urinary Function/No Change; and c.) Bowel Function/Rectal Urgency/Frequency With No Recovery; and would construct an interactive paired profile exercise comprising a user's right-view treatment option that would show the outcomes of: a.) Sexual Function/No Change; b.) Urinary Function/Leakage With Cough or Strain With No Recovery; and c.) Bowel Function/No Change.

Figure 33:
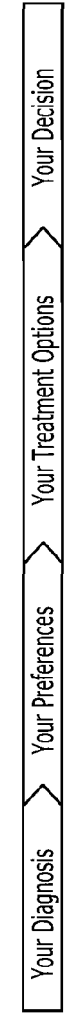
FIG. 33 is a graphic depiction of an exemplary interactive user interface three-outcome-level composite treatment outcome rating (preference assessment exercise) screen in an alternative exemplary embodiment of the present invention.

The exemplary prostate-cancer module would construct and generate for display (such as, for example, in an exemplary Internet-based embodiment, to a display device in communication with a user's client computer device) interactive paired two-outcome-level and three-outcome-level profiles with "radio buttons" such as exemplary element numbers 3330, 3335, 3340, 3345, 3350, 3355, 3360, 3365, and 3370 depicted in FIG. 33. The exemplary prostate-cancer module would associate an exemplary value of 0.1 with the left-most radio button (e.g., element 3330 depicted in FIG. 33) incrementing each progressively-right button by the value of 0.1, through to a value of 0.9 for the right-most radio button (element 3370 depicted in FIG. 33). That is, an exemplary value of 0.1 would be associated with a participant's selection of the left-most radio button (e.g., element 3330 depicted in FIG. 33); an exemplary value of 0.2 would be associated with a participant's selection of the next progressively-right radio button (e.g., element 3335 depicted in FIG. 33); an exemplary value of 0.3 would be associated with a participant's selection of the next progressively-right radio button (e.g., element 3340 depicted in FIG. 33); and similarly through each next progressively-right radio button to a value of 0.9 for the right-most radio button (element 3370 depicted in FIG. 33).

Once a user/participant had entered a preference input (i.e., a selection of a particular radio button) for each interactive paired two-outcome-level and three-outcome-level profile in the predetermined number of interactive paired two-outcome-level and three-outcome-level profile in an interview, the exemplary embodiment would calculate part-worth values. For calculating part-worth values, the exemplary embodiment would create an exemplary "State" Matrix that would comprise an exemplary number of columns equivalent to the number of active attribute levels, plus one constant; the exemplary "State" Matrix that would further comprise an exemplary number of rows corresponding to the exemplary pre-determined number of paired two- and three-outcome-level comparisons.

For example, for the above-described exemplary prostate-cancer module, an exemplary prostate-cancer-module "State" Matrix would comprise an exemplary sixteen (16) columns (one column for each "active" attribute level (i.e., not including the "No Change"/best-case attribute levels) and one constant column with a value of one); the exemplary prostate-cancer-module "State" Matrix would further comprise an exemplary twenty-one (21) rows (one for each exemplary paired comparison). The exemplary prostate-cancer-module "State" Matrix would be initialized as described as follows. The exemplary State Matrix would be populated for ordinary paired comparisons based on the presence of attribute levels greater than zero. For each exemplary two-outcome-level combination row, each corresponding column would be initialized to zero, except for the respective columns of the first and second attribute levels in a combination, which would be initialized according to the visual location values described further below. The exemplary State Matrix visual location value for an attribute level would be determined based on the visual location of the attribute level, i.e. whether it is located on the user's left-view of the display or the user's right-view of the display; the exemplary State Matrix visual location value for an attribute level would be assigned a minus one ("−1") for an attribute level that is displayed in a user's left-view of a display; the exemplary State Matrix visual location value for an attribute level would be assigned a one ("1") for an attribute level that is displayed in a user's right-view of the display. The exemplary visual display State Matrix visual location value would be randomized as described elsewhere herein with the restriction that the non-zero attribute levels would be on opposing sides of a particular visual display. The State Matrix for three-outcome-level combinations would be generated in a similar fashion. Three nonzero attribute levels would be selected based on the aforementioned Euclidean distance formula. The visual display states would be constructed at random with the restriction that at most, two nonzero levels would be displayed on one display side, those being the user's left-view or the user's right-view of the display. Post-randomization, the State Matrix visual location values would be assigned based on whether the nonzero attribute level is displayed on the user's left-view or the user's right-view of the display.

The exemplary prostate-cancer module would receive (see, e.g., element 15 in FIGS. 1B and 1C) a participant's preference input for each of the interactive paired two-outcome-level and three-outcome-level profile exercises in the interview and would add the user's preferences for each of the profile exercises to the constant column (a constants vector). In order to calculate a part-worth value for each outcome level (see, e.g., element 14 in FIGS. 1B and 1C), the exemplary prostate-cancer module would perform a linear regression using Singular Value Decomposition and would create a resulting Solution Vector that would contain a regression coefficient for each active attribute level. The exemplary prostate-cancer module would multiply each element of the State Matrix by the solution score and would sum the totals for each column, thereby calculating a predicted value for each attribute level (each outcome level). The exemplary prostate-cancer module would then identify a maximum value and a minimum value for each attribute level for each outcome attribute and would subtract the minimum from the maximum to calculate a raw part-worth score for each corresponding outcome level. The exemplary prostate-cancer module would then calculate a scaled score for each outcome level by dividing the raw part-worth score by each outcome level by the sum of all raw part-worth scores for all outcome levels.

The exemplary prostate-cancer module would then calculate an expected value for each treatment option. In order to calculate an expected value (see, e.g., element 22 in FIGS. 1B and 1C) for each treatment, the exemplary prostate-cancer module would calculate the product (see, e.g., element 17 in FIGS. 1B and 1C) of each possible exemplary prostate-cancer treatment outcome-level permutation (totaling 7,776 possible exemplary prostate-cancer treatment outcome-level permutations (calculated by multiplying 4×3×3×3×3×3×2×2×2)) multiplied by its matching utility score as calculated using the conjoint analysis algorithm. Each of the resulting products would be summed to calculate the expected value of the treatment option being evaluated in the decision analysis model.

The exemplary prostate-cancer module would then calculate a utility value (see, e.g., element 19 in FIGS. 1B and 1C) for each prostate-cancer treatment outcome-level permutation by summing the scaled part-worth values for each attribute level for the exemplary prostate-cancer treatment outcome-level permutation. A final permutation value would be calculated (see, e.g., element 21 in FIGS. 1B and 1C) for each prostate-cancer treatment outcome-level permutation by multiplying the total probability score for the permutation by the utility value for the permutation.

The exemplary prostate-cancer module would then calculate an expected value (see, e.g., element 22 in FIGS. 1B and 1C) for each exemplary prostate-cancer treatment option by summing the final permutation values for each of the possible exemplary prostate-cancer treatment outcome-level permutations for the treatment option.

The exemplary prostate-cancer module would then rank (see, e.g., element 23 in FIGS. 1B and 1C) the treatment alternatives available to the patient according to the above-mentioned calculated expected values and would identify a recommendation of a treatment (see, e.g., element 24 in FIGS. 1B and 1C) based on the ranking of the treatment alternatives and would display the treatment rankings and recommendation to the user (see, e.g., element 25 in FIGS. 1B and 1C).

It will be understood by someone with ordinary skill in the art that the above-described exemplary prostate-cancer module is illustrative and not a limitation of the present invention; other exemplary medical-condition-specific modules would similarly generate individualized patient preference assessment exercises, perform real-time, individualized conjoint analysis of patient preferences and provide real-time treatment alternative rankings and/or treatment recommendations.

Appendices A-E hereto provide exemplary source code listings for certain modules for an exemplary Multi-Attribute Conjoint Analysis engine for providing an exemplary embodiment of some of the above-described calculations. The exemplary source code listings in Appendices A-E comprise exemplary C/C++ program code. The exemplary conjoint engine modules depicted in the exemplary source code listings in Appendices A-E hereto would use modules from the "GNU (GSL) Scientific Library" which is an Open Source library of modules for scientific applications. Among others, the exemplary conjoint engine would use the GSl_Vector, GSL_Matrix and GSL_Multifit_Linear modules from the GNU Scientific Library to perform the above-mentioned Multi-Attribute Conjoint Analysis.

Appendix A hereto comprises exemplary "Level.h" and "Level.cpp" source code listings that provide exemplary internals (e.g., internal program names and characteristics) for exemplary attribute levels. Appendix B hereto comprises exemplary "Attribute.h" and "Attribute.cpp" source code listings that provide exemplary internals (e.g., internal program names and characteristics) for exemplary attributes (i.e., exemplary treatment outcomes). Appendix C hereto comprises exemplary "Profile.h" and "Profile.cpp" source code listings that include generating exemplary interactive preference profile exercises for an exemplary interview and for calculating the above-described part-worth values and expected values. Appendix D hereto comprises an exemplary "WCProfiles.xml" source code listing that comprises exemplary xml profiles for prostate cancer and benign prostate hyperplasia outcomes and attribute levels. Appendix E hereto comprises exemplary "WiserCareToolFinalDlg.h," and "WiserCareToolFinalDlg.cpp" source code listings for generating and interacting with interactive displays of the above-described "radio button" preference-assessment exercises.

One exemplary Internet-based embodiment would provide the following exemplary order of interactivity with a user and internal operation. Such an exemplary Internet-based embodiment would detect an external access by a user double clicking an icon, such as, for example, would be presented on a web-page, to activate interactivity with the exemplary Internet-based embodiment. Once a user-specific instance of interactivity with a particular user has been so activated, such an exemplary Internet-based embodiment would then locate the above-mentioned exemplary WCProfiles.xml document file (depicted in Appendix D hereto) for loading of medical condition profiles for various medical conditions for display to the user in a "listbox." In one exemplary Internet-based embodiment, an xml parser such as an open source xml parser "tinyxml," would be used.

In an alternative Internet-based embodiment, a database of profiles could be provided instead of using the above-mentioned exemplary xml file approach.

The user would select a medical condition from the listbox. Based on the user's selection of a medical condition, the exemplary Internet-based embodiment would then load the corresponding medical condition profile data from the above-mentioned exemplary WCProfiles.xml document file (depicted in Appendix D hereto).

Once the appropriate medical condition profile had been loaded, the exemplary Internet-based embodiment would generate all possible paired comparisons for two-outcome-level and three-outcome-level combinations as described elsewhere hereinabove. The three-outcome-level combinations would be based on the Euclidean balance formula described above.

The exemplary Internet-based embodiment would then select at random for display a set number of paired comparisons from the above-mentioned exemplary two-outcome-level and three-outcome-level combinations; the exemplary embodiment would ensure that all attribute levels would be represented at least once and that all attribute levels would be represented not to exceed a predetermined maximum number of times.

Once the randomization for the display has been completed, the exemplary paired comparisons would be loaded to a Graphic User Interface ("GUI"), which would be activated for the user to make selections from the displayed paired comparisons.

Once the user had completed all of the user's selections for all of the paired comparisons, the user could select a "Get Results" button (e.g., as depicted on a web-page) which would trigger the exemplary Internet-based embodiment to generate the State Matrix described above, perform the above-described regression analysis, calculate the above-described part-worth values based on the coefficients from the regression analysis, prepare the relevant ranking, recommendation and other related reporting information (including sensitivity analysis information) described elsewhere herein, and present relevant reporting to the user (e.g., in file form, text form and/or graphically via, e.g., web pages).

After the above-mentioned reporting information had been presented to the user, the particular user-specific instance of the exemplary Internet-based embodiment would be reset to its initial state so that the user could request a new profile for a new session. Alternatively, the particular user-specific instance of the exemplary embodiment would not be reset until the user had signed out to allow the user to retake the above-described preference-assessment exercises in view of sensitivity analysis reports.

Exemplary Graphic User Interface in an Exemplary Internet-Based Embodiment.

Exemplary user input would comprise an indication by the user of a patient medical condition regarding a particular patient. Exemplary user input would further comprise prognostic indicators associated with the particular patient. FIG. 8 is a graphic depiction of an exemplary interactive user interface prognostic indicator data collection screen in an exemplary embodiment of the present invention. The exemplary interactive user interface prognostic indicator data collection screen depicted in FIG. 8 depicts exemplary collection fields 805, 807, 809, 811 and 813 for collection of prognostic indicators 804, 806, 808, 810 and 812 relevant to the particular medical condition of prostate cancer; a "Previous" button 801 and a "Continue" button 802 would be provided for the user to click to navigate to a previous screen, or to continue to the next screen, respectively.

As will be understood by someone with ordinary skill in the art, the exemplary depiction in exemplary FIG. 8 of data collection for prognostic indicators for prostate cancer is not a limitation of the present invention; interactive user interface prognostic indicator data collection screens for collecting other types of prognostic indicator data associated with various other medical conditions could be used without departing from the spirit of the present invention. Further, it will be understood by someone with ordinary skill in the art that description herein of a particular medical condition, such as prostate cancer, regarding the exemplary screen depicted in FIG. 8 and the other FIGS. 9-18 discussed further below is illustrative and exemplary and is not a limitation of the invention.

Rather, in some exemplary embodiments, for example, distinct exemplary medical-condition-specific graphic user interface software modules for various distinct medical conditions would be implemented to interact with a single conjoint analysis software nucleus without departing from the spirit of the present invention.

Yet further, by way of non-limiting example, some alternative exemplary embodiments would implement distinct medical-condition-specific graphic user interfaces and each distinct medical-condition-specific graphic user interface would interact with a particular conjoint analysis software module/nucleus. In some such alternative exemplary embodiments, multiple conjoint analysis software modules/nuclei would be provided; each conjoint analysis software module/nucleus would comprise software to implement a particular conjoint analysis methodology; a particular medical-condition-specific graphic user interface module would interact with a particular conjoint analysis software module/nucleus; however, various medical-condition-specific graphic user interface modules would interact with a different particular conjoint analysis software module/nucleus.

Figure 19:
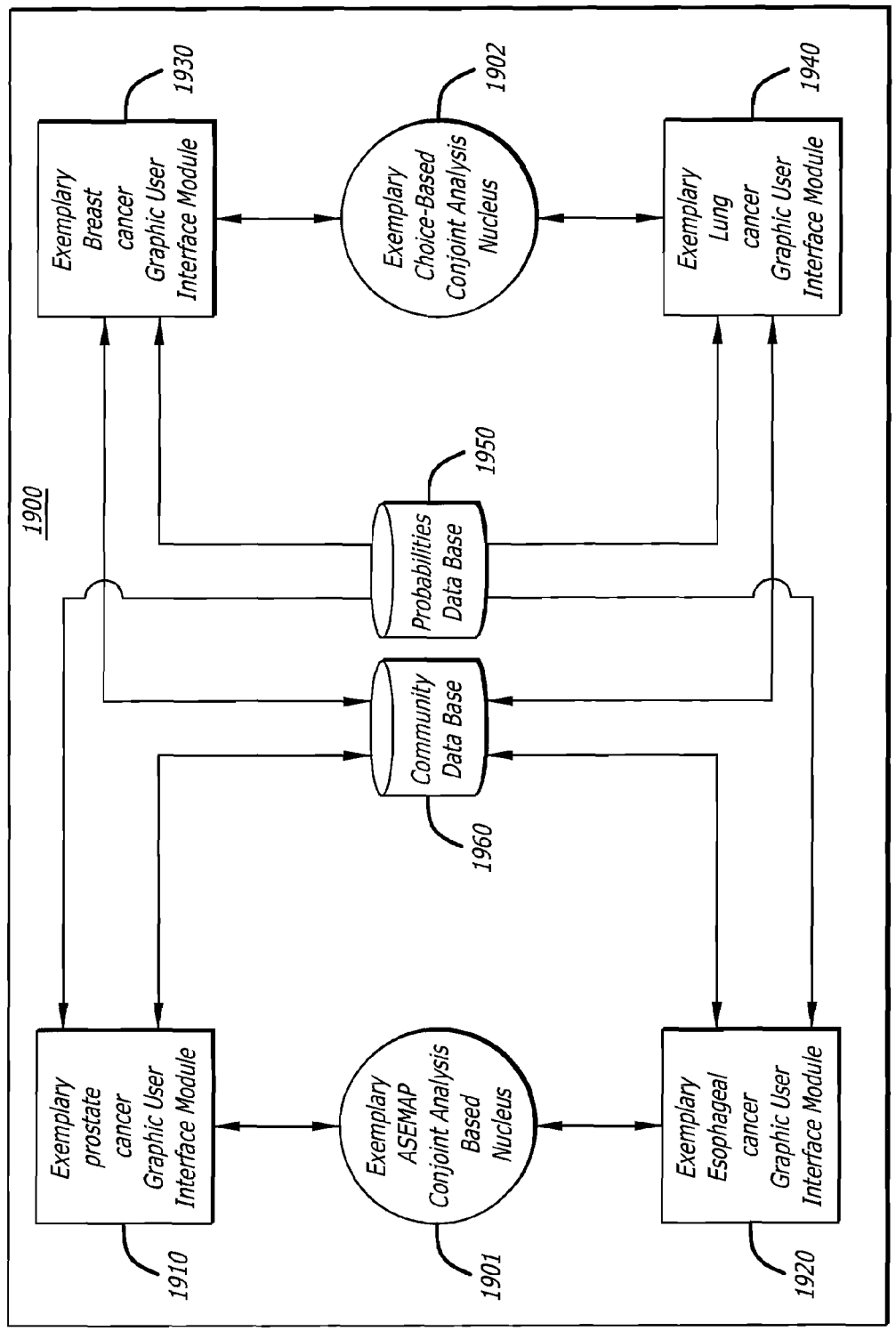
FIG. 19 is a high level diagram depicting exemplary graphic user interface and conjoint analysis system components in an alternative exemplary embodiment of the present invention.

FIG. 19 is a high level diagram depicting exemplary graphic user interface modules 1910, 1920, 1930 and 1940 and exemplary conjoint analysis modules/nuclei 1901 and 1902 in an alternative exemplary system 1900 embodiment of the present invention. After accessing an exemplary website (or other processing environment) providing exemplary services embodying the present invention, an exemplary set of medical conditions would be presented. For example, as depicted in FIG. 20, an exemplary screen 2000 would be presented and would depict one or more medical conditions as medical-condition-specific "tabs", by way of non-limiting example, e.g., prostate cancer (depicted as exemplary tab 2010), breast cancer (depicted as exemplary tab 2020), esophageal cancer (depicted as exemplary tab 2030), lung cancer (depicted as exemplary tab 2040), and/or various other medical conditions.

It will be understood by someone with ordinary skill in the art that the exemplary description herein of certain medical conditions, or of a certain number of medical conditions, is not a limitation of the present invention. Rather, exemplary embodiments of the present invention could provide the described services for various and multiple medical conditions without departing from the spirit of the present invention; various exemplary embodiments of the present invention would be expandable/scalable to include any number of, and any type of, medical condition(s) without departing from the spirit of the present invention.

Figure 20:
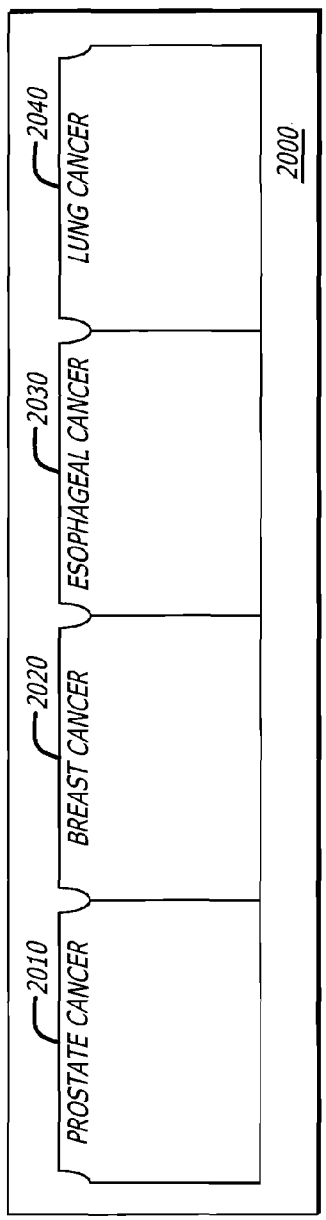
FIG. 20 is a graphic depiction of an exemplary interactive graphic user interface medical condition selection screen in an exemplary embodiment of the present invention.

With reference to FIG. 20, a user selection, e.g., by clicking, of a particular exemplary medical condition tab (2010, 2020, 2030 or 2040), would cause the exemplary embodiment to navigate to a corresponding medical-condition-specific graphic user interface module and associated set of interactive graphic user interface screens corresponding to the selected medical condition. For example, a user selection of the exemplary prostate cancer tab 2010 would cause the exemplary system to navigate to an exemplary prostate cancer graphic user interface module, depicted as element 1910 in FIG. 19. In the exemplary embodiment system 1900 depicted in FIG. 19, exemplary prostate cancer graphic user interface module 1910 would interface and interact with an exemplary ASEMAP-adapted conjoint analysis-based software module nucleus 1901. Exemplary prostate cancer graphic user interface module 1910 would comprise software for providing a series of interactive graphic user interface screens that correspond in content, data gathering and conjoint-analysis-interactivity with data and circumstances related to prostate cancer, such as are described further below with respect to exemplary FIGS. 9-18.

Each exemplary medical-condition-specific graphic user interface module, e.g., 1910, 1920, 1930 and 1940 depicted in FIG. 19, would comprise software that would provide a series of interactive medical-condition-specific graphic user interface screens that would correspond in content, data gathering and conjoint-analysis-interactivity, with the data and circumstances related to the specific corresponding medical condition.

In the exemplary embodiment system 1900 depicted in FIG. 19, each exemplary medical-condition-specific graphic user interface module, e.g., 1910, 1920, 1930 and 1940 depicted in FIG. 19, would access an exemplary probabilities data base 1950, and would access and store information on an exemplary community database 1960, and/or would access and/or store information on one or more other databases (not shown).

In the exemplary embodiment system 1900 depicted in FIG. 19, exemplary esophageal cancer graphic user interface module 1920 would also interface and interact with an exemplary ASEMAP-adapted conjoint analysis-based software module nucleus 1901. However, in the exemplary embodiment system 1900 depicted in FIG. 19, exemplary breast cancer graphic user interface module 1930 and exemplary lung cancer graphic user interface module 1940 would interface and interact with exemplary choice-based conjoint analysis software module nucleus 1902.

Figure 21:
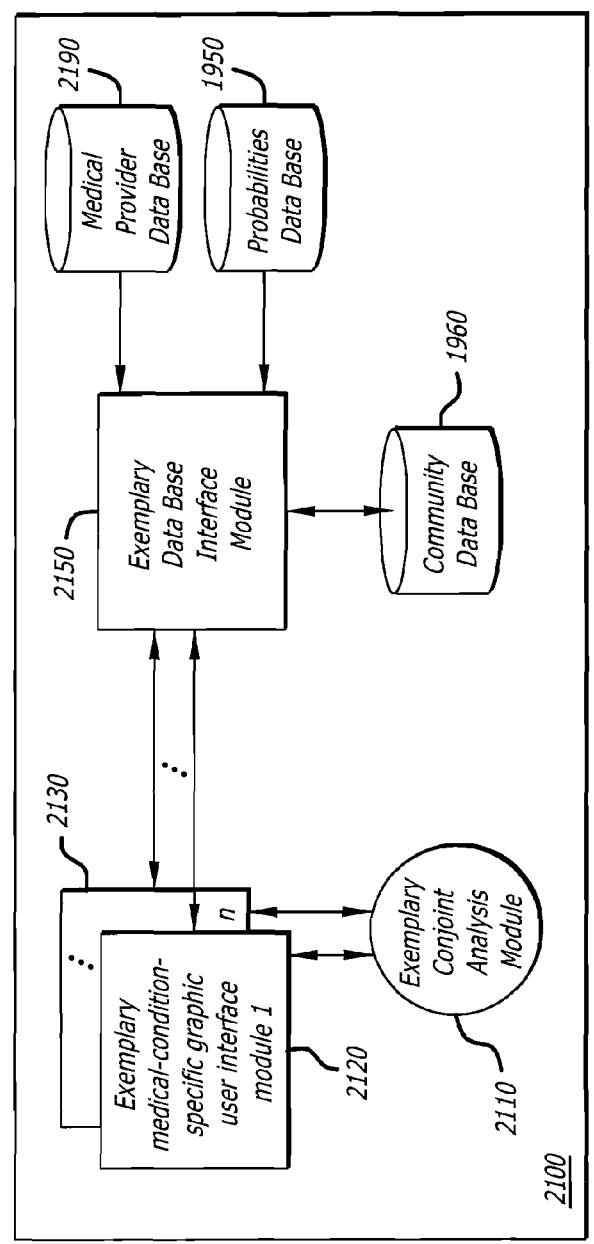
FIG. 21 is a high level diagram depicting exemplary activity between multiple exemplary interactive graphic user interface modules, an exemplary conjoint analysis module and an exemplary data base interface module in an exemplary embodiment of the present invention.

As will be understood by someone with ordinary skill in the art, alternative exemplary embodiments would use a single conjoint analysis module, such as exemplary element 2110 depicted in FIG. 21 with which all graphic user interface modules, such as exemplary medical-condition-specific graphic user interface module 1 (element 2120) through exemplary medical-condition-specific graphic user interface module "n" ("n" indicating an unspecified plurality) (element 2130) would interface and interact. Alternatively, other exemplary embodiments would use multiple conjoint analysis modules; different graphic user interface modules would interface and interact with a particular conjoint analysis module, as illustratively depicted in FIG. 20.

Returning with reference to FIG. 21, in one exemplary embodiment system 2100 depicted in FIG. 21, each interactive graphic user interface module 2120-2130 would further interact with an exemplary data base interface module 2150 that would access various data bases, e.g., a probabilities data base 1950, a community data base 1960, a medical provider data base 2190, and other data bases (not shown).

In further alternative exemplary embodiments (not shown), multiple conjoint analysis modules/nuclei would be provided, each conjoint analysis module/nuclei comprising software that would execute a single type of conjoint analysis methodology, such as for example, an adaptation of ASEMAP; each conjoint analysis module, such as each ASEMAP-adapted conjoint analysis module, would be tailored to handle a certain customized number and/or identity of attributes and/or outcomes and/or other conditions relevant to a certain medical condition or set of medical conditions.

As will be understood by someone with ordinary skill in the art, the illustrative architecture of exemplary medical-condition-specific graphic user interfaces with exemplary conjoint analysis modules described herein is exemplary and illustrative and is not a limitation of the present invention. Rather, other component structures and relationships between graphic user interface software and conjoint analysis software could be implemented without departing from the spirit of the present invention.

FIG. 9 is a graphic depiction of an exemplary interactive user interface prognostic indicator clinical assessment data collection screen in an exemplary embodiment of the present invention. The exemplary interactive user interface prognostic indicator clinical assessment data collection screen depicted in FIG. 9 depicts exemplary collection fields 903 for collection of other medical conditions that exist for the particular patient; a "Previous" button 901 and a "Continue" button 902 would be provided for the user to click to navigate to a previous screen, or to continue to the next screen, respectively. In one exemplary embodiment, the exemplary interactive user interface prognostic indicator clinical assessment data collection screen would collect information regarding other medical conditions that may commonly exist in association with a particular medical condition. In another exemplary embodiment, an exemplary interactive user interface prognostic indicator clinical assessment data collection screen may be general and collect information regarding various other medical conditions.

In one exemplary embodiment, such as depicted in FIG. 19, each exemplary graphic user interface module, e.g., 1910, 1920, 1930 and 1940, would access relevant data bases, e.g., 1950, 1960. In other exemplary embodiments, as depicted in FIG. 21, exemplary graphic user interface modules, e.g., 2120 through 2130, would interact with an exemplary data base interface module 2150 which would in turn access various data bases, e.g., 1950, 1960, 2190, etc.

In one exemplary Internet-based conjoint-analysis-based embodiment, such as, for example, an exemplary ASEMAP-adapted conjoint-analysis-based embodiment or an exemplary custom conjoint-analysis-based embodiment, in response to the user input of the patient medical condition and prognostic indicators regarding the patient, the exemplary server computer (whether alone or in conjunction with one or more other computer devices) would be further programmed to display to a display device in communication with the client computer, an interactive set of medical treatment attributes and corresponding treatment outcomes that would be associated with various treatment alternatives that would be available to the particular patient according to the patient medical condition and according to the prognostic indicators associated with the particular patent.

It will be understood by someone with ordinary skill in the art that reference herein to a server computer being programmed, whether alone or in conjunction with one or more other computer devices) is non-limiting and is illustrative of the above-described alternatives of providing multiple medical-condition-specific user interface modules that interface with, and interact with, one, or one of various, conjoint analysis module(s). It will be understood by someone with ordinary skill in the art that each medical-condition-specific user interface module could be provided on (e.g., the software could reside on and/or be executed by) a single server computer or other computer device, or on (e.g., the software could reside on and/or be executed by) one of various server computer or other computer devices; each conjoint analysis module could be provided on (e.g., the software could reside on and/or be executed by) a single server computer or other computer device, or on (e.g., the software could reside on and/or be executed by) one of various server computer or other computer devices. In alternative embodiments, software comprising a single logical medical-condition-specific user interface module and/or software comprising a single logical conjoint analysis module, could be located on and/or executed on or by more than one computer device. The aforementioned exemplary system architectures are illustrative and non-limiting; other system architectures, whether now known or in the future discovered, could be provided without departing from the spirit of the present invention.

FIG. 10 is a graphic depiction of an exemplary user interface treatment attribute and outcome description screen in an exemplary embodiment of the present invention. The exemplary user interface treatment attribute and outcome description screen depicted in FIG. 10 depicts explanations 1004 of various treatment attributes and possible outcomes related to prostate cancer; a "Previous" button 1001 and a "Continue" button 1002 are provided for the user to click to navigate to a previous screen, or to continue to the next screen, respectively. As mentioned above, description herein of the particular medical condition of prostate cancer is illustrative and exemplary and not a limitation of the invention.

In such an exemplary Internet-based conjoint-analysis-based embodiment, the exemplary server computer (whether alone or in conjunction with one or more other computer devices) would be further programmed to prompt the user to rank each medical treatment attribute and a corresponding treatment outcome with respect to the desirability of an improvement in that outcome compared to a similar level of improvement in each other medical treatment attribute and corresponding treatment outcome in the interactive set of medical treatment attributes and corresponding treatment outcomes.

FIG. 11 is a graphic depiction of an exemplary interactive user interface treatment option changes rating screen in an exemplary embodiment of the present invention. The exemplary interactive user interface treatment option changes rating screen depicted in FIG. 11 would display a plurality of exemplary treatment option attribute and corresponding treatment option attribute change entries 1190 related to prostate cancer treatments. Each exemplary treatment option attribute and corresponding treatment option attribute change entry 1190 depicted in FIG. 11 would comprise a treatment option attribute 1140, an initial condition 1150 and an improved condition 1160. As depicted In FIG. 11, a respective ranking input field 1110, increase button 1120 and decrease button 1130 would be associated with each exemplary treatment option attribute and corresponding treatment option attribute change entry 1190. In the exemplary Internet-based conjoint-analysis-based embodiment, the exemplary server computer (whether alone or in conjunction with one or more other computer devices) would be further programmed to prompt the user to indicate in each respective ranking input field 1110, the user's ranking of the corresponding exemplary treatment option attribute and corresponding treatment option attribute change entry 1190.

In the exemplary Internet-based conjoint-analysis-based embodiment, each respective ranking input field 1110 would be initialized to 0; the user would not be allowed to continue with the medical treatment decision support analysis until each respective ranking input field 1110 had been set; duplicate rankings (multiple entries with the same ranking) would not be allowed. In an alternative embodiment, each respective ranking input field 1110 would be initialized to a proposed ranking that would be set according to statistical analysis of data collected from other users that had previously used the system and who had similar medical conditions and/or prognostic indicators. For example, the exemplary prostate cancer user interface module 1910 as depicted in FIG. 19, would access an exemplary community data base 1960 to determine statistical rankings for each respective exemplary treatment option attribute and corresponding treatment option attribute change entry (e.g., as had been displayed as exemplary element 1190 depicted in FIG. 11) based on data from other users that had previously used the system and who had similar medical conditions and/or prognostic indicators. In yet another alternative embodiment, each respective ranking input field 1110 would be initialized to a proposed ranking that would be set arbitrarily and/or randomly. The ways described herein of initializing the rankings are illustrative and exemplary; other ways of initializing the rankings could be used without departing from the spirit of the present invention. A "Previous" button 1101 and a "Continue" button 1102 would be provided for the user to click to navigate to a previous screen, or to continue to the next screen, respectively.

As will be understood by someone with ordinary skill in the art, the depiction of respective ranking input fields 1110, increase buttons 1120 and decrease buttons 1130 are exemplary ways to rank treatment option attributes and corresponding treatment option attribute changes. Other ways could be provided for ranking such entries without departing form the spirit of the present invention. For example, an alternative exemplary user interface for ranking such entries could prompt the user to click and drag each entry into an ordered list (not shown).

In response to a user input of a ranking of each medical treatment attribute and corresponding treatment outcome, the exemplary server computer (whether alone or in conjunction with one or more other computer devices) would be further programmed to display to the display device in communication with the client computer, an interactive series of user-preference rating exercises and user rating comparison exercises, each exercise prompting the user to input a rating and/or a comparison rating for various medical treatment attributes and corresponding treatment outcomes. FIG. 12 is a graphic depiction of an exemplary interactive user interface treatment option comparison rating screen in an exemplary embodiment of the present invention. As depicted in FIG. 12, an exemplary interactive user interface treatment option comparison rating screen would present an exemplary subset, such as, for example, two, treatment attributes 1210 and 1220 and an associated treatment outcome scale 1213/1215 and 1223/1225. Each exemplary treatment outcome scale 1213/1215 and 1223/1225 would range from a least desirable outcome, e.g., 1212/1216 and 1222/1226 to a most desirable outcome, e.g., 1214/1218 and 1224/1228. A sliding indicator, e.g., 1219 and 1229, would be provided for the user to slide to indicate the user's value of the importance of the possible improvement in how a treatment could affect the patient. The exemplary screen would depict a numerical value 1211 and 1221 associated with the relative position (between 0 and 100) of the respective sliding indicator, e.g., 1219 and 1229. A "Previous" button 1201 and a "Continue" button 1202 would be provided for the user to click to navigate to a previous screen, or to continue to the next screen, respectively.

The number of such exemplary interactive user interface treatment option comparison rating screens that may be presented to a user may differ from one medical condition to another, and may differ depending on a particular patient's prognostic indicators and/or the user's rankings in the previously described exemplary treatment option attribute and corresponding treatment option attribute change entries 1190 described above with respect to FIG. 11.

FIG. 13 is a graphic depiction of an exemplary interactive user interface treatment option recovery impact rating screen in an exemplary embodiment of the present invention. As depicted in FIG. 13, an exemplary interactive user interface for the rating of the importance of "speed of recovery" screen would present a recovery period for a particular treatment outcome 1310 and a set of indicator buttons 1350 with which the user could indicate the user's importance for the indicated recover period 1310 on a scale of possible treatment outcomes 1320-1330.

Figures 1, 14:
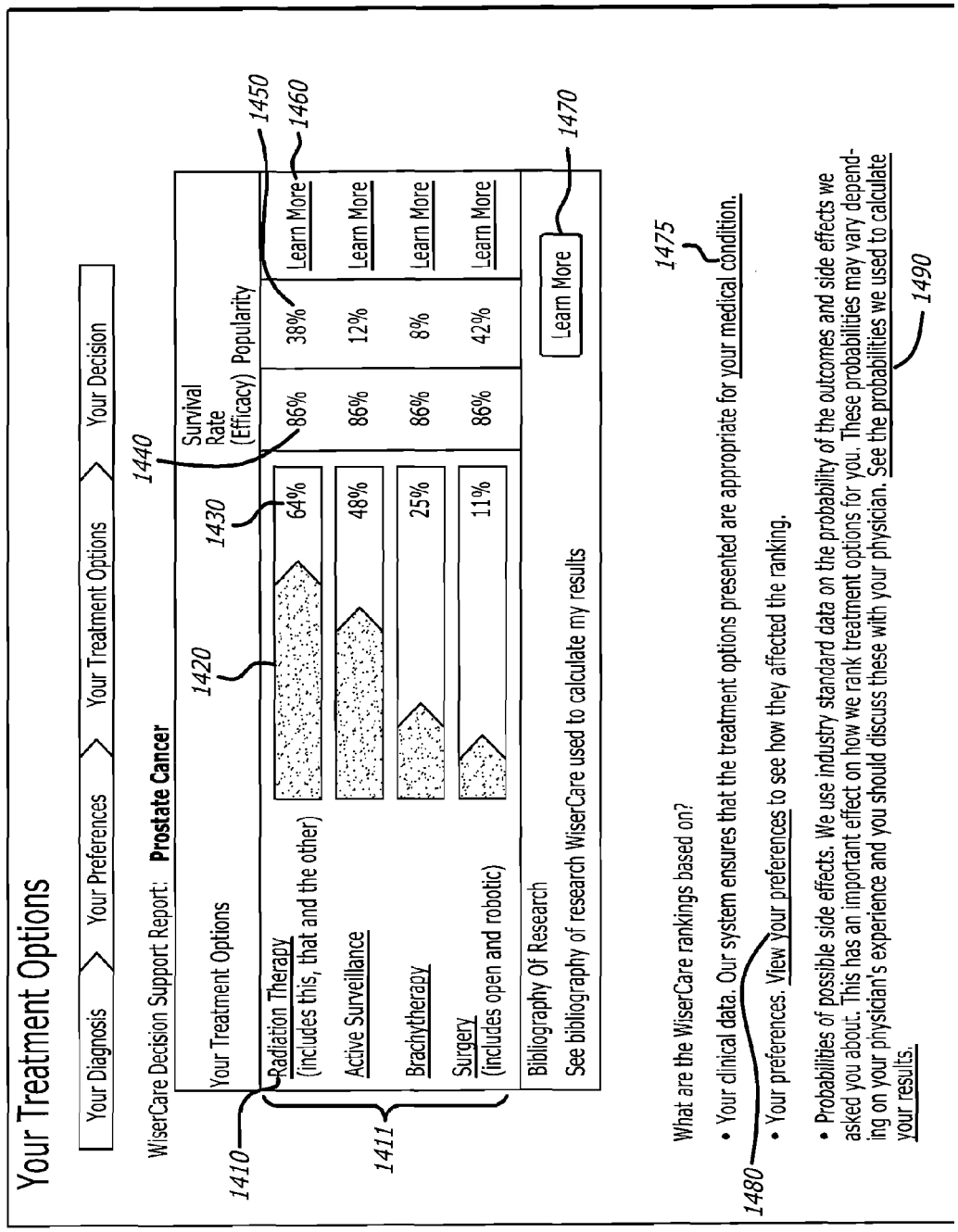
FIG. 14 is a graphic depiction of an exemplary interactive user interface treatment option ranking report screen in an exemplary embodiment of the present invention.
Figures 2, 15:
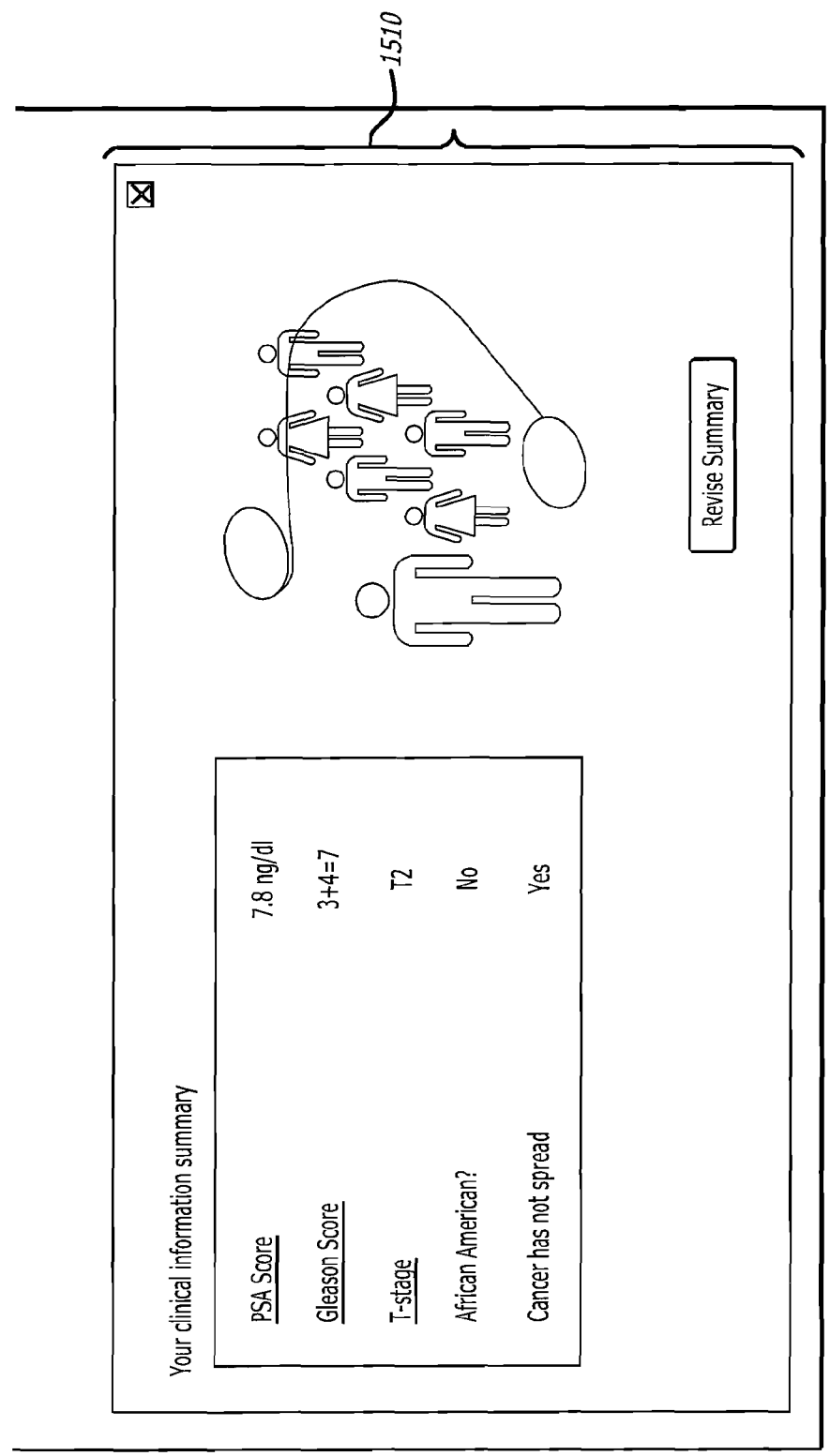
FIG. 15 is a graphic depiction of an exemplary interactive user interface treatment option ranking report screen with a clinical information summary insert in an exemplary embodiment of the present invention.

In such an exemplary Internet-based conjoint-analysis-based embodiment, the exemplary server computer (whether alone or in conjunction with one or more other computer devices) would be further programmed, such as using a conjoint-analysis-based module, to determine the importance of, and rank, each medical treatment alternative available for the particular patient according to: the patient medical condition, the prognostic indicators associated with the particular patient, the user input of the ranking of each medical treatment attribute and corresponding treatment outcome and the rating and/or the comparison rating for various medical treatment attributes and corresponding treatment outcomes. In such an exemplary Internet-based conjoint-analysis-based embodiment, the exemplary server computer (whether alone or in conjunction with one or more other computer devices) would be further programmed to display to the display device in communication with the client computer, a ranking of various medical treatments available to the particular patient. FIG. 14 is a graphic depiction of an exemplary interactive user interface treatment option ranking report screen in an exemplary embodiment of the present invention. As depicted in FIG. 14, an exemplary interactive user interface treatment option ranking report screen would provide a graphically ordered ranking 1411 of each treatment option 1410 according to the user's input and the results of the above-mentioned conjoint analysis.

In one such exemplary Internet-based conjoint-analysis-based embodiment, the exemplary server computer (whether alone or in conjunction with one or more other computer devices) would be further programmed to display the ranking of each medical treatment to the display device in communication with the client computer with a graphic depiction of the ranking of said medical treatment. In one such exemplary Internet-based conjoint-analysis-based embodiment, the exemplary server computer (whether alone or in conjunction with one or more other computer devices) would be further programmed to display a Survival Rate corresponding to each medical treatment; exemplary survival rate information would be determined, for example, by the exemplary graphic user interface module (or by some intermediary software module (not shown)) from an exemplary probabilities data base, such as depicted, for example, as element 1950 in FIG. 19. In one such exemplary Internet-based conjoint-analysis-based embodiment, the exemplary server computer (whether alone or in conjunction with one or more other computer devices) would be further programmed to display a popularity ranking associated with each medical treatment. In one such exemplary Internet-based conjoint-analysis-based embodiment, the popularity ranking would be based on treatment alternatives selected by other users of the exemplary Internet-based conjoint-analysis-based embodiment with similar medical conditions and/or prognostic indicators. In another exemplary Internet-based conjoint-analysis-based embodiment, the popularity ranking would be based on national statistics of treatment alternatives selected by other patients with similar medical conditions and/or prognostic indicators.

As will be understood by someone with ordinary skill in the art, there are various ways for measuring a patient's preferences regarding treatment outcomes. The exemplary user interfaces described herein are illustrative and not a limitation of the present invention. FIG. 33 is a graphic depiction of an exemplary interactive user interface three-outcome-level composite treatment outcome rating (preference assessment exercise) screen in an alternative exemplary embodiment of the present invention.

The exemplary interactive user interface shown in FIG. 33 depicts two exemplary composite outcomes A (element 3310) and B (element 3320). Exemplary composite outcomes, such as 3310 and 3320, are sometimes referred to herein as "hypothetical composite treatments."

Figure 34:
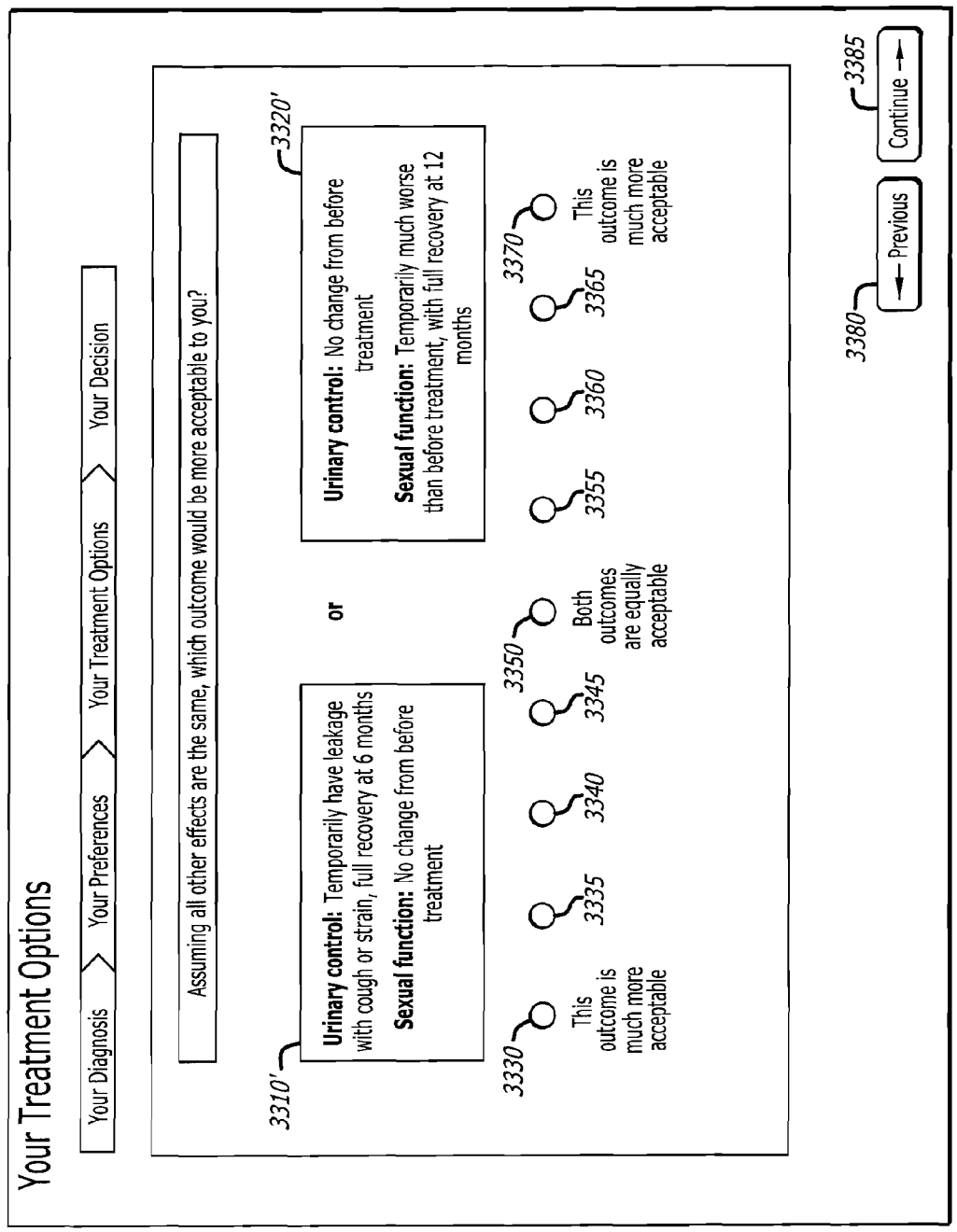
FIG. 34 is a graphic depiction of an exemplary interactive user interface two-outcome-level composite treatment outcome rating (preference assessment exercise) screen in an alternative exemplary embodiment of the present invention.

FIG. 34 is a graphic depiction of an exemplary interactive user interface two-outcome-level composite treatment outcome rating (preference assessment exercise) screen in an alternative exemplary embodiment of the present invention. The preference assessment exercise screen depicted in FIG. 34 is similar to the user interface screen depicted in FIG. 33, except that two outcome levels are depicted for each hypothetical composite treatment 3310' and 3320' in FIG. 34 instead of three outcome levels as depicted in FIG. 33.

With reference to FIG. 33, each exemplary composite outcome 3310 and 3320 comprises an exemplary plurality of exemplary discreet outcome levels. For example, exemplary composite outcome A 3310 comprises an exemplary first discreet outcome level that "urinary function remains as it is today"; an exemplary second discreet outcome level of "decreased sexual function"; and an exemplary third discreet outcome level of "no surgical incision." Exemplary composite outcome B 3320 comprises an exemplary first discreet outcome level of "temporary urinary leakage, followed by a return to normal; an exemplary second discreet outcome level of "sexual function as it is today"; and an exemplary third discreet outcome level of "surgical incision." The exemplary interactive user interface shown in FIG. 33 depicts an exemplary plurality of exemplary user preference indicator "radio buttons" (3330, 3335, 3340, 3345, 3350, 3355, 3360, 3365 and 3370), ranging in preference status from "This outcome is much more acceptable" 3330 for exemplary composite outcome A 3310, to "Both outcomes are equally acceptable" 3350 (as between the two exemplary composite outcomes (hypothetical composite treatments) A and B) to "This outcome is much more acceptable" 3370 relating to exemplary composite outcome B 3320. A patient would indicate the patient's preferences by clicking one of the exemplary user preference indicator "buttons" (3330, 3335, 3340, 3345, 3350, 3355, 3360, 3365 and 3370) and would then click the exemplary Continue button 3385 to proceed to the next exercise or stage of the process, as the case may be.

As will be understood by someone with ordinary skill in the art, the patient's preferences expressed through composite outcome level patient preference assessment exercises such as illustratively depicted in FIGS. 33 and 34 would be analyzed using Multi-Attribute Conjoint Analysis.

In FIG. 14, an exemplary graphic rating 1420, an exemplary numerical rating 1430, an exemplary survival rate 1440 and an exemplary popularity rate 1450 would be displayed for each ranked treatment option 1410. In one exemplary embodiment, the exemplary popularity rate 1450 would be based on national statistics of treatments selected by persons with the same medical condition and with similar prognostic indicators. In another exemplary embodiment, the exemplary popularity rate 1450 would be based on system-wide statistics of treatments selected by persons with the same medical condition and with similar prognostic indicators, such as, for example, from an exemplary community data base 1960 depicted in FIG. 19.

It will be understood by those with ordinary skill in the art that the above-described exemplary features of determining and displaying graphic ratings, numerical ratings, survival rates and popularity rates would not be limited to an Internet-based embodiment or to any particular conjoint-analysis methodology but rather could be implemented without departing from the spirit of the present invention, in any processing environment whether now known or in the future discovered and/or in conjunction with the previously-above-described choice-based conjoint analysis embodiment and/or in conjunction with other embodiments that use one or more other types of conjoint analysis methodologies.

Figures 2, 16:
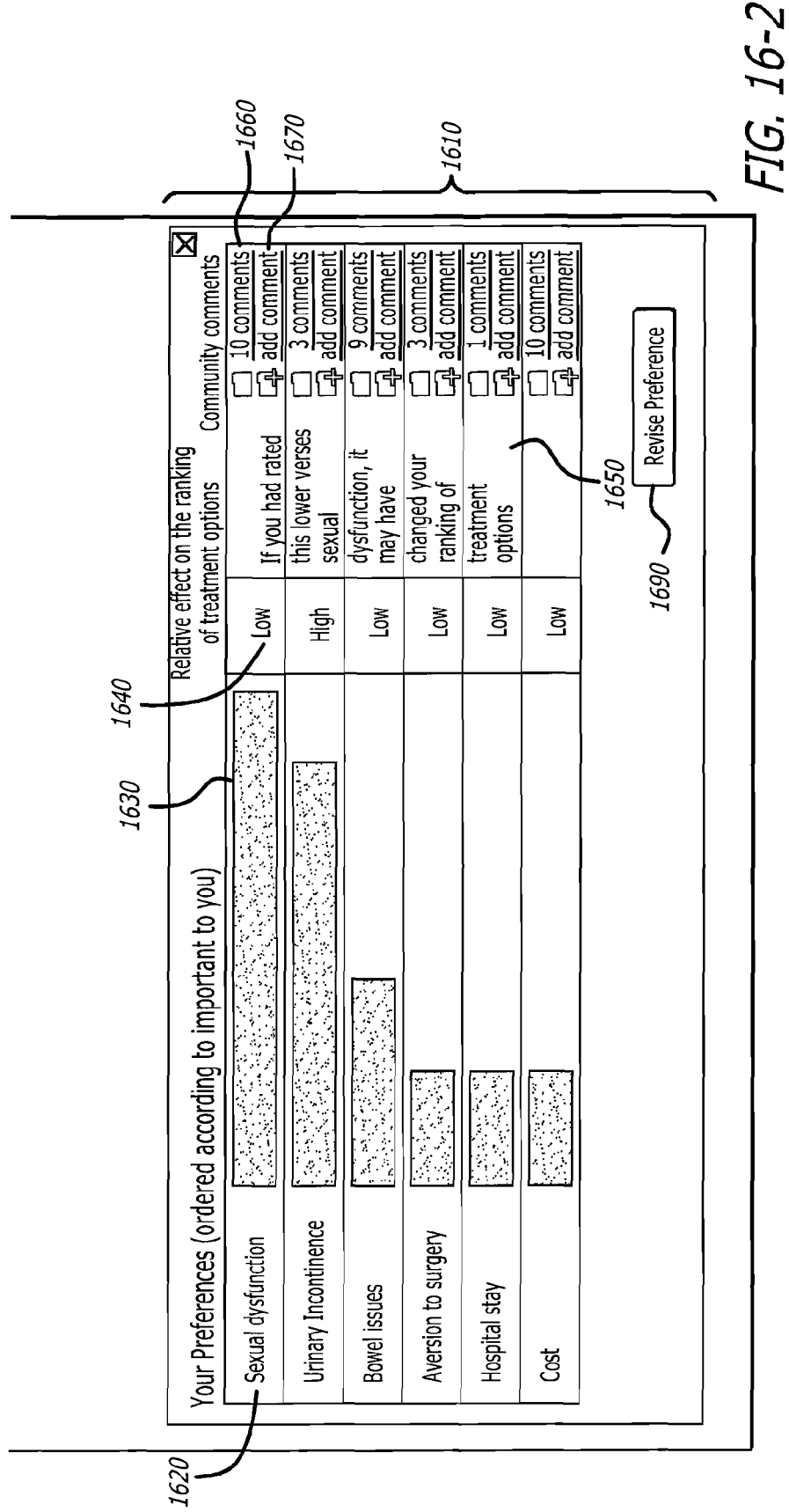
FIG. 16 is a graphic depiction of an exemplary interactive user interface treatment option ranking report screen with a personal preferences ranking summary insert in an exemplary embodiment of the present invention.
Figures 1, 17:
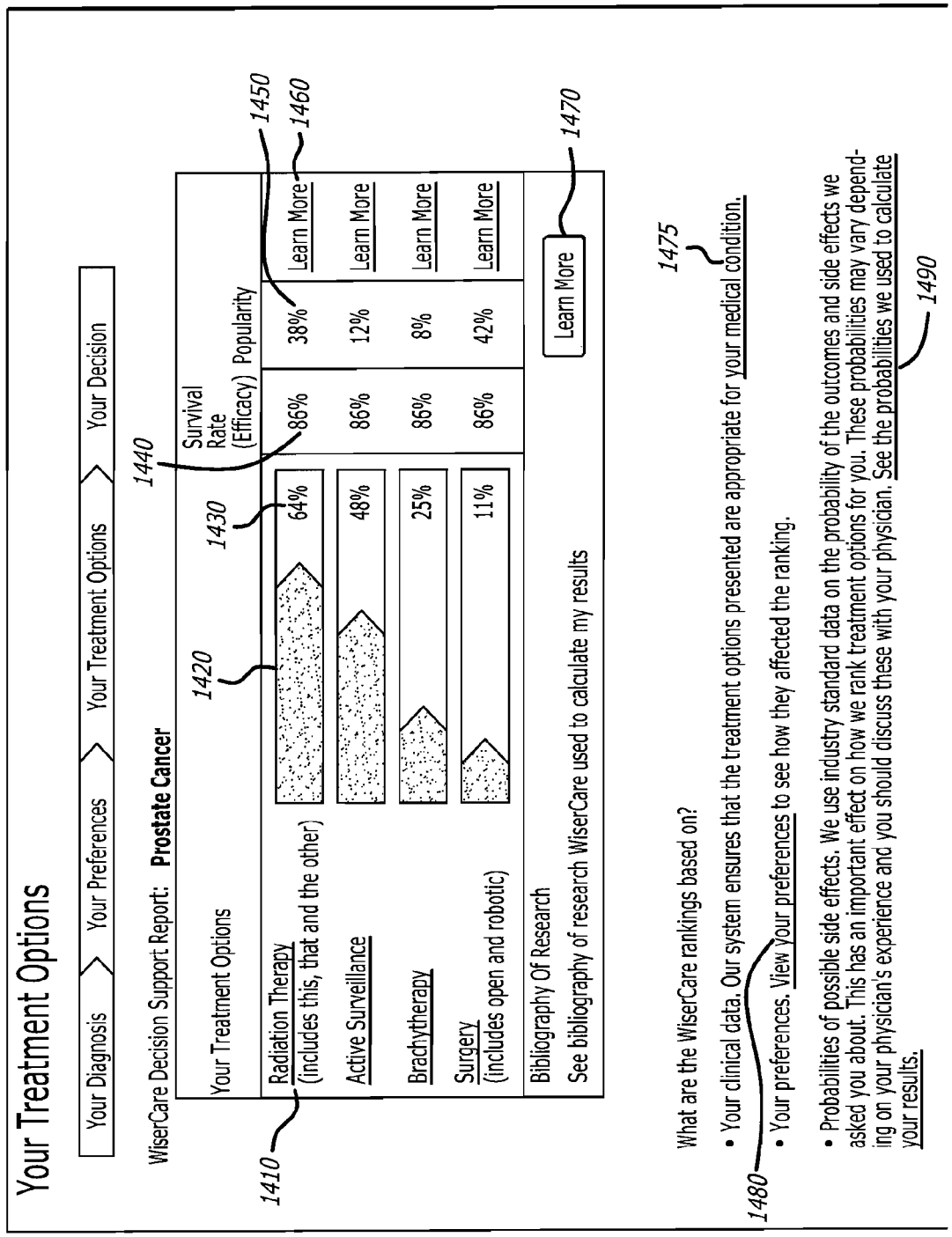
FIG. 17 is a graphic depiction of an exemplary interactive user interface treatment option ranking report screen with a personal preferences ranking summary insert and an expanded community comments insert in an exemplary embodiment of the present invention.

Returning with reference to FIG. 14, a "Learn More" button 1460 would be provided for user selection in association with each treatment option for additional information. A Bibliography of Research "Learn More" button 1470 would be provided that, if clicked by the user, would cause the display of bibliographic citations for research used to calculate the results. An interactive link for the patient's medical condition information 1475 would be provided, that if clicked, would present a display insert (element 1510, depicted in FIG. 15) that would depict a summary of the user's input of the patient medical condition and prognostic indicators. An interactive link for the user-input of preferences 1480 would be provided, that if clicked, would present a display insert (element 1610, depicted in FIG. 16) that would display a ranking of treatment attributes 1620 with a graphic indicator 1630, and in some embodiments, a numerical indicator (not shown) of the relative importance associated with the respective treatment attribute 1620 by the user. With further reference to FIG. 16, sensitivity analysis results would be depicted as a relative effect on the ranking of treatment options 1640 (e.g., as a High, Medium or Low) for each respective treatment attribute. Sensitivity analysis for attributes for which the relative effect on ranking had been High would be highlighted with an explanation to the user of the high impact the user's ratings had on the ranking of treatment options 1650; specifically, a change of a certain amount in the utility value associated with an attribute rated as "high" importance would change the rankings presented. An interactive link to community comments 1660 would be provided for user access to community comments regarding the corresponding treatment attribute (see elements 1710 and 1720 depicted in FIG. 17). An interactive link for the user to add comments 1670 would also be provided. A "Revise Preferences" button would be provided to allow the user to return to the rating process to test the effect of different ratings on the final treatment option ranking.

It will be understood by those with ordinary skill in the art that the above-described exemplary features regarding sensitivity analysis, and for the "Learn More" function, the "Bibliography" function, and the "Revise Preferences" function, would not be limited to an Internet-based embodiment or to any particular conjoint-analysis methodology but rather could be implemented without departing from the spirit of the present invention, in any processing environment whether now known or in the future discovered and/or in conjunction with the previously-above-described choice-based conjoint analysis embodiment and/or in conjunction with other embodiments that use one or more other types of conjoint analysis methodologies.

Figures 2, 18:
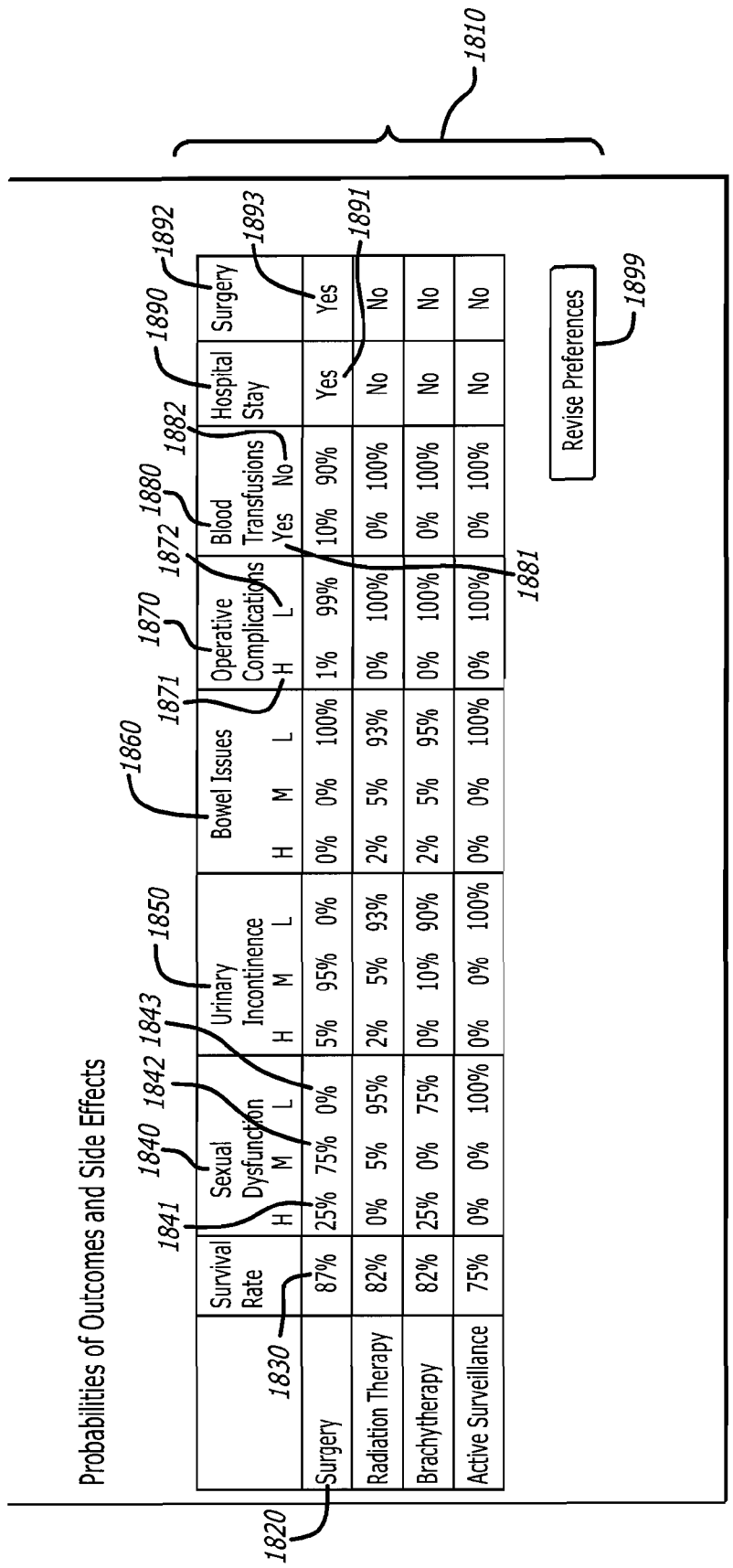
FIG. 18 is a graphic depiction of an exemplary interactive user interface treatment option ranking report screen with an outcome and side effect probability summary insert in an exemplary embodiment of the present invention.

Returning with reference to FIG. 14, an interactive link for the probabilities that were used to calculate the patient's results 1490 would be provided. Clicking the Probabilities link 1490 would cause the display of a Probabilities of Outcomes and Side Effects chart insert, an exemplary embodiment of which 1810 is depicted in FIG. 18. As depicted in FIG. 18, an exemplary Probabilities of Outcomes and Side Effects chart insert 1810 would comprise a display of each treatment option 1820 that would be available to the particular patient. For each treatment option 1820, a survival rate 1830 would be displayed. For each treatment option, various treatment attributes (e.g., side effects), e.g., 1840, 1850, 1860, 1870, 1880, 1890 and 1892, would be displayed. Depending on the nature of the treatment attributes, High-Medium-Low probabilities, e.g., 1841, 1842 and 1843, associated with the occurrence of the treatment attribute or side effect may be displayed; or in other cases, High and Low probabilities, e.g., 1871 and 1872; or in other cases, Yes and No probabilities 1881 and 1882 would be displayed. For yet other treatment attributes, e.g., 1892, rather than probabilities, Yes or No indicators 1893 would be provided. As further depicted in FIG. 18, a "Revise Preferences" button 1899 would be provided to allow the user to return to the rating process to test the effect of different ratings on the final treatment option ranking.

It will be understood, by those with ordinary skill in the art that the above-described exemplary feature of determining and displaying an exemplary Probabilities of Outcomes and Side Effects chart would not be limited to an Internet-based embodiment or to any particular conjoint-analysis methodology but rather could be implemented without departing from the spirit of the present invention, in any processing environment whether now known or in the future discovered and/or in conjunction with the previously-above-described choice-based conjoint analysis embodiment and/or in conjunction with other embodiments that use one or more other types of conjoint analysis methodologies.

Further, it will be understood by someone with ordinary skill in the art that the exemplary depiction herein of the exemplary Probabilities of Outcomes and Side Effects chart depicted in FIG. 18 is not a limitation of the present invention. Rather, other ways of depicting probabilities of outcomes and side effects may be provided without departing from the spirit of the present invention. For example, an alternative exemplary user interface for viewing treatment outcome and side effect probabilities is depicted in FIG. 22. In an exemplary alternative embodiment, if the exemplary interactive link 1490 as depicted in exemplary FIG. 14 was selected/clicked, the alternative exemplary embodiment would provide an alternative exemplary user interface for viewing of National Average Treatment Outcomes and Probabilities as depicted in FIG. 22. As depicted in FIG. 22, an alternative exemplary Probabilities of Outcomes and Side Effects user interface would comprise a selectable tab for each treatment outcome (e.g., for Prostate cancer, for example, exemplary selectable possible outcome tabs 1830' (Survival), 1840' (Sexual dysfunction), 1850' (Urinary function), 1860' (Bowel function) and 2280 (Other) would be provided).

It will be understood by someone with ordinary skill in the art that depiction of particular exemplary selectable treatment outcome tabs for possible outcomes regarding prostate cancer is illustrative and exemplary and is not a limitation of the present invention. Rather, for other conditions, selectable treatment outcome tabs would be generated by the alternative exemplary embodiment for treatment outcomes associated with the particular condition, and probabilities associated with the relevant treatment outcomes for the particular condition would be shown with respect to each treatment option available with respect to the condition and the patient.

Continuing with reference to FIG. 22, the alternative exemplary National Average Treatment Outcomes and Probabilities user interface would display for each selected treatment outcome tab, e.g., Urinary function tab 1850', available Treatment Options, e.g., 1820a (Radiation therapy), 1820b (Active surveillance), 1820c (Brachytherapy), and 1820d (Surgery); for each exemplary available Treatment Option, exemplary national average Probabilities (such as would be obtained by the exemplary embodiment from the exemplary Probabilities Data Base 1950 depicted, e.g., in FIGS. 19 and 21) would be displayed, such as, for example, according to High (1841'), Medium (1842') and Low (1843') occurrences of the particular selected outcome associated with the respective available Treatment Options (e.g., for Prostate Cancer, e.g., 1820a (Radiation therapy), 1820b (Active surveillance), 1820c (Brachytherapy), and 1820d (Surgery)). An exemplary Summary 2210 of the probabilities would be provided. In the alternative exemplary National Average Treatment Outcomes and Probabilities user interface, the Treatment Options, e.g., 1820a (Radiation therapy), 1820b (Active surveillance), 1820c (Brachytherapy), and 1820d (Surgery), would be displayed in order according to the above-described conjoint-based analysis of the patient/user's preferences.

In one exemplary embodiment of the present invention, each user would be requested to identify to the exemplary system a final choice of a treatment option and would be requested, such as after the treatment had been implemented, to input any comments the user may have regarding the selected treatment, such as the user's/patient's experience regarding the selected treatment and/or any side effects that the patient may have experienced. Exemplary user input regarding patient treatment and outcomes is discussed further below with reference to FIG. 30.

In one such exemplary embodiment, e.g., the exemplary graphic user interface module (e.g., depicted as one of the exemplary graphic user interface modules 1910, 1920, 1930 and/or 1940 in FIG. 19), or e.g., the exemplary data base interface module 2150 depicted in FIG. 21), would record the user's treatment choice and comments in an exemplary community data base, e.g., 1960 depicted in FIGS. 19 and 21. In one exemplary embodiment, recordation of each user's choices, each user's comments, and each user's medical condition and prognostic indicators, would be made in observance of all laws and governmental regulations regarding patient privacy, e.g., HIPAA (Health Insurance Portability and Accountability Act) privacy rules.

It will be understood by those with ordinary skill in the art that the above-described exemplary features of recording a user's treatment choice and/or comments in an exemplary community data base (e.g., 1960 depicted in FIGS. 19 and 21) would not be limited to an Internet-based embodiment or to any particular conjoint-analysis methodology but rather could be implemented without departing from the spirit of the present invention, in any processing environment whether now known or in the future discovered and/or in conjunction with the previously-above-described choice-based conjoint analysis embodiment and/or in conjunction with other embodiments that use one or more other types of conjoint analysis methodologies.

One exemplary embodiment would facilitate a patient/user searching for and/or selecting a particular physician and/or medical group for the user's consideration for treatment. After a user selects a particular treatment, one exemplary embodiment system 2100 depicted in FIG. 21, would use for example, an exemplary data base interface module 2150, to search an exemplary medical provider data base 2190 and would display to the user an identification of one or more medical providers for providing the selected treatment.

It will be understood by those with ordinary skill in the art that the above-described exemplary feature of providing an exemplary data base interface module 2150, as depicted for example in FIG. 21, to access data bases, determine the appropriate information and provide interactive graphic user interface modules with appropriate information from, or as determined from, such data bases, would not be limited to an Internet-based embodiment or to any particular conjoint-analysis methodology but rather could be implemented without departing from the spirit of the present invention, in any processing environment whether now known or in the future discovered and/or in conjunction with the previously-above-described choice-based conjoint analysis embodiment and/or in conjunction with other embodiments that use one or more other types of conjoint analysis methodologies.

In one exemplary embodiment, the user would be prompted to request, if desired, ranking of providers according to geographic proximity to a user-specified location. One exemplary embodiment system 2100 would rank the display of providers according to the provider's qualifications and/or experience and/or success rate in performing the particular selected treatment. The exemplary data base interface module 2150 would be programmed to search for providers with qualifications and/or experience in performing the particular selected treatment. If requested by the user to observe a geographic location of the user, the exemplary data base interface module 2150 would display qualified providers, with a graphical ranking of the provider's respective experience and/or success rate for performing the particular selected treatment, and would display the providers ranked according to the proximity to the user-specified location.

In one exemplary embodiment, in addition to displaying provider choices, estimated costs for the treatment, and the amount of the estimated costs that would covered by insurance and the portion that would need to be provided by the patient, would also be provided. In one such exemplary embodiment, cost estimates and insurance coverage/user coverage estimates would be provided for each ranked provider.

In the exemplary embodiment system 2100 depicted in FIG. 21, the user would be prompted to input insurance coverage information. The provider search results would indicate acceptance by the displayed providers of the corresponding user-input insurance coverage information. In an alternative embodiment, only providers accepting the user-input indication of insurance coverage would be displayed to the user. In some alternative exemplary embodiments, the medical provider data base would only include providers that contracted with a particular insurance company. In other exemplary embodiments, all available medical providers would be included in the medical provider data base.

In the exemplary embodiment system 2100 depicted in FIG. 21, if insurance coverage for a particular treatment option selected by a user was limited or not available, or if providers with qualifications and/or experience and/or success for providing the particular treatment option selected by the user were limited or not available within a certain (e.g., user-specified) geographical proximity to the user-specified location, the exemplary system 2100 would further report to the user/patient alternative insurance eligibility for, and/or providers with qualifications and/or experience and/or success for providing, alternative treatments available to the user/patient according to the clinical information (medical condition, prognostic indicators, etc.) regarding the user/patient.

It will be understood by those with ordinary skill in the art that the above-described exemplary features of searching, displaying and ranking medical providers, insurance costs and eligibility and estimated insurance and patient costs and coverage regarding a user-selected treatment would not be limited to an Internet-based embodiment or to any particular conjoint-analysis methodology but rather could be implemented without departing from the spirit of the present invention, in any processing environment whether now known or in the future discovered and/or in conjunction with the previously-above-described choice-based conjoint analysis embodiment and/or in conjunction with other embodiments that use one or more other types of conjoint analysis methodologies.

One exemplary embodiment would facilitate a patient/user searching for and/or selecting a particular physician and/or medical group for the user's consideration for treatment based on further search criteria. FIG. 32 is a graphic depiction of an exemplary Patient Physician/Physician Group Search Request Interface for searching for a physician and/or a physician group to provide a selected treatment. FIG. 32 depicts exemplary input fields for Patient Identifier 3201, Patient Name 3203, Patient Condition 3205, Treatment Selected 3207, Insurance Company 3210, Insurance Plan 3215 and Zip Code 3220.

Figure 31:
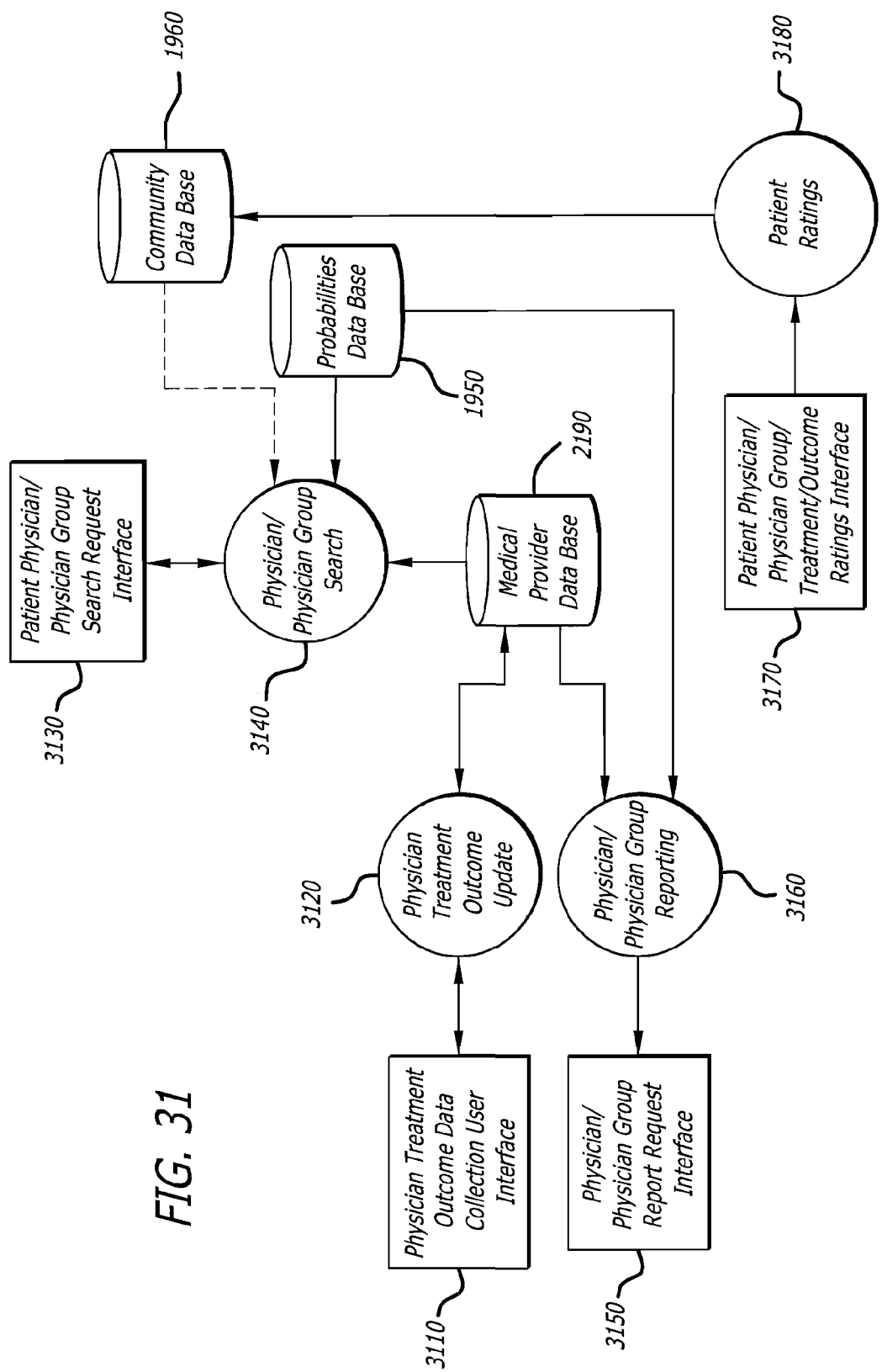
FIG. 31 is a high level diagram depicting high level functions regarding physician treatment outcome data collection and patient searches for physicians and physician groups in an exemplary embodiment of the present invention.

In such an exemplary embodiment, if a patient accessed the exemplary Patient Physician/Physician Group Search Request Interface, the patient would be able to input the Patient Identifier 3201, and the exemplary embodiment would access an exemplary data base containing patient information (e.g., the exemplary Community Data Base 1960 depicted in FIGS. 19, 21 and 31, or alternatively, a separate Patient Data Base (not shown)) and would populate exemplary fields for Patient Name 3203, Patient Condition 3205, Insurance Company 3210, Insurance Plan 3215 and Zip Code 3220. Before searching for a provider or a provider group, the patient would need to input a selected treatment in the exemplary Treatment Selected 3207 input field.

Then the exemplary patient could select one or more exemplary search criteria depicted in FIG. 32. For example, the patient could select exemplary Physician search criteria 3230 to search for a physician; the patient could select exemplary Physician Group search criteria 3240 to search for a physician group. The patient could select the "Within" search criteria 3250 and input a number in the number of miles input field 3252, or could click on the pull-down button 3254 and select a number of miles from a pull-down list (not shown) to search for a physician and/or a physician group (as may have been specified by the patient) within a specified-mile radius from the patient's zip code. The patient could select the insurance plan search criteria 3255 to search for a physician and/or a physician group (as may have been specified by the patient) that accepts the patient's insurance plan. The patient could also select the approved by/within network search criteria 3260 to search for a physician and/or a physician group (as may have been specified by the patient) that is approved by the patient's insurance company/plan and/or within the network of providers accepted by the patient's insurance company/plan.

The above-mentioned exemplary physician/physician group search criteria are illustrative and not a limitation of the present invention. Further search criteria could be made available for searching.

In the exemplary embodiment, users other than patients could use the exemplary search interface depicted in FIG. 32, but would need to input the information into the various exemplary input fields for Patient Name 3203, Patient Condition 3205, Insurance Company 3210, Insurance Plan 3215 and Zip Code 3220.

The exemplary embodiment depicted in FIG. 31 would provide an exemplary Patient Physician/Physician Group Search Request Interface 3130 that would receive input by a user (such as through the exemplary Patient Physician/Physician Group Search Request Interface depicted in FIG. 32) regarding a user's search criteria for searching for a physician and/or a physician group for providing a selected treatment. The exemplary embodiment would provide an exemplary Physician/Physician Group Search function 3140 that would analyze the user's search criteria and would search the exemplary Medical Provider Data Base 2190 in order to identify physicians and/or physician groups that met the user-specified search criteria.

In the exemplary embodiment depicted in FIG. 31, the exemplary Physician/Physician Group Search function 3140 would access the exemplary Probabilities Data Base 1950 and would compare treatment and/or treatment outcome probabilities for physicians and/or physician groups that met the user-specified search criteria with national averages; the exemplary Physician/Physician Group Search function 3140 would use the results of the above-mentioned exemplary comparisons with national averages to produce reports such as depicted, e.g., in FIGS. 26, 27 and 28.

In one exemplary embodiment, additional search criteria would be provided to facilitate a user's specification of certain comparison performance criteria (not shown) so that the user could limit a search, for example, to physicians and/or physician groups that met or exceeded the national average regarding certain treatments and/or outcomes.

In one exemplary embodiment, further additional search criteria would be provided to facilitate a user's specification of certain user rating criteria (not shown) so that a user could limit a search, for example, to physicians and/or physician groups whose previous patients' ratings exceeded a certain specifiable rating and/or rating level. In such an embodiment, the exemplary Physician/Physician. Group Search function 3140 would access the exemplary Community Data Base 1960 as depicted by a dotted line in FIG. 31 in order to identify patient ratings for physicians and/or physician groups that otherwise met the user's search criteria; the exemplary embodiment would compile patient ratings for the relevant physicians and/or physician groups and would limit the report to the searching user according to the user's ratings search criteria.

The description herein of various data bases is exemplary and illustrative and not a limitation of the present invention. For example, in some exemplary embodiment, the exemplary Community Data Base 1960 would be used to record detailed patient identification and/or medical data as well as patient/user physician/physician group rating, patient treatment selection, patient outcome information, user comment information and the like. In other exemplary embodiments, detailed patient identification and/or medical data would be maintained in a separate exemplary Patient Data Base (not shown); the Community Data Base in such an exemplary embodiment would store rating, treatment, outcome and user comment information and the like. Because of the confidentiality of such detailed patient identification and medical data, some embodiments would not record such information permanently beyond a patient's session with an Internet-based version of the system. In other exemplary embodiments, detailed patient medical information would be recorded in an anonymous manner, such as in the exemplary Community Data Base (e.g., element 1960 as depicted in FIG. 31) or in an exemplary Patient Data Base (not shown), so that each user's information would not be identifiable as belonging to a particular person. In yet other exemplary embodiments, such detailed patient identification and/or medical information would be recorded with various encryption and access security measures, such as in the exemplary Community Data Base (e.g., element 1960 as depicted in FIG. 31) or in an exemplary Patient Data Base (not shown).

In one exemplary embodiment, the exemplary Physician/Physician Group Search function 3140 would report, or otherwise make available, such as with a link (not shown) to a user, comments by other users regarding the same or similar treatment and/or outcome and/or the same physician and/or physician group.

FIG. 23 depicts a further alternative exemplary embodiment that, in addition to exemplary National Average Treatment Outcomes and Probabilities as depicted in FIG. 22, would display Treatment Outcomes and Probabilities (e.g, 2350) for a particular provider or for a particular provider group (e.g., 2310), for the same treatment outcomes (e.g., for Prostate cancer, for example, for exemplary selectable possible outcome tabs 1830' (Survival), 1840' (Sexual dysfunction), 1850' (Urinary function), 1860' (Bowel function) and 2280 (Other)). The further alternative exemplary embodiment depicted in FIG. 23 would provide, for example, an exemplary selectable link, such as exemplary selectable link 2320, for displaying a side-by-side comparison of the Provider/Provider Group Treatment Outcomes and Probabilities as displayed in FIG. 23, with National Average Treatment Outcomes and Probabilities as depicted in FIG. 22.

A user selecting the exemplary selectable link 2320 depicted in FIG. 23 would cause the further alternative exemplary embodiment to display an exemplary side-by-side comparison of Provider/Provider Group Treatment Outcomes and Probabilities with National Average Treatment Outcomes and Probabilities for the relevant condition, alternative exemplary displays of which are depicted in FIGS. 24 and 25.

As depicted in FIG. 24, exemplary probabilities 2350 for an exemplary provider group 2310' would be depicted side-by-side with exemplary national average probabilities 2520; in the further alternative exemplary embodiment depicted in FIG. 24, both exemplary sets of probabilities (provider (2350) and national average (2520)) would be displayed according the above-mentioned High, Medium and Low occurrences of the particular selected outcome associated with the respective available Treatment Options (e.g., for Prostate Cancer, e.g., 1820a (Radiation therapy), 1820b (Active surveillance), 1820c (Brachytherapy), and 1820d (Surgery)).

FIG. 25 depicts a further alternative display of a side-by-side comparison of provider probabilities (2350) with graphic summaries of national average probability comparisons (2520'). As depicted in FIG. 25, rather than depict national average probabilities in detail, a graphic representation (e.g., 2610, 2620, 2630 and 2640) would be displayed to depict a graphic comparison of the depicted provider/provider group as compared to national averages. For example, a fully darkened circle (or other graphic symbol), e.g., as depicted by element 2610, would indicate a significantly higher success rate by the particular provider/provider group as compared to national averages for a particular outcome for a particular treatment; a blank circle (or other graphic symbol), e.g., as depicted by element 2630, would indicate that outcomes by the particular provider/provider group matched national averages; a right-half-darkened circle (or other graphic symbol), e.g., as depicted by element 2620, would indicate that the outcomes by the particular provider/provider group fell below national averages.

It will be understood by someone with ordinary skill in the art that the exemplary depicted and discussion herein of circles and darkening of circles for showing comparisons with national averages is illustrative and not a limitation of the invention. Rather, various alternative graphic symbols, including various color-coded symbols and/or words (such as, for example: a Green Plus ("+") sign to designate provider outcome probabilities that exceed the national average; a Red Minus ("−") sign to designate lower-than-national-average provider probabilities; and a black-letter "o" to designate equivalent outcomes), could be used to graphically depict comparisons with national averages without departing from the spirit of the present invention.

In addition to showing comparisons between provider groups and national averages, one alternative exemplary embodiment would also provide a display of physician/provider outcomes as compared to national averages and/or as compared to a group's averages. FIGS. 26 and 27 depict exemplary displays of such provider-level comparisons.

In particular, FIG. 26 depicts exemplary Physician Treatment Summary Graphical Comparisons for an exemplary treatment in an alternative exemplary embodiment of the present invention. The exemplary display in FIG. 26 depicts exemplary summary graphical probability comparisons for an exemplary Treatment (not expressly identified in FIG. 26) for an exemplary list of physicians 2410, listing individual physician names 2420a-2420d, and outcomes 2430 for each physician 2450-2453 as compared to national averages. FIG. 26 also depicts a User Rating 2440 column for display of user ratings for each physician.

FIG. 27 depicts exemplary Physician Treatment Outcomes Graphical Comparisons for an exemplary treatment in an alternative exemplary embodiment of the present invention. FIG. 27 depicts exemplary graphical outcome probability comparisons for an exemplary Treatment (not expressly identified in FIG. 27) for an exemplary list of physicians 2410, listing individual physician names 2420a-2420d; for each physician, a graphic indication (e.g., according to the previously-above-described darkened circle, blank circle and half-darkened circle) of the respective physician's success (e.g., 2450a-2450e) for each treatment outcome (e.g., 2710 (Survival), 2720 (Sexual function), 2730 (Bowel function), 2740 (Urinary function) and 2750 (Other)) is depicted, for example, as compared to national averages.

In order to obtain a display of graphical information regarding an exemplary Physician Level Outcome Comparison as depicted in FIG. 27, a user would input (not shown) a tentative selection of a particular treatment for the patient's medical condition. The exemplary embodiment would also facilitate a user input of physician (or physician group) search criteria that would include, for example, a particular geographical area (e.g., within a specifiable number of miles from a specifiable zip code), and/or a requirement that the search be limited to physicians hat accept a certain type of insurance coverage, and/or that are subscribers to a certain type of insurance plan, and/or according to various other types of search criteria.

The exemplary embodiment would formulate a search of physicians according to the user's input of search criteria and according to the patient's medical condition and selected treatment and would search a memory storage, such as a data base, containing physician and treatment/outcome information. The exemplary search would identify physicians qualified to perform the selected treatment and otherwise conformed with the user's search criteria. The exemplary embodiment would analyze the treatment/outcome information associated with each physician identified by the search; would compare the treatment/outcome information with national averages for the same treatment/outcome; and would identify a graphical symbol for the particular physician for the particular outcome as compared to the national average for the particular outcome for the same treatment.

For example, if the physician's treatment/outcome statistics exceeded national averages for a particular outcome for a particular treatment by more than, for example, ten percent, then the exemplary embodiment would depict a fully darkened circle (or other graphic symbol), e.g., as depicted by element 2450c. If the physician's treatment/outcome statistics did not exceed national averages for a particular outcome for a particular treatment by more than, for example, ten percent, and did not fall below, for example, five percent under the national averages, then the exemplary embodiment would depict, for example, a blank circle (or other graphic symbol), e.g., as depicted by element 2450a. If the physician's treatment/outcome statistics fell below, for example, five percent under the national averages, then the exemplary embodiment would depict, for example, a right-half-darkened circle (or other graphic symbol), e.g., as depicted by element 2450d.

Someone with ordinary skill in the art will understand that the above-mentioned percentages are illustrative and exemplary and not a limitation of the present invention; other criteria could be used to govern the graphical summary depiction of a physician's treatment outcomes as compared to national averages without departing from the spirit of the present invention.

As depicted in FIG. 27, an exemplary instruction 2460 would be provided, indicating that clicking on a particular physician's name would cause a display of detailed probabilities. In the exemplary embodiment, a user clicking on a particular physician's name 2420a-2420d would cause the exemplary embodiment to access a memory storage containing detailed probabilities regarding the relevant outcomes for the relevant treatment by the relevant physician regarding the particular medical condition, and to display the detailed probabilities.

It will be understood by someone with ordinary skill in the art that the exemplary depiction herein of a certain number of physicians, and/or of a single medical group as compared to national averages is illustrative and not a limitation of the present invention. Rather, exemplary embodiments could provide for comparisons across multiple groups and/or for comparisons of a definable plurality of physicians without departing from the spirit of the present invention.

FIG. 28 depicts exemplary Physician Group Outcome Comparisons With National Averages for an exemplary treatment in an exemplary embodiment of the present invention. FIG. 28 depicts exemplary graphical probability comparisons 2800 between an exemplary physician group 2820 and national averages 2830 for exemplary outcomes (e.g., Survival (2840), Sexual Function (2842), Bowel Function (2844), Urinary Function (2846) and Other (2848) for a particular Treatment (not expressly identified in FIG. 28). FIG. 28 depicts exemplary graphical probability summaries (e.g., according to the previously-above-described darkened circle, blank circle and half-darkened circle) 2875a (for exemplary provider group 2820) and 2875b (national average) for an exemplary treatment outcome of Survival 2840; graphical probability summaries 2880a (for exemplary provider group 2820) and 2880b (national average) for an exemplary treatment outcome of Sexual Function 2842; graphical probability summaries 2885a (for exemplary provider group 2820) and 2885b (national average) for an exemplary treatment outcome of Bowel Function 2844; graphical probability summaries 2890a (for exemplary provider group 2820) and 2890b (national average) for an exemplary treatment outcome of Urinary Function 2846; and graphical probability summaries 2895a (for exemplary provider group 2820) and 2895b (national average) for an exemplary treatment outcome of Other 2848.

It will be understood by someone with ordinary skill in the art that the exemplary depiction herein of a single medical group as compared to national averages is illustrative and not a limitation of the present invention. Rather, exemplary embodiments could provide for comparisons across multiple groups without departing from the spirit of the present invention. Further, it will be understood by someone with ordinary skill in the art that the exemplary depiction of particular Outcomes is illustrative and non-limiting; an exemplary embodiment could depict comparisons of various outcomes for various treatments."

Similar to the way in which the exemplary embodiment would generate a display of graphical information regarding an exemplary Physician Level Outcome Comparison as depicted in FIG. 27, in order to obtain a display of graphical information regarding an exemplary Physician Group Outcome Comparison With National Averages as depicted in FIG. 28, a user would input (not shown) a tentative selection of a particular treatment for the patient's medical condition. The exemplary embodiment would also facilitate a user input of physician group treatment search criteria that would include, for example, a particular geographical area (e.g., within a specifiable number of miles from a specifiable zip code), and/or a requirement to search for physician groups that accept a certain type of insurance coverage, and/or that are subscribers to a certain type of insurance plan, and/or according to various other types of search criteria.

The exemplary embodiment would formulate a search of physicians according to the user's input of search criteria and according to the patient's medical condition and selected treatment and would search a memory storage, such as a data base, containing physician and treatment/outcome information. The exemplary search would identify physician groups with physicians that are qualified to perform the selected treatment and that otherwise conformed with the user's search criteria. The exemplary embodiment would analyze the treatment/outcome information associated with each physician group identified by the search; would compare the treatment/outcome information with national averages for the same treatment/outcome; and would identify a graphical symbol for the particular physician group for the particular outcome as compared to the national average for the particular outcome for the same treatment.

For example, if the physician group's treatment/outcome statistics exceeded national averages for a particular outcome for a particular treatment by more than, for example, ten percent, then the exemplary embodiment would depict a fully darkened circle (or other graphic symbol), e.g., as depicted by element 2875a. If the physician group's treatment/outcome statistics did not exceed national averages for a particular outcome for a particular treatment by more than, for example, ten percent, and did not fall below, for example, five percent under the national averages, then the exemplary embodiment would depict, for example, a blank circle (or other graphic symbol), e.g., as depicted by element 2885a. If the physician's treatment/outcome statistics fell below, for example, five percent under the national averages, then the exemplary embodiment would depict, for example, a right-half-darkened circle (or other graphic symbol), (not shown).

Figure 29:
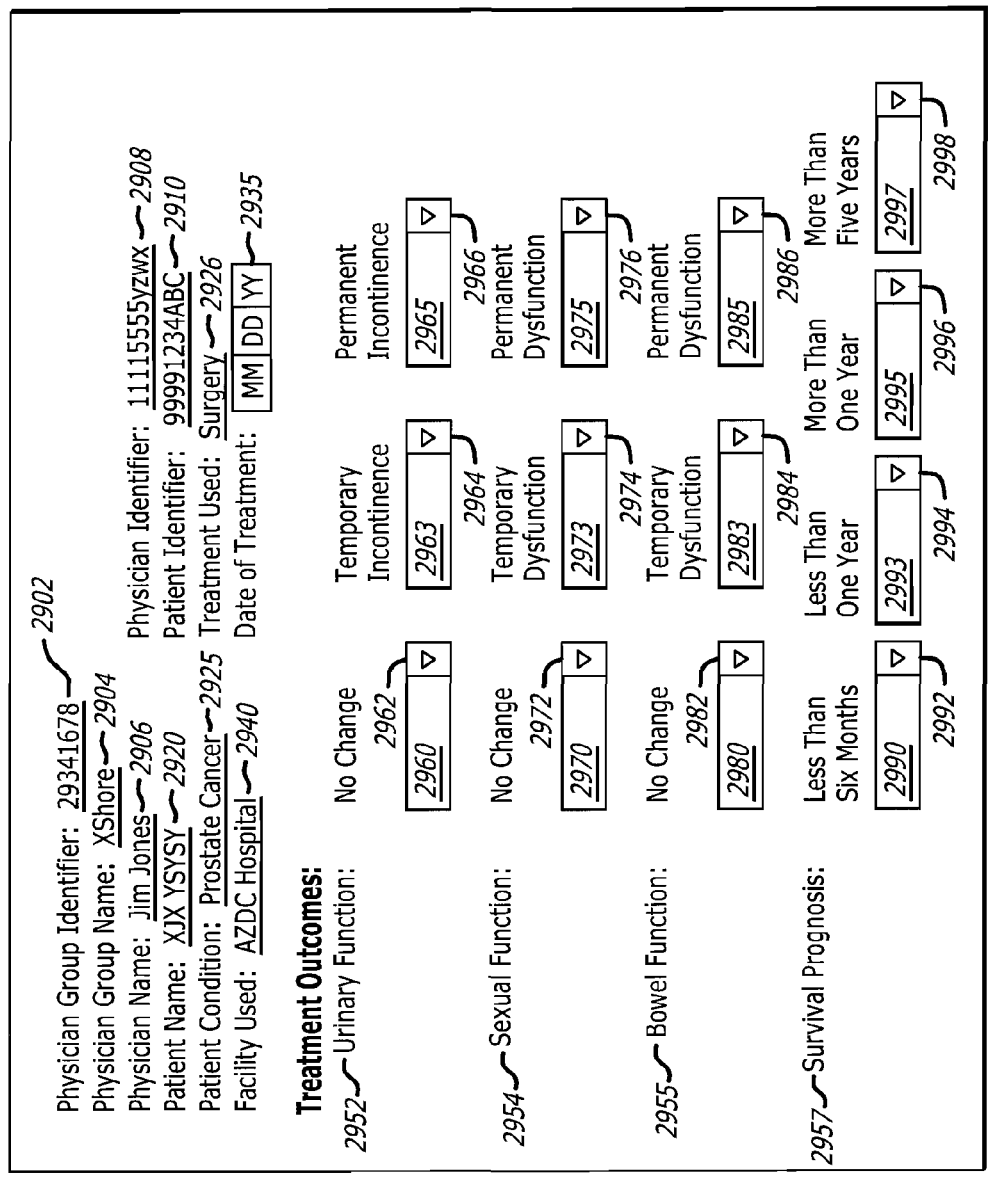
FIG. 29 is a graphic depiction of an exemplary Physician Treatment Outcome. Data Collection User Interface for input and collection of physician treatment outcome data for treatment of a particular patient in an exemplary embodiment of the present invention.

FIG. 29 is a graphic depiction of an exemplary Physician Treatment Outcome Data Collection User Interface for input and collection of physician treatment outcome data for treatment of a particular patient in an exemplary embodiment of the present invention. As depicted in FIG. 29, an exemplary physician user interface would provide exemplary input fields for various identification information, including, for example, an exemplary Physician Group Identifier input field 2902, an exemplary Physician Group Name input field 2904, an exemplary Physician Name input field 2906, an exemplary Physician Identifier input field 2908, an exemplary Patient Name input field 2920, an exemplary Patient Identifier input field 2910, an exemplary Patient Condition input field 2925, an exemplary Treatment Used input field 2926, an exemplary Facility Used input field 2940 (illustratively depicted as a facility name, but could include a facility identifier (not shown)), and an exemplary Date of Treatment input field 2935.

As further depicted in FIG. 29, an exemplary physician user interface would provide exemplary input fields for physician input of estimated probabilities for each outcome category (e.g., Urinary Function 2952, Sexual Function 2954, Bowel Function 2955, and Survival Prognosis 2957) for a particular Treatment 2926 (e.g., Surgery) for a particular Patient Condition 2925 (e.g., prostate cancer). FIG. 29 depicts exemplary outcome probability input fields for each of several possible outcomes. For example, FIG. 29 depicts an exemplary input field for a physician's estimated probability 2960 (with an exemplary pull-down button 2962 for listing (not shown) probability ranges for physician selection) for an exemplary outcome of No Change in Urinary Function (as compared to urinary function prior to the treatment) for the specified patient for the specified treatment. FIG. 29 further depicts exemplary input fields for physician-estimated probabilities, e.g., 2963 and 2965 (with respective pull-down buttons 2964 and 2966) for listing (not shown) probability ranges for physician selection) for exemplary outcomes of Temporary Incontinence and Permanent Incontinence for the specified patient for the specified treatment. FIG. 29 further depicts exemplary input fields for physician probability estimates for other exemplary outcomes for the specified patient for the specified treatment (e.g., No Change in Sexual Function 2970, Temporary Sexual Dysfunction 2973, Permanent Sexual Dysfunction 2975, No Change in Bowel Function 2980, Temporary Bowel Dysfunction 2983, and Permanent Bowel Dysfunction 2985 (with respective pull-down buttons 2972, 2974, 2976, 2982, 2984 and 2986). FIG. 29 further depicts exemplary input fields for physician probability estimates for Survival Prognosis for the specified patient for the specified treatment, e.g., Less Than Six Months 2990, Less Than One Year 2993, More Than One Year 2995 and More Than Five Years 2997 (with exemplary pull-down buttons 2992, 2994, 2996 and 2998).

Someone with ordinary skill in the art will understand that the exemplary depiction in FIG. 29 of exemplary outcomes is illustrative and non-limiting; exemplary embodiments would generate exemplary physician probability estimate collection input fields for each outcome associated with each treatment for each medical condition according to a physician's input of an identification of a medical condition and a treatment used. Some exemplary embodiments would modify generation of exemplary physician probability estimate collection input fields according to a particular patient's prognostic indicators. For example, if a particular patient's prognostic indicators indicated that the patient had already experienced a particular dysfunction, then the exemplary embodiment would, for example, not generate any probability estimate input fields for outcomes for that particular function; or depending on the function, would generate, for example, No Change estimates and/or Permanent Dysfunction estimates.

FIG. 31 is a high level diagram depicting high level functions regarding physician treatment outcome data collection and patient searches for physicians and physician groups in an exemplary embodiment of the present invention. As depicted in FIG. 31, the exemplary embodiment would receive input by a user through an exemplary Physician Treatment Outcome Data Collection User Interface 3110 (such as through an exemplary Physician Treatment Outcome Data Collection User Interface screen such as depicted in FIG. 29). The exemplary embodiment would provide an exemplary Physician Treatment Outcome Update function 3120 that would store the input in a memory storage, such as an exemplary Medical Provider data base 2190.

As further depicted in FIG. 31, the exemplary embodiment would provide an exemplary Physician/Physician Group Report Request Interface 3150 that would receive requests for information regarding physicians and/or physician groups, and/or including other criteria such as treatments and/or outcomes; the exemplary embodiment would provide an exemplary Physician/Physician Group Reporting function 3160 that would analyze information from the Medical Provider Data Base 2190 and the Probabilities Data Base 1950 according to a reporting request and would provide corresponding reports. The exemplary embodiment would provide exemplary reports, such as, for example, regarding treatment outcomes and ratings regarding a report-request-identified medical condition and/or treatment and/or outcome, regarding one or more report-request-identified medical facilities, regarding one or more report-request-identified physicians and/or medical/physician groups, and regarding other types of reporting criteria and/or levels.

FIG. 30 is a graphic depiction of an exemplary Patient User Treatment Outcomes and Ratings Interface for input and collection of a particular patient's treatment outcome data and rating information in an exemplary embodiment of the present invention. The exemplary Patient User Treatment Outcomes and Ratings Interface shown in FIG. 30 depicts exemplary patient identification and treatment input fields for various identification information, including: an exemplary Patient Identifier input field 3010, an exemplary Patient Name input field 3020, an exemplary Patient Condition input field 3025, an exemplary Treatment Used input field 3030 and exemplary treatment date input field 3035, an exemplary Facility Used input field 3040, an exemplary Physician Name input field 3006, an exemplary Physician Identifier input field 3008, an exemplary Physician Group Name input field 3004, and an exemplary Physician Group Identifier input field 3002.

In addition, FIG. 30 depicts exemplary input fields for Treatment Outcomes and Patient Ratings 3042, including, for example, for exemplary outcome and rating categories of Treatment Satisfaction 3050, Urinary Function Impact 3056 and Urinary Function Patient Rating 3060; Sexual Dysfunction Impact 3066 and Sexual Dysfunction Impact Patient Rating 3070; Bowel Function Impact 3076 and Bowel Function Impact Patient Rating 3080; Patient Rating of Physician 3086; Patient Rating of Facility 3090; and Patient Comments 3095.

Someone with ordinary skill in the art will understand that the depiction of certain Treatment Outcomes and Ratings categories (e.g., 3056, 3066, 3076) are illustrative and non-limiting. The exemplary embodiment would generate exemplary Treatment Outcomes and Patient Ratings categories in response to a user inputting the above-mentioned patient identification and treatment information in an exemplary Treatment Outcomes and Patient Ratings screen such as depicted in FIG. 30. For example, for a patient that entered a medical condition of prostate cancer with a treatment of surgery, the exemplary embodiment would generate outcome input fields and rating input fields for outcomes and ratings associated with surgery for prostate cancer. For another patient who enters, for example, a certain type of breast cancer with a certain type of chemotherapy as the treatment received, the exemplary embodiment would generate outcome input fields and rating input fields for outcomes and ratings associated with that type of chemotherapy for that type of breast cancer.

For ratings, FIG. 30 depicts exemplary Rating input fields (e.g., 3052 (for Treatment Satisfaction), 3062 (for Urinary Function Impact rating), 3072 (for Sexual Dysfunction. Impact rating), 3082 (for Bowel Function Impact rating), 3088 (for Patient Rating of Physician) and 3090 (for Patient Rating of Facility), each with a corresponding exemplary pull-down button, e.g., 3054, 3064, 3074, 3084, 3089, and 3093). FIG. 30 further depicts exemplary Treatment Outcome Impact input fields (e.g., 3058 (regarding Urinary Function Impact), 3067 (regarding Sexual Dysfunction Impact), and 3078 (regarding Bowel Function Impact), each with a corresponding exemplary pull-down button, e.g., 3059, 3068, and 3079). Activation of exemplary pull-down rating buttons (e.g., 3054, 3064, 3074, 3084, 3089, and 3093) would cause a selectable display (not shown) of exemplary rating levels, such as, for example, High, Medium and Low. Activation of exemplary outcome pull-down buttons (e.g., 3059, 3068, and 3079) would cause a selectable display (not shown) of exemplary outcome impacts, such as, for example, None, Temporary Dysfunction, Permanent Dysfunction.

FIG. 30 further depicts an exemplary Patient Comments input field 3097 with up and down scroll buttons 3098 for input of patient comments.

Returning with reference to FIG. 31, the exemplary embodiment would provide an exemplary Patient Physician/Physician Group/Treatment/Outcome Ratings Interface 3170 that would receive input by a user (such as through the exemplary Treatment Outcomes and Patient Ratings screen such as depicted in FIG. 30) regarding treatment outcomes and ratings. As depicted in FIG. 31, the exemplary embodiment would provide an exemplary Patient Ratings function 3180 that would store the patient ratings input in a memory storage, such as in an exemplary Community Data Base 1960.

Facsimile Reproduction of Copyright Material

A portion of the disclosure of this patent document contains material which is subject to copyright protection by the copyright owner, WiserCare LLC and/or its successors or assigns. The copyright owner has no objection to the facsimile reproduction by anyone of the patent document or the patent disclosure, as it appears in the Patent and Trademark Office patent file or records, but otherwise reserves all copyright rights whatsoever.

Illustrative Embodiments

Although this invention has been described in certain specific embodiments, many additional modifications and variations would be apparent to those skilled in the art. It is, therefore, to be understood that this invention may be practiced otherwise than as specifically described. Moreover, to those skilled in the various arts, the invention itself herein will suggest solutions to other tasks and adaptations for other applications. Thus, the embodiments of the invention described herein should be considered in all respects as illustrative and not restrictive, the scope of the invention to be determined by the appended claims and their equivalents rather than the foregoing description.

APPENDIX A

EXEMPLARY LEVEL.H AND LEVEL.CPP PROGRAM LISTINGS FOR AN EXEMPLARY INTERNET-BASED EMBODIMENT

```
#pragma once
#include "afx.h"
#include <string>
using std::string;
class CLevel : public CObject
{
public:
    CLevel(void);
    CLevel(const CLevel &level);
    const CLevel &operator=(const CLevel &);
    ~CLevel(void);
private:
    int m_id;
    double m_coefficient;
    int m_count;
    string m_name;
    string m_shortName;
    string m_description;
public:
    int GetID( );
    int GetCount( );
    double GetCoefficient( );
    string GetName( );
    string GetShortName( );
    string GetDescription( );
    void SetID(int id);
    void SetCount(int count);
    void SetCoefficient(double coeff);
    void SetName(string name);
    void SetShortName(string shortName);
    void SetDescription(string description);
};
#include "StdAfx.h"
#include "Level.h"
CLevel::CLevel(void)
{
    m_id = -1;
    m_name = "";
    m_shortName = "";
```

APPENDIX A-continued

EXEMPLARY LEVEL.H AND LEVEL.CPP PROGRAM LISTINGS FOR AN EXEMPLARY INTERNET-BASED EMBODIMENT

```
        m_description = "";
        m_count = 0;
        m_coefficient = 0.0;
}
const CLevel &CLevel::operator=(const CLevel &level)
{
        m_id = level.m_id;
        m_name = level.m_name;
        m_shortName = level.m_shortName;
        m_description = level.m_description;
        m_count = level.m_count;
        m_coefficient = level.m_coefficient;
        return *this;
}
CLevel::CLevel(const CLevel &level)
{
        m_id = level.m_id;
        m_name = level.m_name;
        m_shortName = level.m_shortName;
        m_description = level.m_description;
        m_count = level.m_count;
        m_coefficient = level.m_coefficient;
}
CLevel::~CLevel(void)
{
}
int CLevel::GetID( )
{
        return m_id;
}
int CLevel::GetCount( )
{
        return m_count;
}
double CLevel::GetCoefficient( )
{
        return m_coefficient;
}
string CLevel::GetName( )
{
        return m_name;
}
string CLevel::GetShortName( )
{
        return m_shortName;
}
string CLevel::GetDescription( )
{
        return m_description;
}
void CLevel::SetID(int id)
{
        m_id = id;
}
void CLevel::SetCount(int cnt)
{
        m_count = cnt;
}
void CLevel::SetCoefficient(double coeff)
{
        m_coefficient = coeff;
}
void CLevel::SetName(string name)
{
        m_name = name;
}
void CLevel::SetShortName(string shortName)
{
        m_shortName = shortName;
}
void CLevel::SetDescription(string description)
{
        m_description = description;
}
```

APPENDIX B

EXEMPLARY ATTRIBUTE.H AND ATTRIBUTE.CPP PROGRAM LISTINGS FOR AN EXEMPLARY INTERNET-BASED EMBODIMENT

```
#pragma once
#include "afx.h"
#include <vector>
#include "Level.h"
using std::vector;
class CAttribute : public CObject
{
public:
        CAttribute(void);
        CAttribute(const CAttribute &att);
        const CAttribute &operator=(const CAttribute &);
        ~CAttribute(void);
private:
        int m_id;
        double m_rawpartworthscore;
        double m_scaledpartworthscore;
        string m_name;
        string m_shortName;
        string m_description;
public:
        //Getters
        int GetID( );
        string GetName( );
        string GetShortName( );
        string GetDescription( );
        double GetRawPartWorthScore( );
        double GetScaledPartWorthScore( );
        CLevel GetLevel(int idx);
        const int GetNumberOfLevels( );
        const int GetNumberOfLevelsGreaterThanZero( );
        double GetLevelCoefficient(int i);
        double GetRawPartWorth( );
        vector<CLevel> m_Levels;
        vector<double> m_LevelCoefficients;
        //Setters
        void SetID(int id);
        void SetRawPartWorthScore(double score);
        void SetScaledPartWorthScore(double score);
        void SetName(string name);
        void SetShortName(string shortName);
        void SetDescription(string description);
        void SetLevel(int index, CLevel level);
        void SetLevelCoefficient(int index, double val);
        //Array functions
        void AddLevel(CLevel level);
        void AddLevelCoefficient(double val);
        void ClearArrays( );
};
#include "StdAfx.h"
#include "Attribute.h"
CAttribute::CAttribute(void)
{
        m_id = -1;
        m_name = "";
        m_shortName = "";
        m_description = "";
        //m_Levels.clear( );
        //m_LevelCoefficients.clear( );
        m_rawpartworthscore = 0.0;
        m_scaledpartworthscore = 0.0;
}
const CAttribute &CAttribute::operator=(const CAttribute &att)
{
        m_id = att.m_id;
        m_name = att.m_name;
        m_shortName = att.m_shortName;
        m_description = att.m_description;
        m_Levels = att.m_Levels;
        m_LevelCoefficients = att.m_LevelCoefficients;
        m_rawpartworthscore = att.m_rawpartworthscore;
        m_scaledpartworthscore = att.m_scaledpartworthscore;
        return *this;
}
CAttribute::CAttribute(const CAttribute &att)
{
        m_id = att.m_id;
```

APPENDIX B-continued

EXEMPLARY ATTRIBUTE.H AND ATTRIBUTE.CPP PROGRAM LISTINGS FOR AN EXEMPLARY INTERNET-BASED EMBODIMENT

```
    m__name = att.m__name;
    m__shortName = att.m__shortName;
    m__description = att.m__description;
    m__Levels = att.m__Levels;
    m__LevelCoefficients = att.m__LevelCoefficients;
    m__rawpartworthscore = att.m__rawpartworthscore;
    m__scaledpartworthscore = att.m__scaledpartworthscore;
}
CAttribute::~CAttribute(void)
{
}
int CAttribute::GetID( )
{
    return m__id;
}
double CAttribute::GetRawPartWorthScore( )
{
    return m__rawpartworthscore;
}
double CAttribute::GetScaledPartWorthScore( )
{
    return m__scaledpartworthscore;
}
string CAttribute::GetName( )
{
    return m__name;
}
string CAttribute::GetShortName( )
{
    return m__shortName;
}
string CAttribute::GetDescription( )
{
    return m__description;
}
CLevel CAttribute::GetLevel(int idx)
{
    return m__Levels[idx];
}
void CAttribute::SetID(int id)
{
    m__id = id;
}
void CAttribute::SetName(string name)
{
    m__name = name;
}
void CAttribute::SetRawPartWorthScore(double score)
{
    m__rawpartworthscore = score;
}
void CAttribute::SetScaledPartWorthScore(double score)
{
    m__scaledpartworthscore = score;
}
void CAttribute::SetShortName(string shortName)
{
    m__shortName = shortName;
}
void CAttribute::SetDescription(string description)
{
```

APPENDIX B-continued

EXEMPLARY ATTRIBUTE.H AND ATTRIBUTE.CPP PROGRAM LISTINGS FOR AN EXEMPLARY INTERNET-BASED EMBODIMENT

```
    m__description = description;
}
void CAttribute::SetLevel(int index, CLevel level)
{
    if(m__Levels.size( ) > 0)
    {
        m__Levels[index] = level;
    }
}
void CAttribute::AddLevel(const CLevel level)
{
    m__Levels.push__back(level);
}
void CAttribute::ClearArrays( )
{
    m__Levels.clear( );
    m__LevelCoefficients.clear( );
}
const int CAttribute::GetNumberOfLevels( )
{
    return (int) m__Levels.size( );
}
const int CAttribute::GetNumberOfLevelsGreaterThanZero( )
{
    return (int) m__Levels.size( ) − 1;
}
double CAttribute::GetLevelCoefficient(int i)
{
    return m__LevelCoefficients[i];
}
void CAttribute::SetLevelCoefficient(int index, double val)
{
    m__LevelCoefficients[index] = val;
}
void CAttribute::AddLevelCoefficient(double val)
{
    m__LevelCoefficients.push__back(val);
}
double CAttribute::GetRawPartWorth( )
{
    double max = −999999;
    double min = 99999;
    double zeroVal = 0.001;
    //do not include zero level
    for(int j = 1; j < (int) m__Levels.size( ); j++)
    {
        if(m__Levels[j].GetCoefficient( ) > max)
        {
            max = m__Levels[j].GetCoefficient( );
        }
        if(m__Levels[j].GetCoefficient( ) < min)
        {
            min = m__Levels[j].GetCoefficient( );
        }
    }
    max = (zeroVal > max) ? zeroVal : max;
    min = (zeroVal < min) ? zeroVal : min;
    return (max − min);
}
```

APPENDIX D

EXEMPLARY WCPROFILES.XML PROGRAM LISTING FOR AN EXEMPLARY INTERNET-BASED EMBODIMENT

```
<?xml version="1.0" encoding="utf-8" standalone="yes"?>
<profiles xmlns="http://www.w3.org/2001/XMLSchema-instance">
    <profile id="0" name="Prostate Cancer" shortname="PC" desc="Prostate Cancer Profile">
        <attributes>
            <attribute id="0" name="Sexual Function Effect" shortname="SFE" desc="">
                <levels>
                    <level id="0" name="Sexual Function Effect: Level 0"
```

APPENDIX D-continued

EXEMPLARY WCPROFILES.XML PROGRAM LISTING
FOR AN EXEMPLARY INTERNET-BASED EMBODIMENT

```xml
shortname="SFE0" desc="Sexual Function Effect: No change from before treatment"/>
                        <level id="1" name="Sexual Function Effect: Level 1"
shortname="SFE1" desc="Sexual Function Effect: Temporarily much worse than before treatment, with full
recovery at 12 months"/>
                        <level id="2" name="Sexual Function Effect: Level 2"
shortname="SFE2" desc="Sexual Function Effect: Much worse than before treatment"/>
                        <level id="3" name="Sexual Function Effect: Level 3"
shortname="SFE3" desc="Sexual Function Effect: Slow decline over two years to much worse than
before"/>
                    </levels>
                </attribute>
                <attribute id="1" name="Urinary Control Effect" shortname="UCE" desc="">
                    <levels>
                        <level id="0" name="Urinary Control Effect: Level 0"
shortname="UCE0" desc="Urinary Control Effect: No change from before treatment"/>
                        <level id="1" name="Urinary Control Effect: Level 1"
shortname="UCE1" desc="Urinary Control Effect: Temporarily have leakage with cough or strain, with
full recovery a six months"/>
                        <level id="2" name="Urinary Control Effect: Level 2"
shortname="UCE2" desc="Urinary Control Effect: Have leakage with cough or strain, with no recovery"/>
                    </levels>
                </attribute>
                <attribute id="2" name="Bowel Function Effect" shortname="BFE" desc="">
                    <levels>
                        <level id="0" name="Bowel Function Effect: Level 0"
shortname="BFE0" desc="Bowel Function Effect: No change from before treatment"/>
                        <level id="1" name="Bowel Function Effect: Level 1"
shortname="BFE1" desc="Bowel Function Effect: Temporarily have rectal urgency/frequency, with full
recovery at six months"/>
                        <level id="2" name="Bowel Function Effect: Level 2"
shortname="BFE2" desc="Bowel Function Effect: Have rectal urgency/frequency, with no recovery"/>
                    </levels>
                </attribute>
                <attribute id="3" name="Abdominal Invasiveness Effect" shortname="AIE"
desc="">
                    <levels>
                        <level id="0" name="Abdominal Invasiveness Effect: Level 0"
shortname="AIE0" desc="Abdominal Invasiveness Effect: Non-invasive"/>
                        <level id="1" name="Abdominal Invasiveness Effect: Level 1"
shortname="AIE1" desc="Abdominal Invasiveness Effect: Need for general anesthesia, surgical incision
into abdomen"/>
                    </levels>
                </attribute>
                <attribute id="4" name="Prostate Invasiveness Effect" shortname="PIE" desc="">
                    <levels>
                        <level id="0" name="Prostate Invasiveness Effect: Level 0"
shortname="PIE0" desc="Prostate Invasiveness Effect: Non-invasive"/>
                        <level id="1" name="Prostate Invasiveness Effect: Level 1"
shortname="PIE1" desc="Prostate Invasiveness Effect: Need for general anesthesia, long needles used to
place radioactive seeds into prostate"/>
                    </levels>
                </attribute>
                <attribute id="5" name="Recovery Time Effect" shortname="RTE" desc="">
                    <levels>
                        <level id="0" name="Recovery Time Effect: Level 0"
shortname="RTE0" desc="Recovery Time Effect: None"/>
                        <level id="1" name="Recovery Time Effect: Level 1"
shortname="RTE1" desc="Recovery Time Effect: Two days"/>
                        <level id="2" name="Recovery Time Effect: Level 2"
shortname="RTE2" desc="Recovery Time Effect: Four weeks. Urinary catheter for two weeks"/>
                    </levels>
                </attribute>
                <attribute id="6" name="Operative Complications Effect" shortname="OCE"
desc="">
                    <levels>
                        <level id="0" name="Operative Complications Effect: Level 0"
shortname="OCE0" desc="Operative Complications Effect: None"/>
                        <level id="1" name="Operative Complications Effect: Level 1"
shortname="OCE1" desc="Operative Complications Effect: Experince a blood clot in your leg, requiring
long term medical therapy"/>
                    </levels>
                </attribute>
                <attribute id="7" name="Blood Transfusion Effect" shortname="BTE" desc="">
                    <levels>
                        <level id="0" name="Blood Transfusion Effect: Level 0"
shortname="BTE0" desc="Blood Transfusion Effect: None"/>
                        <level id="1" name="Blood Transfusion Effect: Level 1"
```

APPENDIX D-continued

EXEMPLARY WCPROFILES.XML PROGRAM LISTING
FOR AN EXEMPLARY INTERNET-BASED EMBODIMENT

```
shortname="BTE1" desc="Blood Transfusion Effect: Need for blood transfusion"/>
                    </levels>
                </attribute>
                <attribute id="8" name="Survivability Time Effect" shortname="STE" desc="">
                    <levels>
                        <level id="0" name="Survivability Time Effect: Level 0"
shortname="STE0" desc="Survivability Time Effect: No change from before treatment"/>
                        <level id="1" name="Survivability Time Effect: Level 1"
shortname="STE1" desc="Survivability Time Effect: Six months shorter expected lifetime"/>
                        <level id="2" name="Survivability Time Effect: Level 2"
shortname="STE2" desc="Survivability Time Effect: Twelve months shorter expected lifetime"/>
                    </levels>
                </attribute>
            </attributes>
        </profile>
        <profile id="1" name="Benign Prostatic Hyperplasia" shortname="BPH" desc="Benign Prostatic
Hyperplasia Profile">
            <attributes>
                <attribute id="0" name="Symptom Improvement Effect" shortname="SIE" desc="">
                    <levels>
                        <level id="0" name="Symptom Improvement Effect: Level 0"
shortname="SIE0" desc="Symptom Improvement Effect: Stay the same"/>
                        <level id="1" name="Symptom Improvement Effect: Level 1"
shortname="SIE1" desc="Symptom Improvement Effect: Improve a little"/>
                        <level id="2" name="Symptom Improvement Effect: Level 2"
shortname="SIE2" desc="Symptom Improvement Effect: Completely resolve"/>
                        <level id="3" name="Symptom Improvement Effect: Level 3"
shortname="SIE3" desc="Symptom Improvement Effect: Worsen a little"/>
                        <level id="4" name="Symptom Improvement Effect: Level 4"
shortname="SIE4" desc="Symptom Improvement Effect: Worsen alot"/>
                    </levels>
                </attribute>
                <attribute id="1" name="Urethral Invasiveness Effect" shortname="UIE" desc="">
                    <levels>
                        <level id="0" name="Urethral Invasiveness Effect: Level 0"
shortname="UIE0" desc="Urethral Invasiveness Effect: Non invasive (medical therapy)"/>
                        <level id="1" name="Urethral Invasiveness Effect: Level 1"
shortname="UIE1" desc="Urethral Invasiveness Effect: Office based procedure, with urethal
catheterization"/>
                        <level id="2" name="Urethral Invasiveness Effect: Level 2"
shortname="UIE2" desc="Urethral Invasiveness Effect: Operating room based procedure, with urethral
catheterization"/>
                        <level id="3" name="Urethral Invasiveness Effect: Level 3"
shortname="UIE3" desc="Urethral Invasiveness Effect: Operating room based procedure, with incision and
urethral catheterization"/>
                    </levels>
                </attribute>
                <attribute id="2" name="Recovery" shortname="REC" desc="">
                    <levels>
                        <level id="0" name="Recovery: Level 0" shortname="REC0"
desc="Recovery: No recovery time"/>
                        <level id="1" name="Recovery: Level 1" shortname="REC1"
desc="Recovery: Two weeks"/>
                        <level id="2" name="Recovery: Level 2" shortname="REC2"
desc="Reccvery: One month (with hospital stay of two days)"/>
                    </levels>
                </attribute>
                <attribute id="3" name="Sexual Function Effect" shortname="SFE" desc="">
                    <levels>
                        <level id="0" name="Sexual Function Effect: Level 0"
shortname="SFE0" desc="Sexual Function Effect: Noine"/>
                        <level id="1" name="Sexual Function Effect: Level 1"
shortname="SFE1" desc="Sexual Function Effect: Unable to ejaculate"/>
                    </levels>
                </attribute>
                <attribute id="4" name="Surgical Complications" shortname="SCP" desc="">
                    <levels>
                        <level id="0" name="Surgical Complications: Level 0"
shortname="SCP0" desc="Surgical Complications: None"/>
                        <level id="1" name="Surgical Complications: Level 1"
shortname="SCP1" desc="Surgical Complications: Urethral scarring with need for re-operation"/>
                        <level id="2" name="Surgical Complications: Level 2"
shortname="SCP2" desc="Surgical Complications: Major surgical complication"/>
                    </levels>
                </attribute>
```

APPENDIX D-continued

EXEMPLARY WCPROFILES.XML PROGRAM LISTING
FOR AN EXEMPLARY INTERNET-BASED EMBODIMENT

```xml
        </attributes>
      </profile>
  <profile id="2" name="Test Prostatic Hyperplasia" shortname="BPH" desc="Benign Prostatic Hyperplasia Profile">
    <attributes>
      <attribute id="0" name="Symptom Improvement Effect" shortname="SIE" desc="">
        <levels>
          <level id="0" name="Symptom Improvement Effect: Level 0" shortname="SIE0" desc="Symptom Improvement Effect: Stay the same"/>
          <level id="1" name="Symptom Improvement Effect: Level 1" shortname="SIE1" desc="Symptom Improvement Effect: Improve a little"/>
          <level id="2" name="Symptom Improvement Effect: Level 2" shortname="SIE2" desc="Symptom Improvement Effect: Completely resolve"/>
          <level id="3" name="Symptom Improvement Effect: Level 3" shortname="SIE3" desc="Symptom Improvement Effect: Worsen a little"/>
          <level id="4" name="Symptom Improvement Effect: Level 4" shortname="SIE4" desc="Symptom Improvement Effect: Worsen alot"/>
        </levels>
      </attribute>
      <attribute id="1" name="Urethral Invasiveness Effect" shortname="UIE" desc="">
        <levels>
          <level id="0" name="Urethral Invasiveness Effect: Level 0" shortname="UIE0" desc="Urethral Invasiveness Effect: Non invasive (medical therapy)"/>
          <level id="1" name="Urethral Invasiveness Effect: Level 1" shortname="UIE1" desc="Urethral Invasiveness Effect: Office based procedure, with urethal catheterization"/>
          <level id="2" name="Urethral Invasiveness Effect: Level 2" shortname="UIE2" desc="Urethral Invasiveness Effect: Operating room based procedure, with urethral catheterization"/>
          <level id="3" name="Urethral Invasiveness Effect: Level 3" shortname="UIE3" desc="Urethral Invasiveness Effect: Operating room based procedure, with incision and urethral catheterization"/>
        </levels>
      </attribute>
      <attribute id="2" name="Recovery" shortname="REC" desc="">
        <levels>
          <level id="0" name="Recovery: Level 0" shortname="REC0" desc="Recovery: No recovery time"/>
          <level id="1" name="Recovery: Level 1" shortname="REC1" desc="Recovery: Two weeks"/>
          <level id="2" name="Recovery: Level 2" shortname="REC2" desc="Recovery: One month (with hospital stay of two days)"/>
        </levels>
      </attribute>
      <attribute id="3" name="Sexual Function Effect" shortname="SFE" desc="">
        <levels>
          <level id="0" name="Sexual Function Effect: Level 0" shortname="SFE0" desc="Sexual Function Effect: None"/>
          <level id="1" name="Sexual Function Effect: Level 1" shortname="SFE1" desc="Sexual Function Effect: Unable to ejaculate"/>
        </levels>
      </attribute>
      <attribute id="4" name="Surgical Complications" shortname="SCP" desc="">
        <levels>
          <level id="0" name="Surgical Complications: Level 0" shortname="SCP0" desc="Surgical Complications: None"/>
          <level id="1" name="Surgical Complications: Level 1" shortname="SCP1" desc="Surgical Complications: Urethral scarring with need for re-operation"/>
          <level id="2" name="Surgical Complications: Level 2" shortname="SCP2" desc="Surgical Complications: Major surgical complication"/>
        </levels>
      </attribute>
    </attributes>
  </profile>
</profiles>
```

What is claimed is:

1. A computer-implemented method for providing individualized medical treatment decision support regarding a patient's medical condition, said method comprising:

collecting, using a computer, an identification of a particular patient's medical condition;

collecting, using a computer, information regarding the particular patient's prognostic indicators;

in real-time response to receiving said the particular patient's medical condition and the particular patient's prognostic indicators, dynamically generating, using a computer, a series of interactive conjoint-analysis-based patient preference-assessment exercises according to the particular patient's medical condition and the particular patient's prognostic indicators and further according to statistically-structured, risk-based decision analysis models and mapping trees comprising an indication of medical treatment options available for the patient according to the particular patient's medical condition and the particular patient's prognostic indicators, each patient preference-assessment exercise comprising risk-based medical treatment outcome attributes selected from the group consisting of: at least one medical treatment alternative available for the particular patient according to the particular patient's medical condition and the particular patient's prognostic indicators, at least one medical treatment effect associated with said at least one medical treatment alternative, and at least one medical treatment factor associated with said at least one medical treatment alternative;

collecting, using a computer, a particular user's preferences input in response to said series of interactive, conjoint-analysis-based patient preference-assessment exercises;

determining, using a computer, conjoint-analysis-based, part-worth utility values for said risk-based medical treatment attributes according to a real-time conjoint analysis of the particular user's preferences;

determining from said conjoint-analysis-based, part-worth utility values, using a computer, an expected value for each medical treatment alternative available for the particular patient according to the particular patient's medical condition and according to the particular patient's prognostic indicators; and displaying to a display device, an individualized recommendation of a particular medical treatment alternative according to said ranking.

2. The computer-implemented method of claim 1,
said determining, using a computer, said conjoint-analysis-based, part-worth utility values comprising determining, using a computer, a pattern of the user's preferences using a computer-implemented conjoint analysis of the patient's preferences.

3. The computer-implemented method of claim 1, said collecting, using a computer, a particular user's preferences input in response to said series of interactive, conjoint-analysis-based patient preference-assessment exercises, comprising a computer-implemented conjoint analysis data collection of patient preferences, said patient preferences comprising input selected from the group consisting of:
   a choice of one medical treatment alternative as compared to a second medical treatment alternative,
   a rating of each medical treatment alternative of a plurality of medical treatment alternatives, and
   a choice and a rating of one medical treatment alternative as compared to a second medical treatment alternative.

4. A computer system for providing individualized medical treatment decision support regarding a patient's medical condition, said computer system comprising at least one computer device programmed to:
   receive a user input of a particular patient's patient-specific medical condition and patient-specific prognostic indicators regarding the particular patient, said patient-specific medical condition and patient-specific prognostic indicators corresponding to the particular patient; and
   in response to said user input:
      analyze the particular patient's patient-specific medical condition and patient-specific prognostic indicators,
      determine a set of medical treatment alternatives associated with the particular patient's patient-specific medical condition according to said patient-specific prognostic indicators,
      determine a set of risk-based attributes statistically associated with said set of medical treatment alternatives,
      dynamically generate a first conjoint-analysis-based interactive selection exercise according to the particular patient's patient-specific medical condition and patient-specific prognostic indicators, said first conjoint-analysis-based interactive selection exercise comprising a comparison of at least two hypothetical composite medical treatment alternatives, said first interactive selection exercise comprising an indication of at least a first hypothetical composite medical treatment alternative comprising an indication of a first subset of said set of risk-based attributes and corresponding attribute levels, said first interactive selection exercise further comprising an indication of at least a second hypothetical composite medical treatment alternative comprising a second subset of said set of risk-based attributes and corresponding attribute levels,
      present said first interactive selection exercise to said user, prompting said user to select a treatment alternative from said first hypothetical composite medical treatment alternative and said second hypothetical composite medical treatment alternative, and
      collect from said user said selection by the user of a treatment alternative.

5. The computer system of claim 4, wherein said first interactive selection exercise further comprises a set of interactive preference indicators associated with respective incremental values.

6. The computer system of claim 5, wherein said set of interactive preference indicators is interactively displayed in a visual range from low preference to high preference with respect to said at least a first hypothetical composite medical treatment alternative and said at least a second hypothetical medical treatment alternative.

7. The computer system of claim 4, said at least one computer device further programmed to:
   present a series of interactive selection exercises for user preference rating, and
   receive user input of preferences for each interactive selection exercise in said series.

8. The computer system of claim 7, said at least one computer device further programmed to:
   perform a real-time conjoint analysis of said user input of preferences resulting in a real-time calculation of a conjoint-analysis-based part-worth value for each attribute level of a plurality of attribute levels; and
   based on each said conjoint-analysis-based part-worth value, calculate an expected value for each medical treatment alternative of said set of medical treatment alternatives.

9. The computer system of claim 8, said at least one computer device further programmed to:
   calculate a respective ranking of each medical treatment alternative of said set of medical treatment alternatives according to said expected value.

10. The computer system of claim 9, said at least one computer device further programmed to:
   present a recommendation of a medical treatment approach selected from the set of medical treatment alternatives, said recommendation according to the respective ranking of each medical treatment alternative in the set of medical treatment alternatives.

11. The computer system of claim 9, said at least one computer device further programmed to:
   determine a respective sensitivity of said results of said real-time conjoint analysis regarding each risk-based attribute and corresponding attribute level in said first and second subsets of said set of risk-based attributes and corresponding attribute levels;
   display a real-time report of each said respective sensitivity.

12. The computer system of claim 10, said at least one computer device further programmed to:
    analyze medical care provider qualifications for a plurality of medical care providers;
    identify at least one medical care provider with qualifications that meet a set of requirements for providing the medical treatment approach; and
    display a report of at least one medical care provider with qualifications that meet a set of requirements for providing the medical treatment approach.

13. The computer system of claim 9, said at least one computer device further programmed to:
    display each medical treatment alternative of said set of medical treatment alternatives with a corresponding indication of a respective ranking;
    receive a user selection of a first medical treatment alternative from said set of medical treatment alternatives.

14. The computer system of claim 13, said at least one computer device further programmed to:
    analyze medical care provider qualifications for a plurality of medical care providers;
    identify at least one medical care provider with qualifications that meet a set of requirements for providing the first medical treatment alternative according to said user selection; and
    display a report of at least one medical care provider with qualifications that meet a set of requirements for providing the medical treatment approach.

15. An Internet-based computer system for dynamically generating real-time individualized medical treatment decision support regarding a patient's medical condition, said Internet-based computer system comprising at least one computer device programmed to:
    in real time response to an online input by a user of a particular patient's patient-specific medical condition and associated patient-specific prognostic indicators associated with the particular patient, and according to the particular patient's patient-specific medical condition and said associated patient-specific prognostic indicators, select statistically-structured, risk-based decision analysis models and mapping trees comprising an indication of medical treatment options available for the particular patient according to said particular patient's patient-specific medical condition and said associated patient-specific prognostic indicators and according to associated risk-based treatment attributes, and dynamically generate a series of interactive conjoint-analysis-based medical treatment option selection exercises for the user, each interactive conjoint-analysis-based medical treatment option selection exercise comprising at least two selectable medical treatment options available for the particular patient according to said particular patient's patient-specific medical condition and said associated patient-specific prognostic indicators, each selectable medical treatment option comprising a display of a set of associated risk-based treatment attributes according to said particular patient's patient-specific medical condition and said associated patent-specific prognostic indicators; and
    present the series of interactive conjoint-analysis-based medical treatment option selection exercises to the user, prompting the user to select a treatment option from each interactive conjoint-analysis-based medical treatment option selection exercise in the series and collect from the user each selection by the user of a treatment option.

16. The computer system of claim 15, said at least one computer device further programmed to:
    in real-time response to a series of selections by the user of treatment options selected from the series of interactive conjoint-analysis-based medical treatment option selection exercises:
        perform a real-time conjoint analysis of the series of selections by the user with respect to said medical treatment options available for the particular patient and with respect to said associated risk-based treatment attributes,
        determine, according to said real-time conjoint analysis of the series of selections by the user, a respective patient-specific expected value for each medical treatment option available for the particular patient,
        rank each medical treatment option available for the patient according to the respective patient-specific expected value for each medical treatment option available for the particular patient, and
        present a recommendation of a medical treatment option available for the particular patient according to said rank.

17. The computer system of claim 15, said at least one computer device further programmed to:
    determine, according to a real-time conjoint analysis of the series of selections by the user, a recommendation of a medical treatment option according to a respective ranking of each medical treatment option available to the particular patient, said respective ranking comprising a calculation of an expected value for each medical treatment option available to the particular patient based on said real-time conjoint analysis of said series of selections by the user of treatment options selected from the series of interactive medical treatment option selection exercises; and
    present the recommendation to the user.

18. The computer system of claim 15, said at least one computer device further programmed to:
    determine a respective ranking of each medical treatment option available to the particular patient, said respective ranking comprising a calculation of an expected value for each medical treatment option available to the particular patient based on a real-time conjoint analysis of a series of selections by t e user of treatment options selected from the series of interactive medical treatment option selection exercises;
    present a rank-ordered list of each medical treatment option available to the patient; and
    present an analysis of sensitivity by the patient regarding one or more treatment attributes in the set of associated treatment attributes.

19. The computer system of claim 18, said at least one computer device further programmed to:
    present an option to the user to retake the series of interactive medical treatment option selection exercises;
    in response to a choice of said option by the user to retake the series of interactive medical treatment option selection exercises, present a further series of interactive medical treatment option selection exercises to the user;
    determine a further respective ranking of each medical treatment option available to the patient, said further respective ranking comprising a further calculation of an expected value for each medical treatment option available to the patient based on a further conjoint analysis of a further series of selections by the user of treatment options selected from said further series of interactive medical treatment option selection exercises; and present a further rank-ordered list of each medical treatment option available to the patient.

20. An Internet-based computer system for dynamically generating a real-time individualized medical treatment decision analysis, said Internet-based computer system comprising at least one computer device programmed to:

in real-time response to a particular user's online input of a particular patient's patient-specific medical condition, patient-specific prognostic indicators for the particular patient, and preferences by the particular user regarding risk-based treatment attributes related to a plurality of treatment alternatives available to the particular patient for treating the particular patient's patient-specific medical condition in view of said patient-specific prognostic indicators:

derive conjoint-analysis-based, part-worth utility values for said risk-based treatment attributes from a real-time, individualized conjoint analysis of the particular user's online input of preferences regarding said risk-based treatment attributes;

integrate said conjoint-analysis-based, part-worth utility values with a probability model of medical treatment outcome data for treatment alternatives available to said particular patient for said particular patient's patient-specific medical condition according to said patient-specific prognostic indicators and determine, according to said real-time, individualized conjoint analysis, a respective patient-specific expected value for each medical treatment alternative available to the particular patient for treating the particular patient's patient-specific medical condition in view of said patient-specific prognostic indicators; and generate a real-time display of an individualized decision analysis of medical treatment alternatives available to said particular patient according to said real-time, individualized conjoint analysis of the particular user's online input of preferences, said conjoint-analysis-based, part-worth utility values, said probability model, and said patient-specific expected values.

21. The Internet-based computer system of claim 20, as a predecessor process to said real-time response, said at least one computer device further programmed to:

generate for real-time interaction with said particular user, a series of interactive selection exercises, each said interactive selection exercise comprising at least two hypothetical composite medical treatment alternatives, each hypothetical composite medical treatment alternative comprising a display of a subset of said risk-based treatment attributes, wherein said preferences by the particular user regarding said risk-based treatment attributes comprise a series of selections by the particular user between two hypothetical composite medical treatment alternatives presented by each said interactive selection exercise.

* * * * *